US012364699B2

(12) United States Patent
Brummel et al.

(10) Patent No.: US 12,364,699 B2
(45) Date of Patent: Jul. 22, 2025

(54) METHOD OF TREATING HAIR LOSS DISORDERS

(71) Applicant: Sun Pharmaceutical Industries, Inc., Princeton, NJ (US)

(72) Inventors: Christopher L. Brummel, Lexington, MA (US); James V. Cassella, Lexington, MA (US); Meghan A. Holden, Lexington, MA (US)

(73) Assignee: Sun Pharmaceuticals Industries, Inc., Princeton, NJ (US)

( * ) Notice: Subject to any disclaimer, the term of this patent is extended or adjusted under 35 U.S.C. 154(b) by 0 days.

(21) Appl. No.: 18/905,898

(22) Filed: Oct. 3, 2024

(65) Prior Publication Data

US 2025/0114366 A1 Apr. 10, 2025

Related U.S. Application Data

(60) Provisional application No. 63/697,634, filed on Sep. 23, 2024, provisional application No. 63/675,577, filed on Jul. 25, 2024, provisional application No. 63/673,600, filed on Jul. 19, 2024, provisional application No. 63/625,125, filed on Jan. 25, 2024, provisional application No. 63/543,885, filed on Oct. 12, 2023, provisional application No. 63/543,470, filed on Oct. 10, 2023.

(51) Int. Cl.
*A61K 31/519* (2006.01)
*A61K 9/00* (2006.01)
*A61P 17/14* (2006.01)

(52) U.S. Cl.
CPC .......... *A61K 31/519* (2013.01); *A61K 9/0053* (2013.01); *A61P 17/14* (2018.01)

(58) Field of Classification Search
CPC .............................. A61P 17/14; A61K 31/519
See application file for complete search history.

(56) References Cited

U.S. PATENT DOCUMENTS

| 6,221,335 | B1 | 4/2001 | Foster |
| 6,440,710 | B1 | 8/2002 | Keinan et al. |
| 6,603,008 | B1 | 8/2003 | Ando et al. |
| 7,517,990 | B2 | 4/2009 | Ito et al. |
| 7,598,257 | B2 | 10/2009 | Rodgers et al. |
| 9,000,161 | B2 | 4/2015 | Zhou et al. |
| 9,249,149 | B2 | 2/2016 | Silverman et al. |
| 10,561,659 | B2 * | 2/2020 | Wagner ................ A61K 9/2027 |
| 12,076,323 | B2 | 9/2024 | Wagner et al. |
| 2005/0107420 | A1 | 5/2005 | Armstrong et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2015/0239896 | A1 | 8/2015 | Silverman et al. |
| 2019/0160068 | A1 | 5/2019 | Wagner et al. |
| 2019/0345245 | A1 | 11/2019 | Drevets et al. |
| 2020/0222408 | A1 | 7/2020 | Wagner et al. |
| 2022/0023344 | A1 | 1/2022 | Terrett et al. |
| 2023/0355629 | A1 | 11/2023 | Silverman et al. |
| 2023/0390292 | A1 | 12/2023 | Cassella |
| 2024/0058345 | A1 | 2/2024 | Cassella et al. |

FOREIGN PATENT DOCUMENTS

| WO | 2012/061537 A2 | 5/2012 |
| WO | 2013/188783 A1 | 12/2013 |
| WO | 2017/192905 A1 | 11/2017 |
| WO | 2020/163653 A1 | 8/2020 |
| WO | 2021/236139 A1 | 11/2021 |
| WO | 2022/006541 A1 | 1/2022 |
| WO | 2022/094133 A1 | 5/2022 |

OTHER PUBLICATIONS

Baillie, "The Use of Stable Isotopes in Pharmacological Research," Pharmacological Reviews, 33(2): 81-132 (1981).
Berge et al., "Pharmaceutical Salts," Journal of Pharmaceutical Sciences 66(1):1-9 (1977).
Browne, "Stable Isotope Techniques in Early Drug Development: An Economic Evaluation," J. Clin. Pharmacol. 38: 213-220 (1998).
Cherrah et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
Clinical Trial Listing: Study to Evaluate the Safety and Efficacy of CTP-543 in Adults With Moderate to Severe Alopecia Areata. NCT03137381. Available at https://clinicaltrials.gov/study/NCT03137381?term=NCT03137381&rank=1 (Accessed Nov. 11, 2024).
Clinical Trial Listing: Efficacy and Tolerability Study of Two Dose Regimens of CTP-543 in Adults With Alopecia Areata. NCT03811912. Available at https://clinicaltrials.gov/study/NCT03811912?term=NCT03811912&rank=1. (Accessed Nov. 11, 2024).
Clinical Trial Listing: Efficacy and Tolerability Study of Two Dosing Regimens of CTP-543 in Adults With Alopecia Areata. NCT03941548. Available at https://clinicaltrials.gov/study/NCT03941548?term=NCT03941548&rank=1. (Accessed Nov. 11, 2024).
Clinical Trial Listing: A Study to Evaluate the Durability of Response of CTP-543 in Adult Patients With Moderate to Severe Alopecia Areata. NCT04784533. Available at https://clinicaltrials.gov/study/NCT04784533?term=NCT04784533&rank=1. (Accessed Nov. 11, 2024).
Clinical Trial Listing: Study to Evaluate the Efficacy and Safety of CTP-543 in Adults With Moderate to Severe Alopecia Areata (THRIVE-AA1). NCT04518995. Available at https://clinicaltrials.gov/study/NCT04518995?term=NCT04518995&rank=1. (Accessed Nov. 11, 2024).
Clinical Trial Listing: Study to Evaluate the Efficacy and Safety of CTP-543 in Adults With Moderate to Severe Alopecia Areata (THRIVE-AA2). NCT04797650. Available at https://clinicaltrials.gov/study/NCT04797650?term=NCT04797650&rank=1. (Accessed Nov. 11, 2024).

(Continued)

*Primary Examiner* — Erich A Leeser
(74) *Attorney, Agent, or Firm* — MEDLER FERRO WOODHOUSE & MILLS PLLC

(57) ABSTRACT

The disclosure relates to treatment of Alopecia Areata comprising the administration of Compound (I) or a pharmaceutically acceptable salt thereof.

30 Claims, 15 Drawing Sheets

(56) References Cited

OTHER PUBLICATIONS

Concert Pharmaceuticals Inc. Precision Deuterium Chemistry Backgrounder—Non-Confidential, 2007, pp. 1-6.
Dyck et al., "Effects of Deuterium Substitution on the Catabolism of 13-Phenylethylamine: An In Vivo Study," Journal of Neurochemistry, 46(2): 399-404 (1986).
European Medicines Agency. Cited (2015). "Guideline on the evaluation of the pharmacokinetics of medicinal products in patients with decreased renal function." https://www.ema.europa.eu/en/documents/scientific-guideline/guideline-evaluation-pharmacokinetics-medicinal-products-patients-decreased-renal-function_en.pdf Accessed Aug. 27, 2020.
Food and Drug Administration, Center for Drug Evaluation and Research. Cited (2020). "Pharmacokinetics in patients with impaired renal function—study design, data analysis, and impact on dosing," https://www.fda.gov/media/78573/download Accessed Nov. 4, 2020.
Gannes, LZ et al., (1998) "Natural abundance variations in stable isotopes and their potential uses in animal physiological ecology," Comp Biochem Physiol Mol Integr Physiol, 119(3):725-37.
Gouyette, "Synthesis of Deuterium-labelled Elliptinium and its Use in Metabolic Studies," Biomedical and Environmental Mass Spectrometry, 15: 243-247 (1988).
Haskins, "The Application of Stable Isotopes in Biomedical Research," Biomedical Mass Spectrometry, 9(7): 269-277 (1982).
Honma et al., "The Metabolism of Roxatidine Acetate Hydrochloride," Drug Metabolism and Disposition, 15(4): 551-559 (1987).
Inter Partes Review 2017-01256, which contains a declaration submitted by F. Peter Guengrich.
Johnston, M et al., (2000) "Construct validation of the hospital anxiety and depression scale with clinical populations," J Psychosom Res. 48(6): 579-84.
King BA, et al. (2022) "Defining Severity in Alopecia Areata: Current Perspectives and a Multidimensional Framework," Dermatol Ther (Heidelb). 12(4):825-834.
King et al., (2022) "Two Phase 3 Trials of Baricitinib for Alopecia Areata," N. Engl. J. Med. 386(18):1687-1699.
Manjaly, P. et al., (2021) "Development and validation of the Brigham Eyelash Tool for Alopecia (BELA): A measure of eyelash alopecia areata," J Am Acad Dermatol. 85(1): 271-272.
Olsen EA, et al. (2004) "Alopecia areata investigational assessment guidelines—Part II." J Am Acad Dermatol 51: 440-447.
Pieniaszek et al., "Moricizine Bioavailability via Simultaneous, Dual, Stable Isotope Administration: Bioequivalence Trnplications," J. Clin. Phannacol, 39: 817-825 (1999).
Piliang et al., (2024) "Long-Term Efficacy of Ritlecitinib up to Month 24 From the ALLEGRO Phase 2b/3 and Long-Term Phase 3 Clinical Studies in Alopecia Areata," J. Cutaneous Med, 8:s394.
Roberts SB et al., (2001) "Psychometric evaluation of the Hospital Anxiety and Depression Scale (HADS) among female cardiac patients," Br J Health Psychol. 6: 373-383.
Shilling et al., "Metabolism, Excretion, and Pharmacokinetics of [14C]INCB018424, A Selective Janus Tyrosine Kinase 1/2 Inhibitor, in Humans," Drug Metabolism and Disposition, 38(11):2023-2031 (2010).
Tkachenko, E et al., (2020) "Brigham Eyebrow Tool for Alopecia: A Reliable Assessment of Eyebrow Alopecia Areata," J Investig Dermatol Symp Proc. 20(1): S41-S44.
Tonn et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometry, 22: 633-642 (1993).
Wada E et al., (1994) "Natural abundance of carbon, nitrogen, and hydrogen isotope ratios in biogenic substances: present and future," Seikagaku, 66:15-29.
Wolen, "The Application of Stable Isotopes to Studies of Drug Bioavailability and Bioequivalence," J. Clin. Pharmacol., 26: 419-424 (1986).
Wyrwich KW, et al. (2020) "The alopecia areata investigator global assessment scale: a measure for evaluating clinically meaningful success in clinical trials." Br J Dermatol.; 183:702-9.
Mishra, P., et al., "Baricitinib: First Systemic Oral Drug for Alopecia Therapy," *Journal of Pharmaceutical Care* 10(3):167-173 (2022).
International Search Report and Written Opinion for PCT/US2024/050499 mailed Jan. 14, 2025.

* cited by examiner

| | Deuruxolitinib 8 mg BID (n = 813) | Deuruxolitinib 12 mg BID (n = 662) | Total (N = 1475) |
|---|---|---|---|
| Age (years), Mean (SD) | 38.7 (13.10) | 38.9 (13.13) | 38.8 (13.11) |
| Sex, n (%) | | | |
| Male | 275 (33.8) | 249 (37.6) | 524 (35.5) |
| Female | 538 (66.2) | 413 (62.4) | 951 (64.5) |
| Race, n (%) | | | |
| American Indian or Alaska Native | 4 (0.5) | 2 (0.3) | 6 (0.4) |
| Asian | 52 (6.4) | 43 (6.5) | 95 (6.4) |
| Black or African American | 77 (9.5) | 58 (8.8) | 135 (9.2) |
| Native Hawaiian or Pacific Islander | 5 (0.6) | 2 (0.3) | 7 (0.5) |
| White | 592 (72.8) | 513 (77.5) | 1105 (74.9) |
| Other | 21 (2.6) | 11 (1.7) | 32 (2.2) |
| Multiple | 0 | 3 (0.5) | 3 (0.2) |
| N/A | 62 (7.6) | 30 (4.5) | 92 (6.2) |

FIG. 4

*Analysis includes participants who received deuruxolitinib 8 mg BID consistently from baseline or following placebo. Participants who switched doses were censored. BID, twice daily; BL, baseline; OLE, open-label extension; SALT, Severity of Alopecia Tool.

*Analysis includes participants who received deuruxolitinib 12 mg BID consistently from baseline or following placebo. Participants who switched doses were censored. BID, twice daily; BL, baseline; OLE, open-label extension; SALT, Severity of Alopecia Tool.

METHOD OF TREATING HAIR LOSS DISORDERS

BACKGROUND OF THE INVENTION

Alopecia areata (AA) is an immune-mediated disease of the hair follicle that results in non-scarring hair loss. Individuals with alopecia areata often experience chronic or relapsing disease, with severe psychological consequences. AA subjects have limited treatment options leaving a great clinical need for suitable therapies. The present invention addresses this need by providing therapeutic approaches for the management and treatment of hair loss disorders including alopecia areata.

SUMMARY OF THE INVENTION

The present invention relates to a method of treating alopecia areata.

In a first embodiment, the invention relates to method of treating alopecia areata in a subject in need thereof, the method comprising: determining an estimated glomerular filtration rate of the subject; and orally administering 16 mg/day or 24 mg/day of Compound (I) or a pharmaceutically acceptable salt thereof to the subject, if the subject has an estimated glomerular filtration rate (eGFR) of ≥30 mL/min, MDRD wherein Compound (I) is represented by the following structural formula:

Compound (I)

[Chemical structure]

wherein each position designated specifically as deuterium has at least 95% incorporation of deuterium.

In a first aspect of the first embodiment, the subject has moderate renal impairment (eGFR of 30-59 mL/min, MDRD).

In second aspect of the first embodiment, the subject has mild renal impairment (eGFR of 60-89 mL/min, MDRD)

In a third aspect of the first embodiment, the eGFR of the subject is between ≥30 mL/min, MDRD and <60 mL/min, MDRD.

In a fourth aspect of the first embodiment, the eGFR of the subject is between ≥60 mL/min, MDRD and <90 mL/min, MDRD.

In a fifth aspect of the first embodiment or any one of the first through fourth aspects thereof, the subject has an absolute SALT score of ≥50 at the onset of treatment.

In a sixth aspect of the first embodiment or any one of the first through fourth aspects thereof, the subject has moderate to severe alopecia areata at the onset of treatment.

In a seventh aspect of the first embodiment or any of the first through fourth aspects thereof, the subject has severe alopecia areata at the onset of treatment.

In an eighth aspect of the first embodiment or any one of the first through seventh aspects thereof, after 8 weeks of treating the subject has an absolute SALT score of ≤20.

In a ninth aspect of the first embodiment or any one of the first through seventh aspects thereof, after 12 weeks of treating the subject has an absolute SALT score of ≤20.

In a tenth aspect of the first embodiment or any one of the first through seventh aspects thereof, after 16 weeks of treating the subject has an absolute SALT score of ≤20.

In an eleventh aspect of the first embodiment or any one of the first through seventh aspects thereof, after 20 weeks of treating the subject has an absolute SALT score of ≤20.

In a twelfth aspect of the first embodiment or any one of the first through seventh aspects thereof, after 24 weeks of treating the subject has an absolute SALT score of ≤20.

In a thirteenth aspect of the first embodiment or any one of the first through seventh aspects thereof, after 24 weeks of treating the subject has an absolute SALT score of ≤10.

In a fourteenth aspect of the first embodiment or any one of the first through seventh aspects thereof, after 52 weeks of treating the subject has an absolute SALT score of ≤20.

In a fifteenth aspect of the first embodiment or any one of the first through seventh aspects thereof, after 24 weeks of treating the subject has at least a 75% relative reduction in SALT score.

In a sixteenth aspect of the first embodiment or any one of the first through seventh aspects thereof, after 8 weeks of treating the subject has at least 75% relative reduction in SALT score.

In a seventeenth aspect of the first embodiment or any one of the first through seventh aspects thereof, after 12 weeks of treating the subject has at least 75% relative reduction in SALT score.

In an eighteenth aspect of the first embodiment or any one of the first through seventh aspects thereof, after 24 weeks of treating the subject has at least 90% relative reduction in SALT score.

In a nineteenth aspect of the first embodiment or any one of the first through seventh aspects thereof, after 12 weeks of treating the subject has at least 90% relative reduction in SALT score.

In a twentieth aspect of the first embodiment or any one of the first through seventh aspects thereof, after 24 weeks of treating the subject reports a response of "satisfied" or "very satisfied" on the Hair Satisfaction Patient Reported Outcome (SPRO) scale.

In a twenty-first aspect of the first embodiment or any one of the first through seventh aspects thereof, after 8 weeks of treating the subject reports a response of "satisfied" or "very satisfied" on the Hair Satisfaction Patient Reported Outcome (SPRO) scale.

In a twenty-second aspect of the first embodiment or any one of the first through seventh aspects thereof, after 12 weeks of treating the subject reports a response of "satisfied" or "very satisfied" on the Hair Satisfaction Patient Reported Outcome (SPRO) scale.

In a twenty-third aspect of the first embodiment or any one of the first through seventh aspects thereof, after 12 weeks of treating a reduction in score at least 1.5 points from baseline is reported by the subject on the Hair Satisfaction Patient Reported Outcome (SPRO) scale. For example, the reduction in score is ≥2 points.

In a twenty-fourth aspect of the first embodiment or any one of the first through seventh aspects thereof, after 24 weeks of treating the subject reports a response of "much improved" or "very much improved" using the Patient Global Impression of Improvement (PGI-I).

In a twenty-fifth aspect of the first embodiment or any one of the first through seventh aspects thereof, after 12 weeks of treating the subject reports a response of "much improved" or "very much improved" using the Patient Global Impression of Improvement (PGI-I).

In a twenty-sixth aspect of the first embodiment or any one of the first through seventh aspects thereof, after 16 weeks of treating the subject reports a response of "much improved" or "very much improved" using the Patient Global Impression of Improvement (PGI-I).

In a twenty-seventh aspect of the first embodiment or any one of the first through seventh aspects thereof, after 20 weeks of treating the subject reports a response of "much improved" or "very much improved" using the Patient Global Impression of Improvement (PGI-I).

In a twenty-eighth aspect of the first embodiment or any one of the first through seventh aspects thereof, after 12 weeks of treating a reduction in score of at least 1.5 points from baseline is reported by the subject on the Patient Global Impression of Improvement (PGI-I).

In a twenty-ninth aspect of the first embodiment or any one of the first through seventh aspects thereof, after 16 weeks of treating a reduction in score of at least 1.7 points from baseline is reported by the subject on the Patient Global Impression of Improvement (PGI-I).

In a thirtieth aspect of the first embodiment or any one of the first through seventh aspects thereof, after 24 weeks of treating a reduction in score of at least 2.1 points from baseline is reported by the subject on the Patient Global Impression of Improvement (PGI-I).

In a thirty-first aspect of the first embodiment or any one of the first through seventh aspects thereof, after 24 weeks of treating the subject reports a response of "much improved" or "very much improved" using the Clinical Global Impression of Improvement (CGI-I).

In a thirty-second aspect of the first embodiment or any one of the first through seventh aspects thereof, after 12 weeks of treating the subject reports a response of "much improved" or "very much improved" using the Clinical Global Impression of Improvement (CGI-I).

In a thirty-third aspect of the first embodiment or any one of the first through seventh aspects thereof, after 16 weeks of treating the subject reports a response of "much improved" or "very much improved" using the Clinical Global Impression of Improvement (CGI-I).

In a thirty-fourth aspect of the first embodiment or any one of the first through seventh aspects thereof, after 20 weeks of treating the subject reports a response of "much improved" or "very much improved" using the Clinical Global Impression of Improvement (CGI-I).

In a thirty-fifth aspect of the first embodiment or any one of the first through seventh aspects thereof after 12 weeks of treating a reduction in score of at least 1.0 point from baseline is reported by the subject on the Clinical Global Impression of Severity (CGI-S).

In a thirty-sixth aspect of the first embodiment or any one of the first through seventh aspects thereof, after 16 weeks of treating a reduction in score of at least 1.5 points from baseline is reported by the subject on the Clinical Global Impression of Severity (CGI-S).

In a thirty-seventh aspect of the first embodiment or any one of the first through seventh aspects thereof, after 24 weeks of treating a reduction in score of at least 2.0 from baseline is reported by the subject on the Clinical Global Impression of Severity (CGI-S).

In a thirty-eighth aspect of the first embodiment or any one of the first through seventh aspects thereof, after 24 weeks of treating an increase in score of at least 1.0 point from baseline is achieved by the subject on the Brigham Eyelash Tool for Alopecia (BELA) or the Brigham Eyebrow Tool for Alopecia (BETA).

In a thirty-ninth aspect of the first embodiment or any one of the first through seventh aspects thereof, after 12 weeks of treating an increase in score of at least 0.5 points from baseline is achieved by the subject on the Brigham Eyelash Tool for Alopecia (BELA) or the Brigham Eyebrow Tool for Alopecia (BETA).

In a fortieth aspect of the first embodiment or any one of the first through thirty-ninth aspects thereof the subject is a human. For example, the subject is an adult human. For example, the subject is an adolescent human (12 years to less than 18 years). For example, the subject is a pediatric human (6 years to less than 12 years).

In a forty-first aspect of the first embodiment or any one of the first through thirty-ninth aspects thereof, 16 mg/day of Compound (I) or a pharmaceutically acceptable salt thereof is administered. For example, the 16 mg/day of Compound (I) or a pharmaceutically acceptable salt thereof is administered as 8 mg twice per day.

In a forty-second aspect of the first embodiment or any one of the first through seventh aspects thereof, after 68 weeks of treating the subject has an absolute SALT score of ≤20.

In a second embodiment, the invention relates to a method of treating alopecia areata in a subject in need thereof, the method comprising: determining the complete blood count of the subject; orally administering 16 mg/day or 24 mg/day of Compound (I) or a pharmaceutically acceptable salt thereof to the subject if the subject's complete blood count shows that the ALC is ≥500 cells/µl, the ANC is ≥1000 cells/µl and/or the Hemoglobin level is ≥8 g/dl, wherein, Compound (I) is represented by the following structural formula:

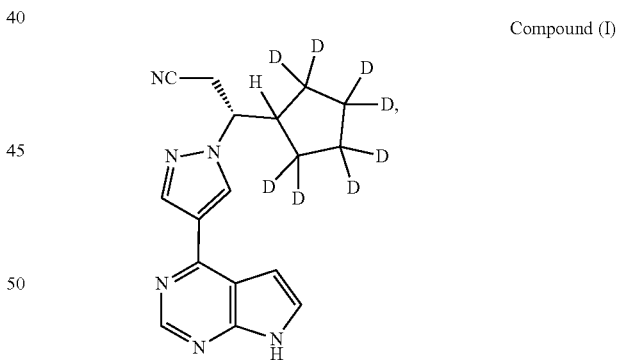

Compound (I)

wherein each position designated specifically as deuterium has at least 95% incorporation of deuterium;
monitoring the ALC, ANC and hemoglobin levels at weeks 4, 8, 16, 20 and 24; and
interrupting treating of the subject if the ALC of the subject is <500 cells/µl, ANC is <1000 cells/µl and/or Hemoglobin level is <8 g/dl.

In a first aspect of the second embodiment, the method further comprises the step of resuming treating the subject when the ALC of the subject is determined to be ≥500 cells/µl, the ANC of the subject is determined to be ≥1000 cells/µl and/or the Hemoglobin level of the subject is determined to be ≥8 g/dl.

In a second aspect of the second embodiment, the method further comprises determining an estimated glomerular filtration rate of the subject; and orally administering 16 mg/day or 24 mg/day of Compound (I) or a pharmaceutically acceptable salt thereof to the subject, if the subject has an estimated glomerular filtration rate (eGFR) of ≥30 mL/min, MDRD. For example, the subject has the subject has moderate renal impairment (eGFR of 30-59 mL/min, MDRD) or the eGFR of the subject is between ≥30 mL/min, MDRD and <60 mL/min, MDRD, or the subject has mild renal impairment (eGFR of 60-89 mL/min, MDRD) or the eGFR of the subject is between ≥60 mL/min, MDRD and <90 mL/min, MDRD.

In a third aspect of the second embodiment or the first or second aspect thereof, the subject has an absolute SALT score of ≥50 at the onset of treatment.

In a fourth aspect of the second embodiment or the first or second aspect thereof, the subject has moderate to severe alopecia areata at the onset of treatment.

In a fifth aspect of the second embodiment or the first or second aspect thereof, the subject has severe alopecia areata at the onset of treatment.

In a sixth aspect of the second embodiment or any one of the first through fifth aspects thereof, after 8 weeks of treating the subject has an absolute SALT score of ≤20.

In a seventh aspect of the second embodiment or any one of the first through fifth aspects thereof, after 12 weeks of treating the subject has an absolute SALT score of ≤20.

In an eighth aspect of the second embodiment or any one of the first through fifth aspects thereof, after 16 weeks of treating the subject has an absolute SALT score of ≤20.

In a ninth aspect of the second embodiment or any one of the first through fifth aspects thereof, after 20 weeks of treating the subject has an absolute SALT score of ≤20.

In a tenth aspect of the second embodiment or any one of the first through fifth aspects thereof, after 24 weeks of treating the subject has an absolute SALT score of ≤20. For example, the subject has an absolute SALT score of ≤10

In an eleventh aspect of the second embodiment or any one of the first through fifth aspects thereof after 52 weeks of treating the subject has an absolute SALT score of ≤20.

In a twelfth aspect of the second embodiment or any one of the first through fifth aspects thereof after 24 weeks of treating the subject has at least a 75% relative reduction in SALT score.

In a thirteenth aspect of the second embodiment or any one of the first through fifth aspects thereof, after 8 weeks of treating the subject has at least 75% relative reduction in SALT score.

In a fourteenth aspect of the second embodiment or any one of the first through fifth aspects thereof, after 12 weeks of treating the subject has at least 75% relative reduction in SALT score.

In a fifteenth aspect of the second embodiment or any one of the first through fifth aspects thereof after 24 weeks of treating the subject has at least 90% relative reduction in SALT score.

In a sixteenth aspect of the second embodiment or any one of the first through fifth aspects thereof after 12 weeks of treating the subject has at least 90% relative reduction in SALT score.

In a seventeenth aspect of the second embodiment or any one of the first through fifth aspects thereof after 24 weeks of treating the subject reports a response of "satisfied" or "very satisfied" on the Hair Satisfaction Patient Reported Outcome (SPRO) scale.

In an eighteenth aspect of the second embodiment or any one of the first through fifth aspects thereof after 8 weeks of treating the subject reports a response of "satisfied" or "very satisfied" on the Hair Satisfaction Patient Reported Outcome (SPRO) scale.

In a nineteenth aspect of the second embodiment or any one of the first through fifth aspects thereof after 12 weeks of treating the subject reports a response of "satisfied" or "very satisfied" on the Hair Satisfaction Patient Reported Outcome (SPRO) scale.

In a twentieth aspect of the second embodiment or any one of the first through fifth aspects thereof, after 12 weeks of treating a reduction in score at least 1.5 points from baseline is reported by the subject on the Hair Satisfaction Patient Reported Outcome (SPRO) scale. For example, the reduction in score is ≥2 points In a twenty-first aspect of the second embodiment or any one of the first through fifth aspects thereof, after 24 weeks of treating the subject reports a response of "much improved" or "very much improved" using the Patient Global Impression of Improvement (PGI-I).

In a twenty-second aspect of the second embodiment or any one of the first through fifth aspects thereof, after 12 weeks of treating the subject reports a response of "much improved" or "very much improved" using the Patient Global Impression of Improvement (PGI-I).

In a twenty-third aspect of the second embodiment or any one of the first through fifth aspects thereof, after 16 weeks of treating the subject reports a response of "much improved" or "very much improved" using the Patient Global Impression of Improvement (PGI-I).

In a twenty-fourth aspect of the second embodiment or any one of the first through fifth aspects thereof after 20 weeks of treating the subject reports a response of "much improved" or "very much improved" using the Patient Global Impression of Improvement (PGI-I).

In a twenty-fifth aspect of the second embodiment or any one of the first through fifth aspects thereof, after 12 weeks of treating a reduction in score of at least 1.5 points from baseline is reported by the subject on the Patient Global Impression of Improvement (PGI-I).

In a twenty-sixth aspect of the second embodiment or any one of the first through fifth aspects thereof after 16 weeks of treating a reduction in score of at least 1.7 points from baseline is reported by the subject on the Patient Global Impression of Improvement (PGI-I).

In a twenty-seventh aspect of the second embodiment or any one of the first through fifth aspects thereof, after 24 weeks of treating a reduction in score of at least 2.1 points from baseline is reported by the subject on the Patient Global Impression of Improvement (PGI-I).

In a twenty-eighth aspect of the second embodiment or any one of the first through fifth aspects thereof after 24 weeks of treating the subject reports a response of "much improved" or "very much improved" using the Clinical Global Impression of Improvement (CGI-I).

In a twenty-ninth aspect of the second embodiment or any one of the first through fifth aspects thereof after 12 weeks of treating the subject reports a response of "much improved" or "very much improved" using the Clinical Global Impression of Improvement (CGI-I).

In a thirtieth aspect of the second embodiment or any one of the first through fifth aspects thereof after 16 weeks of treating the subject reports a response of "much improved" or "very much improved" using the Clinical Global Impression of Improvement (CGI-I).

In a thirty-first aspect of the second embodiment or any one of the first through fifth aspects thereof, after 20 weeks of treating the subject reports a response of "much improved" or "very much improved" using the Clinical Global Impression of Improvement (CGI-I).

In a thirty-second aspect of the second embodiment or any one of the first through fifth aspects thereof after 12 weeks of treating a reduction in score of at least 1.0 point from baseline is reported by the subject on the Clinical Global Impression of Severity (CGI-S).

In a thirty-third aspect of the second embodiment or any one of the first through fifth aspects thereof after 16 weeks of treating a reduction in score of at least 1.5 points from baseline is reported by the subject on the Clinical Global Impression of Severity (CGI-S).

In a thirty-fourth aspect of the second embodiment or any one of the first through fifth aspects thereof after 24 weeks of treating a reduction in score of at least 2.0 from baseline is reported by the subject on the Clinical Global Impression of Severity (CGI-S).

In a thirty-fifth aspect of the second embodiment or any one of the first through fifth aspects thereof after 24 weeks of treating an increase in score of at least 1.0 point from baseline is achieved by the subject on the Brigham Eyelash Tool for Alopecia (BELA) or the Brigham Eyebrow Tool for Alopecia (BETA).

In a thirty-sixth aspect of the second embodiment or any one of the first through fifth aspects thereof after 12 weeks of treating an increase in score of at least 0.5 points from baseline is achieved by the subject on the Brigham Eyelash Tool for Alopecia (BELA) or the Brigham Eyebrow Tool for Alopecia (BETA).

In a thirty-seventh aspect of the second embodiment or any one of the first through thirty-sixth aspects thereof, the subject is a human. For example, an adult human. For example, the subject is an adolescent human (12 years to less than 18 years). For example, the subject is a pediatric human (6 years to less than 12 years).

In a thirty-eighth aspect of the second embodiment or any one of the first through thirty-seventh aspects thereof, 16 mg/day of Compound (I) or a pharmaceutically acceptable salt thereof is administered. For example, the 16 mg/day is administered as 8 mg twice per day.

In a thirty-ninth aspect of the second embodiment or any one of the first through fifth aspects thereof after 68 weeks of treating the subject has an absolute SALT score of ≤20.

In a third embodiment, the invention relates to a method of treating alopecia areata, the method comprising: determining an estimated glomerular filtration rate (eGFR) of a population of subjects suffering from alopecia areata; and orally administering 16 mg/day or 24 mg/day of Compound (I) or a pharmaceutically acceptable salt thereof to a sub-group of the population of subjects having an eGFR of ≥30 mL/min, MDRD, wherein Compound (I) is represented by the following structural formula:

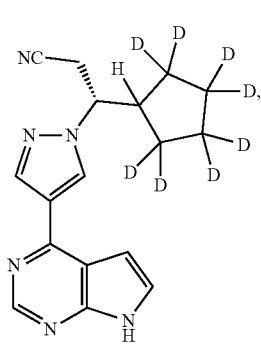

Compound (I)

wherein each position designated specifically as deuterium has at least 95% incorporation of deuterium.

In a first aspect of the third embodiment, the sub-group of the population of subjects has moderate renal impairment (eGFR of 30-59 mL/min, MDRD).

In a second aspect of the third embodiment, the sub-group of the population of subjects has mild renal impairment (eGFR of 30-59 mL/min, MDRD).

In a third aspect of the third embodiment, the eGFR of the sub-group of the population of subjects is between ≥30 mL/min, MDRD and <60 mL/min, MDRD.

In a fourth aspect of the third embodiment, the eGFR of the sub-group of the population of subjects is between ≥60 mL/min, MDRD and <90 mL/min, MDRD.

In a fifth aspect of the third embodiment or any one of the first through fourth embodiments thereof, the sub-group of the population of subjects has an absolute SALT score of ≥50 at the onset of treatment.

In a sixth aspect of the third embodiment or any one of the first through fourth embodiments thereof, the sub-group of the population of subjects has moderate to severe alopecia areata at the onset of treatment.

In a seventh aspect of the third embodiment or any one of the first through fourth embodiments thereof, the sub-group of the population of subjects has severe alopecia areata at the onset of treatment.

In an eighth aspect of the third embodiment or any one of the first through seventh aspects thereof, after 12 weeks of treating at least 5% of the sub-group of the population of subjects has an absolute SALT score of ≤20.

In a ninth aspect of the third embodiment or any one of the first through seventh aspects thereof, after 16 weeks of treating at least 10% of the sub-group of the population of subjects has an absolute SALT score of ≤20.

In a tenth aspect of the third embodiment or any one of the first through seventh aspects thereof, after 20 weeks of treating at least 20% of the sub-group of the population of subjects has an absolute SALT score of ≤20.

In an eleventh aspect of the third embodiment or any one of the first through seventh aspects thereof, after 24 weeks of treating at least 25% of the sub-group of the population of subjects has an absolute SALT score of ≤20.

In a twelfth aspect of the third embodiment or any one of the first through seventh aspects thereof, after 24 weeks of treating at least 15% of the sub-group of the population of subjects has an absolute SALT score of ≤10.

In a thirteenth aspect of the third embodiment or any one of the first through seventh aspects thereof, after 52 weeks of treating at least 50% of the sub-group of the population of subjects has an absolute SALT score of ≤20.

In a fourteenth aspect of the third embodiment or any one of the first through seventh aspects thereof, after 24 weeks of treating at least 30% of the sub-group of the population of subjects has at least a 75% relative reduction in SALT score.

In a fifteenth aspect of the third embodiment or any one of the first through seventh aspects thereof, after 12 weeks of treating at least 7% of the sub-group of the population of subjects has at least 75% relative reduction in SALT score.

In a sixteenth aspect of the third embodiment or any one of the first through seventh aspects thereof, after 24 weeks of treating at least 20% the sub-group of the population of subjects has at least 90% relative reduction in SALT score.

In a seventeenth aspect of the third embodiment or any one of the first through seventh aspects thereof, after 12 weeks of treating at least 1.5% of the sub-group of the population of subjects has at least 90% relative reduction in SALT score.

In an eighteenth aspect of the third embodiment or any one of the first through seventh aspects thereof, after 24 weeks of treating at least 35% of the sub-group of the population of subjects reports a response of "satisfied" or "very satisfied" on the Hair Satisfaction Patient Reported Outcome (SPRO) scale.

In a nineteenth aspect of the third embodiment or any one of the first through seventh aspects thereof, after 12 weeks of treating at least 35% of the sub-group of the population of subjects reports a response of "satisfied" or "very satisfied" on the Hair Satisfaction Patient Reported Outcome (SPRO) scale.

In a twentieth aspect of the third embodiment or any one of the first through seventh aspects thereof, after 20 weeks of treating at least 35% of the sub-group of the population of subjects reports a response of "satisfied" or "very satisfied" on the Hair Satisfaction Patient Reported Outcome (SPRO) scale.

In a twenty-first aspect of the third embodiment or any one of the first through seventh aspects thereof, after 24 weeks of treating at least 50% of the sub-group of the population of subjects reports a response of "satisfied" or "very satisfied" on the Hair Satisfaction Patient Reported Outcome (SPRO) scale.

In a twenty-second aspect of the third embodiment or any one of the first through seventh aspects thereof, after 12 weeks of treating at least 50% of the sub-group of the population of subjects reports a response of "satisfied" or "very satisfied" on the Hair Satisfaction Patient Reported Outcome (SPRO) scale.

In a twenty-third aspect of the third embodiment or any one of the first through seventh aspects thereof, after 20 weeks of treating at least 50% of the sub-group of the population of subjects reports a response of "satisfied" or "very satisfied" on the Hair Satisfaction Patient Reported Outcome (SPRO) scale.

In a twenty-fourth aspect of the third embodiment or any one of the first through seventh aspects thereof, after 12 weeks of treating a reduction in score of at least 1.5 points from baseline is reported by the sub-group of the population of subjects on the Hair Satisfaction Patient Reported Outcome (SPRO) scale.

In a twenty-fifth aspect of the third embodiment or any one of the first through seventh aspects thereof, after 12 weeks of treating a reduction in score of ≥2 points from baseline is reported by at least 45% of the sub-group of the population of subjects on the Hair Satisfaction Patient Reported Outcome (SPRO) scale.

In a twenty-sixth aspect of the third embodiment or any one of the first through seventh aspects thereof, wherein after 24 weeks of treating at least 50% of the sub-group of the population of subjects reports a response of "much improved" or "very much improved" using the Patient Global Impression of Improvement (PGI-I).

In a twenty-seventh aspect of the third embodiment or any one of the first through seventh aspects thereof, after 12 weeks of treating at least 30% of the sub-group of the population of subjects reports a response of "much improved" or "very much improved" using the Patient Global Impression of Improvement (PGI-I).

In a twenty-eighth aspect of the third embodiment or any one of the first through seventh aspects thereof, after 16 weeks of treating at least 40% of the sub-group of the population of subjects reports a response of "much improved" or "very much improved" using the Patient Global Impression of Improvement (PGI-I).

In a twenty-ninth aspect of the third embodiment or any one of the first through seventh aspects thereof, after 20 weeks of treating at least 45% of the sub-group of the population of subjects reports a response of "much improved" or "very much improved" using the Patient Global Impression of Improvement (PGI-I).

In a thirtieth aspect of the third embodiment or any one of the first through seventh aspects thereof, after 12 weeks of treating a reduction in score of at least 1.5 points from baseline is reported by the sub-group of the population of subjects on the Patient Global Impression of Improvement (PGI-I).

In a thirty-first aspect of the third embodiment or any one of the first through seventh aspects thereof, after 16 weeks of treating a reduction in score of at least 1.7 points from baseline is reported by the sub-group of the population of subjects on the Patient Global Impression of Improvement (PGI-I).

In a thirty-second aspect of the third embodiment or any one of the first through seventh aspects thereof, after 24 weeks of treating a reduction in score of at least 2.1 points from baseline is reported by the sub-group of the population of subjects on the Patient Global Impression of Improvement (PGI-I).

In a thirty-third aspect of the third embodiment or any one of the first through seventh aspects thereof, after 24 weeks of treating at least 50% of the sub-group of the population of subjects reports a response of "much improved" or "very much improved" using the Clinical Global Impression of Improvement (CGI-I).

In a thirty-fourth aspect of the third embodiment or any one of the first through seventh aspects thereof, after 12 weeks of treating at least 30% of the sub-group of the population of subjects reports a response of "much improved" or "very much improved" using the Clinical Global Impression of Improvement (CGI-I).

In a thirty-fifth aspect of the third embodiment or any one of the first through seventh aspects thereof, after 16 weeks of treating at least 40% of the sub-group of the population of subjects reports a response of "much improved" or "very much improved" using the Clinical Global Impression of Improvement (CGI-I).

In a thirty-sixth aspect of the third embodiment or any one of the first through seventh aspects thereof, after 20 weeks of treating at least 45% of the sub-group of the population of subjects reports a response of "much improved" or "very much improved" using the Clinical Global Impression of Improvement (CGI-I).

In a thirty-seventh aspect of the third embodiment or any one of the first through seventh aspects thereof, after 12 weeks of treating a reduction in score of at least 1.0 points from baseline is reported by the sub-group of the population of subjects on the Clinical Global Impression of Severity (CGI-S).

In a thirty-eighth aspect of the third embodiment or any one of the first through seventh aspects thereof, after 16 weeks of treating a reduction in score of at least 1.5 points from baseline is reported by the sub-group of the population of subjects on the Clinical Global Impression of Severity (CGI-S).

In a thirty-ninth aspect of the third embodiment or any one of the first through seventh aspects thereof, after 24 weeks of treating a reduction in score of at least 2.0 points from baseline is reported by the sub-group of the population of subjects on the Clinical Global Impression of Severity (CGI-S).

In a fortieth aspect of the third embodiment or any one of the first through seventh aspects thereof, after 24 weeks of treating an increase in score of at least 1.0 points from baseline is achieved by the sub-group of the population of subjects on the Brigham Eyelash Tool for Alopecia (BELA) or the Brigham Eyebrow Tool for Alopecia (BETA).

In a forty-first aspect of the third embodiment or any one of the first through seventh aspects thereof, wherein after 12 weeks of treating an increase in score of at least 0.5 points from baseline is achieved by the sub-group of the population of subjects on the Brigham Eyelash Tool for Alopecia (BELA) or the Brigham Eyebrow Tool for Alopecia (BETA).

In a forty-second aspect of the third embodiment or any one of the first through fortieth aspects thereof, the population of subjects is human. For example, an adult human. For example, the subject is an adolescent human (12 years to less than 18 years). For example, the subject is a pediatric human (6 years to less than 12 years).

In a forty-third aspect of the third embodiment or any one of the first through fortieth aspects thereof, 16 mg/day of Compound (I) or a pharmaceutically acceptable salt thereof is administered. For example, the 16 mg/day of Compound (I) or a pharmaceutically acceptable salt thereof is administered as 8 mg twice per day.

In a forty-fourth aspect of the third embodiment or any one of the first through seventh aspects thereof, after 52 weeks of treating at least 50% of the sub-group of the population of subjects has an absolute SALT score of ≤20.

In a fourth embodiment, the invention relates to a method of treating alopecia areata, the method comprising: orally administering 16 mg/day or 24 mg/day of Compound (I) or a pharmaceutically acceptable salt thereof to a population of subjects, for a first period of 24 weeks of treatment, wherein after the first period at least 30% of the population of subjects have a SALT score of ≤20; and continuing orally administering 16 mg/day or 24 mg/day of Compound (I) or a pharmaceutically acceptable salt thereof to the population of subjects after the end of the first period of 24 weeks of treatment for a second period of at least an additional 52 weeks of treatment, wherein after the second period of treatment at least 50% of the population of subjects have a SALT score of ≤20; wherein Compound (I) is represented by the following structural formula:

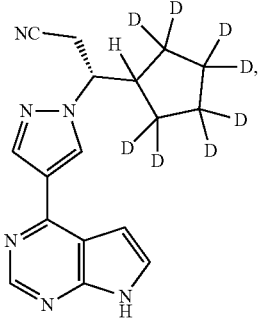

Compound (I)

wherein each position designated specifically as deuterium has at least 95% incorporation of deuterium.

In a first aspect of the fourth embodiment, the subject has an absolute SALT score of ≥50 at the onset of treatment.

In a second aspect of the fourth embodiment, the subject has moderate to severe alopecia areata at the onset of treatment.

In a third aspect of the fourth embodiment, the subject has severe alopecia areata at the onset of treatment.

In a fourth aspect of the fourth embodiment or the first or second aspect thereof, the first period and the second period are continuous.

In a fifth aspect of the fourth embodiment or any one of the first through fourth aspects thereof, the second period is at least 60 weeks.

In a sixth aspect of the fourth embodiment or any one of the first through fifth aspects thereof, the second period is at least 65 weeks. For example, second period is at least 70 weeks. For example, the second period is at least 75 weeks. For example, the second period is at least 80 weeks. For example, the second period is at least 85 weeks. For example, the second period is at least 90 weeks. For example, the second period is at least 95 weeks. For example, the second period is at least 100 weeks.

In a seventh aspect of the fourth embodiment or any one of the first through fifth aspects thereof, after the second period of treatment at least 60% of the population of subjects have a SALT score of ≤20.

In an eighth aspect of the fourth embodiment or any one of the first through fifth aspects thereof, after the second period of treatment at least 70% of the population of subjects have a SALT score of ≤20.

In a ninth aspect of the fourth embodiment or any one of the first through fifth aspects thereof, after the second period of treatment at least 74% of the population of subjects have a SALT score of ≤20.

In a tenth aspect of the fourth embodiment or any one of the first through fifth aspects thereof, after the second period of treatment at least 80% of the population of subjects have a SALT score of ≤20.

In an eleventh aspect of the fourth embodiment or any one of the first through fifth aspects thereof, after the second period of treatment at least 85% of the population of subjects have a SALT score of ≤20.

In a twelfth aspect of the fourth embodiment or any one of the first through fifth aspects thereof, after the second period of treatment at least 90% of the population of subjects have a SALT score of ≤20.

In a thirteenth aspect of the fourth embodiment or any one of the first through twelfth aspects thereof, the population of subjects is human. For example, an adult human. For example, the subject is an adolescent human (12 years to less than 18 years). For example, the subject is a pediatric human (6 years to less than 12 years).

In a fourteenth aspect of the fourth embodiment or any one of the first through thirteenth embodiments thereof, 16 mg/day of Compound (I) or a pharmaceutically acceptable salt thereof is administered. For example, the 16 mg/day of Compound (I) or a pharmaceutically acceptable salt thereof is administered as 8 mg twice per day.

In a fifth embodiment, the invention relates to a method of treating alopecia areata in a subject in need thereof comprising orally administering 16 mg/day or 24 mg/day of Compound (I) or a pharmaceutically acceptable salt thereof to the subject for a first period of 24 weeks and then determining if the subject has a reduction in SALT score to ≤20, and, if not, continuing administration of Compound (I) for a second period of 52 weeks, such that after 52 weeks of treatment the subject achieves a SALT score of ≤20.

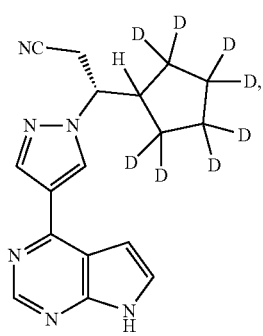

Compound (I)

wherein each position designated specifically as deuterium has at least 95% incorporation of deuterium.

In a sixth embodiment, the invention relates to a method of treating alopecia areata, the method comprising: orally administering 16 mg/day or 24 mg/day of Compound (I) or a pharmaceutically acceptable salt thereof to a population of subjects, for a first period of 24 weeks of treatment, wherein after the first period at least 30% of the population of subjects have a SALT score of ≤20; and continuing orally administering 16 mg/day or 24 mg/day of Compound (I) or a pharmaceutically acceptable salt thereof to the population of subjects after the end of the first period of 24 weeks of treatment for a second period of at least an additional 44 weeks of treatment, wherein after the second period of treatment at least 50% of the population of subjects have a SALT score of ≤20;

wherein Compound (I) is represented by the following structural formula:

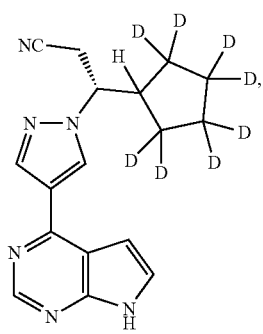

Compound (I)

wherein each position designated specifically as deuterium has at least 95% incorporation of deuterium.

In a first aspect of the sixth embodiment, the subject has an absolute SALT score of ≥50 at the onset of treatment.

In a second aspect of the sixth embodiment, the subject has moderate to severe alopecia areata at the onset of treatment.

In a third aspect of the fourth embodiment, the subject has severe alopecia areata at the onset of treatment.

In a fourth aspect of the sixth embodiment of the first or second aspect thereof, the first period and the second period are continuous.

In a fifth aspect of the sixth embodiment or any one of the first through fourth aspects thereof, the second period is at least 84 weeks. For example, second period is at least 92 weeks. For example, the second period is at least 108 weeks. For example, the second period is at least 140 weeks. For example, the second period is at least 156 weeks. For example, the second period is at least 188 weeks. For example, the second period is at least 220 weeks. For example, the second period is at least 252 weeks.

In a sixth aspect of the sixth embodiment or any one of the first through fifth aspects thereof, after the second period of treatment at least 60% of the population of subjects have a SALT score of ≤20.

In a seventh aspect of the sixth embodiment or any one of the first through fifth aspects thereof, after the second period of treatment at least 70% of the population of subjects have a SALT score of ≤20.

In an eighth aspect of the sixth embodiment or any one of the first through fifth aspects thereof, after the second period of treatment at least 74% of the population of subjects have a SALT score of ≤20.

In a ninth aspect of the sixth embodiment or any one of the first through fifth aspects thereof, after the second period of treatment at least 80% of the population of subjects have a SALT score of ≤20.

In a tenth aspect of the sixth embodiment or any one of the first through fifth aspects thereof, after the second period of treatment at least 85% of the population of subjects have a SALT score of ≤20.

In an eleventh aspect of the sixth embodiment or any one of the first through fifth aspects thereof, after the second period of treatment at least 90% of the population of subjects have a SALT score of ≤20.

In a twelfth aspect of the sixth embodiment or any one of the first through eleventh aspects thereof, the population of subjects is human. For example, an adult human. For example, the subject is an adolescent human (12 years to less than 18 years). For example, the subject is a pediatric human (6 years to less than 12 years).

In a thirteenth aspect of the fourth embodiment or any one of the first through twelfth embodiments thereof, 16 mg/day of Compound (I) or a pharmaceutically acceptable salt thereof is administered. For example, the 16 mg/day of Compound (I) or a pharmaceutically acceptable salt thereof is administered as 8 mg twice per day.

In a seventh embodiment, the invention relates to a method of treating alopecia areata in a subject in need thereof comprising orally administering 16 mg/day or 24 mg/day of Compound (I) or a pharmaceutically acceptable salt thereof to the subject for a first period of 24 weeks and then determining if the subject has a reduction in SALT score to ≤20, and if not continuing administration of Compound (I) for a second period of 44 weeks, such that after 44 weeks of treatment the subject achieves a SALT score of ≤20.

Compound (I)

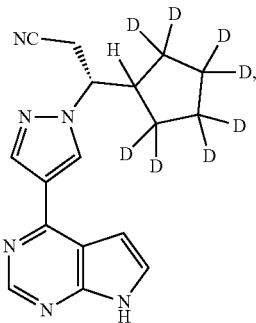

wherein each position designated specifically as deuterium has at least 95% incorporation of deuterium.

In an eighth embodiment, the disclosure provides a method of treating alopecia areata in a subject in need thereof, the method comprising orally administering 16 mg/day or 24 mg/day of Compound (I) or a pharmaceutically acceptable salt thereof to the subject, wherein Compound (I) is represented by the following structural formula:

Compound (I)

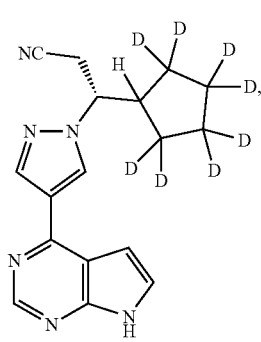

wherein each position designated specifically as deuterium has at least 95% incorporation of deuterium, and wherein the subject has anxiety and/or depression.

In a first aspect of the eighth embodiment, the presence of symptoms of anxiety and depression is determined based on the subject's completion of Hospital Anxiety and Depression Scale (HADS) patient outcome test.

In a second aspect of the eighth embodiment or the first aspects thereof, the subject has a baseline score of >7 for an anxiety or depression subscale on the Hospital Anxiety and Depression Scale (HADS), In a third aspect of the eighth embodiment or any one of the first through second aspects thereof, the subject has a moderate presence of symptoms of anxiety and depression indicated by a score between 8 and 10 on an anxiety or depression subscale of Hospital Anxiety and Depression Scale (HADS) prior to administration of Compound (I).

In a fourth aspect of the eighth embodiment or any one of the first through third aspects thereof, the subject has a severe presence of symptoms of anxiety and depression indicated by a score greater than 11 on an anxiety and depression subscale of Hospital Anxiety and Depression Scale (HADS) prior to administration of Compound (I).

In a fifth aspect of the eighth embodiment or any one of the first through fourth aspects thereof, the subject has a reduction in overall score of at least 1.0 point from baseline as reported by the subject on the Hospital Anxiety and Depression Scale (HADS) after 12 weeks of treating.

In a sixth aspect of the eighth embodiment or any one of the first through fifth aspects thereof, the subject has a reduction in overall score of at least 3.0 points from baseline as reported by the subject on the Hospital Anxiety and Depression Scale (HADS) after 12 weeks of treating.

In a seventh aspect of the eighth embodiment or any one of the first through sixth aspects thereof, the subject has a reduction in overall score of at least 2.0 point from baseline as reported by the subject on the Hospital Anxiety and Depression Scale (HADS) after 16 weeks of treating.

In an eighth aspect of the eighth embodiment or any one of the first through seventh aspects thereof, the subject has a reduction in overall score of at least 4.0 points from baseline as reported by the subject on the Hospital Anxiety and Depression Scale (HADS) after 16 weeks of treating.

In a ninth aspect of the eighth embodiment or any one of the first through eighth aspects thereof, the subject has a reduction in overall score of at least 6.0 point from baseline as reported by the subject on the Hospital Anxiety and Depression Scale (HADS) after 24 weeks of treating.

In a tenth aspect of the eighth embodiment or any one of the first through ninth aspects thereof, the subject has a reduction in overall score of at least 10.0 points from baseline as reported by the subject on the Hospital Anxiety and Depression Scale (HADS) after 24 weeks of treating.

In an eleventh aspect of the eighth embodiment or any one of the first through tenth aspects thereof, the subject has a reduction in Hospital Anxiety and Depression Scale-Anxiety (HADS-A) subscale score of at least 1.0 point from baseline as reported by the subject on the Hospital Anxiety and Depression Scale (HADS) after 12 weeks of treating.

In a twelfth aspect of the eighth embodiment or any one of the first through eleventh aspects thereof, the subject has a reduction in Hospital Anxiety and Depression Scale-Anxiety (HADS-A) subscale score of at least 2.0 points from baseline as reported by the subject on the Hospital Anxiety and Depression Scale (HADS) after 12 weeks of treating.

In a thirteenth aspect of the eighth embodiment or any one of the first through twelfth aspects thereof, the subject has a reduction in Hospital Anxiety and Depression Scale-Anxiety (HADS-A) subscale score of at least 2.0 point from baseline as reported by the subject on the Hospital Anxiety and Depression Scale (HADS) after 16 weeks of treating.

In a fourteenth aspect of the eighth embodiment or any one of the first through thirteenth aspects thereof, the subject has a reduction in Hospital Anxiety and Depression Scale-Anxiety (HADS-A) subscale score of at least 3.0 points from baseline as reported by the subject on the Hospital Anxiety and Depression Scale (HADS) after 16 weeks of treating.

In a fifteenth aspect of the eighth embodiment or any one of the first through fourteenth aspects thereof, the subject has a reduction in Hospital Anxiety and Depression Scale-Anxiety (HADS-A) subscale score of at least 4.0 point from baseline as reported by the subject on the Hospital Anxiety and Depression Scale (HADS) after 24 weeks of treating.

In a sixteenth aspect of the eighth embodiment or any one of the first through fifteenth aspects thereof, the subject has a reduction in Hospital Anxiety and Depression Scale-Anxiety (HADS-A) subscale score of at least 6.0 points from baseline as reported by the subject on the Hospital Anxiety and Depression Scale (HADS) after 24 weeks of treating.

In a seventeenth aspect of the eighth embodiment or any one of the first through fifteenth aspects thereof, the subject has a reduction in Hospital Anxiety and Depression Scale-Depression (HADS-D) subscale score of at least 1.0 point from baseline as reported by the subject on the Hospital Anxiety and Depression Scale (HADS) after 12 weeks of treating.

In an eighteenth aspect of the eighth embodiment or any one of the first through seventeenth aspects thereof, the subject has a reduction in Hospital Anxiety and Depression Scale-Depression (HADS-D) subscale score of at least 2.0 points from baseline as reported by the subject on the Hospital Anxiety and Depression Scale (HADS) after 12 weeks of treating.

In a nineteenth aspect of the eighth embodiment or any one of the first through eighteenth aspects thereof, the subject has a reduction in Hospital Anxiety and Depression Scale-Depression (HADS-D) subscale score of at least 2.0 point from baseline as reported by the subject on the Hospital Anxiety and Depression Scale (HADS) after 16 weeks of treating.

In a twentieth aspect of the eighth embodiment or any one of the first through nineteenth aspects thereof, the subject has a reduction in Hospital Anxiety and Depression Scale-Depression (HADS-D) subscale score of at least 3.0 points from baseline as reported by the subject on the Hospital Anxiety and Depression Scale (HADS) after 16 weeks of treating.

In a twenty-first aspect of the eighth embodiment or any one of the first through twentieth aspects thereof, the subject has a reduction in Hospital Anxiety and Depression Scale-Depression (HADS-D) subscale score of at least 3.0 point from baseline as reported by the subject on the Hospital Anxiety and Depression Scale (HADS) after 24 weeks of treating.

In a twenty-second aspect of the eighth embodiment or any one of the first through twenty-first aspects thereof, the subject has a reduction in Hospital Anxiety and Depression Scale-Depression (HADS-D) subscale score of at least 5.0 points from baseline as reported by the subject on the Hospital Anxiety and Depression Scale (HADS) after 24 weeks of treating.

In a twenty-third aspect of the eighth embodiment or any one of the first through twenty-second aspects thereof, the subject has completed additional primary diagnostic tests used to diagnose anxiety and/or depression before treatment of alopecia areata.

In a twenty-fourth aspect of the eighth embodiment or twenty-third aspect thereof, the additional test is a Generalized Anxiety Disorder questionnaire (GAD-7), Hamilton Rating Scale for Anxiety (HAM-A), Patient Health Questionnaire (PHQ), Beck Depression Inventory (BDI), Center for Epidemiologic Studies Depression Scale (CES-D), EQ-5D, Hamilton Rating Scale for Depression (HAM-D), Montgomery-Åsberg Depression Rating Scale (MADRS) or combinations thereof.

In a twenty-fifth aspect of the eighth embodiment or any one of the first through twenty-fourth aspects thereof, the subject is a human, e.g., the subject is an adult human. In another example, the subject is an adolescent human (12 years to less than 18 years). In another example, the subject is a pediatric human (6 years to less than 12 years).

In a twenty-sixth aspect of the eighth embodiment or any one of the first through twenty-fourth aspects thereof, the subject has moderate to severe alopecia areata at the onset of treatment.

In a twenty-seventh aspect of the eighth embodiment or any one of the first through twenty-fourth aspects thereof, the subject has severe alopecia areata at the onset of treatment.

In a ninth embodiment, the disclosure provides a method of treating alopecia areata in a population of subjects in need thereof, the method comprising:

orally administering 16 mg/day or 24 mg/day of Compound (I) or a pharmaceutically acceptable salt thereof to the population of subjects, wherein Compound (I) is represented by the following structural formula:

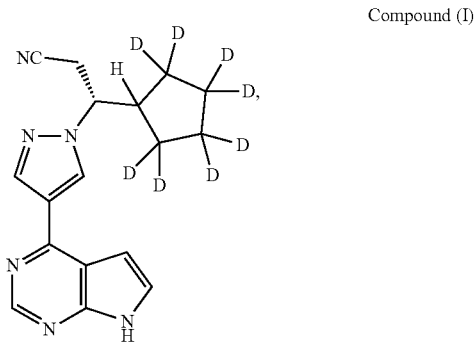

Compound (I)

wherein each position designated specifically as deuterium has at least 95% incorporation of deuterium, wherein the Compound (I) is administered to the population of subjects for at least 52 weeks and wherein the administration of Compound (I) results in maintaining a SALT score of ≤20 in at least 50% of the population of subjects.

In a second aspect of the ninth embodiment, the Compound (I) is administered to the subjects for at least 68 weeks.

In a third aspect of the ninth embodiment, the Compound (I) is administered to the subjects for at least 76 weeks.

In a tenth embodiment, the disclosure provides a method of treating alopecia areata in a subject in need thereof, the method comprising:

orally administering 16 mg/day or 24 mg/day of Compound (I) or a pharmaceutically acceptable salt thereof to the subject, wherein Compound (I) is represented by the following structural formula:

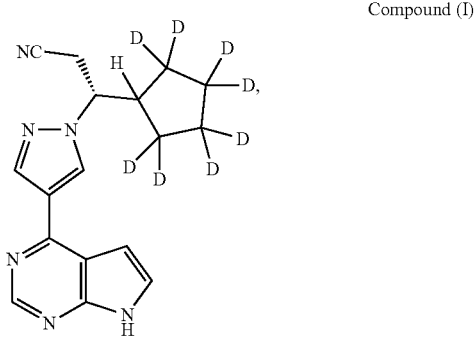

Compound (I)

wherein each position designated specifically as deuterium has at least 95% incorporation of deuterium, wherein the Compound (I) is administered to the subject for at least 52 weeks and wherein the administration of Compound (I) results in maintaining a relative reduction of at least 50% in SALT score.

In a second aspect of the tenth embodiment, the Compound (I) is administered to the subject for at least 68 weeks.

In a second aspect of the tenth embodiment, the Compound (I) is administered to the subject for at least 76 weeks.

In an eleventh embodiment, the disclosure provides a method of treating alopecia areata in a population of subjects in need thereof who were previously administered and discontinued a Janus kinase (JAK) inhibitor, not including Compound (I), the method comprising:

orally administering 16 mg/day or 24 mg/day of Compound (I), or a pharmaceutically acceptable salt thereof, to the population of subjects, wherein Compound (I) is represented by the following structural formula:

Compound (I)

wherein each position designated specifically as deuterium has at least 95% incorporation of deuterium, wherein the Compound (I) is administered to the population of subjects for at least 8 weeks and wherein the administration of Compound (I) results in a SALT score of ≤20 in at least 50% of the population of subjects.

In a first aspect of the eleventh embodiment, the JAK inhibitor includes, but is not limited to, baricitinib, ritlecitinib, and ruxolitinib.

In a second aspect of the eleventh embodiment or the first aspect thereof, Compound (I) is administered to the subjects for at least 12 weeks.

In a third aspect of the eleventh embodiment or the first aspect thereof, Compound (I) is administered to the subjects for at least 16 weeks.

In a fourth aspect of the eleventh embodiment or the first aspect thereof, Compound (I) is administered to the subjects for at least 20 weeks.

In a fifth aspect of the eleventh embodiment or the first aspect thereof, Compound (I) is administered to the subjects for at least 24 weeks.

In a sixth aspect of the eleventh embodiment or the first aspect thereof, Compound (I) is administered to the subjects for at least 52 weeks.

In a seventh aspect of the eleventh embodiment or any one of the first through sixth aspects thereof, the subject has an absolute SALT score of ≥50 at the onset of treatment.

In an eighth aspect of the eleventh embodiment or any one of the first through sixth aspects thereof, the subject has moderate to severe alopecia areata at the onset of treatment.

In a ninth aspect of the eleventh embodiment or any of the first through sixth aspects thereof, the subject has severe alopecia areata at the onset of treatment.

In a tenth aspect of the eleventh embodiment or any one of the first through ninth aspects thereof, after 8 weeks of treating the subject has an absolute SALT score of ≤20.

In an eleventh aspect of the eleventh embodiment or any one of the first through ninth aspects thereof, after 12 weeks of treating the subject has an absolute SALT score of ≤20.

In a twelfth aspect of the eleventh embodiment or any one of the first through ninth aspects thereof, after 16 weeks of treating the subject has an absolute SALT score of ≤20.

In a thirteenth aspect of the eleventh embodiment or any one of the first through ninth aspects thereof, after 20 weeks of treating the subject has an absolute SALT score of ≤20.

In a fourteenth aspect of the eleventh embodiment or any one of the first through ninth aspects thereof, after 24 weeks of treating the subject has an absolute SALT score of ≤20.

In a fifteenth aspect of the eleventh embodiment or any one of the first through ninth aspects thereof, after 24 weeks of treating the subject has an absolute SALT score of ≤10.

In a sixteenth aspect of the eleventh embodiment or any one of the first through ninth aspects thereof, after 52 weeks of treating the subject has an absolute SALT score of ≤20.

In a seventeenth aspect of the eleventh embodiment or any one of the first through ninth aspects thereof, after 24 weeks of treating the subject has at least a 75% relative reduction in SALT score.

In an eighteenth aspect of the eleventh embodiment or any one of the first through ninth aspects thereof, after 8 weeks of treating the subject has at least 75% relative reduction in SALT score.

In a nineteenth aspect of the eleventh embodiment or any one of the first through ninth aspects thereof, after 12 weeks of treating the subject has at least 75% relative reduction in SALT score.

In a twentieth aspect of the eleventh embodiment or any one of the first through ninth aspects thereof, after 24 weeks of treating the subject has at least 90% relative reduction in SALT score.

In a twenty-first aspect of the eleventh embodiment or any one of the first through ninth aspects thereof, after 12 weeks of treating the subject has at least 90% relative reduction in SALT score.

In a twenty-second aspect of the eleventh embodiment or any one of the first through ninth aspects thereof, after 24 weeks of treating the subject reports a response of "satisfied" or "very satisfied" on the Hair Satisfaction Patient Reported Outcome (SPRO) scale.

In a twenty-third aspect of the eleventh embodiment or any one of the first through ninth aspects thereof, after 8 weeks of treating the subject reports a response of "satisfied" or "very satisfied" on the Hair Satisfaction Patient Reported Outcome (SPRO) scale.

In a twenty-fourth aspect of the eleventh embodiment or any one of the first through ninth aspects thereof, after 12 weeks of treating the subject reports a response of "satisfied" or "very satisfied" on the Hair Satisfaction Patient Reported Outcome (SPRO) scale.

In a twenty-fifth aspect of the eleventh embodiment or any one of the first through ninth aspects thereof, after 12 weeks of treating a reduction in score at least 1.5 points from baseline is reported by the subject on the Hair Satisfaction Patient Reported Outcome (SPRO) scale. For example, the reduction in score is ≥2 points.

In a twenty-sixth aspect of the eleventh embodiment or any one of the first through ninth aspects thereof, after 24 weeks of treating the subject reports a response of "much improved" or "very much improved" using the Patient Global Impression of Improvement (PGI-I).

In a twenty-seventh aspect of the eleventh embodiment or any one of the first through ninth aspects thereof, after 12 weeks of treating the subject reports a response of "much improved" or "very much improved" using the Patient Global Impression of Improvement (PGI-I).

In a twenty-eighth aspect of the eleventh embodiment or any one of the first through ninth aspects thereof, after 16 weeks of treating the subject reports a response of "much improved" or "very much improved" using the Patient Global Impression of Improvement (PGI-I).

In a twenty-ninth aspect of the eleventh embodiment or any one of the first through ninth aspects thereof, after 20 weeks of treating the subject reports a response of "much improved" or "very much improved" using the Patient Global Impression of Improvement (PGI-I).

In a thirtieth aspect of the eleventh embodiment or any one of the first through ninth aspects thereof, after 12 weeks of treating a reduction in score of at least 1.5 points from baseline is reported by the subject on the Patient Global Impression of Improvement (PGI-I).

In a thirty-first aspect of the eleventh embodiment or any one of the first through ninth aspects thereof, after 16 weeks of treating a reduction in score of at least 1.7 points from baseline is reported by the subject on the Patient Global Impression of Improvement (PGI-I).

In a thirty-second aspect of the eleventh embodiment or any one of the first through ninth aspects thereof, after 24 weeks of treating a reduction in score of at least 2.1 points from baseline is reported by the subject on the Patient Global Impression of Improvement (PGI-I).

In a thirty-third aspect of the eleventh embodiment or any one of the first through ninth aspects thereof, after 24 weeks of treating the subject reports a response of "much improved" or "very much improved" using the Clinical Global Impression of Improvement (CGI-I).

In a thirty-fourth aspect of the eleventh embodiment or any one of the first through ninth aspects thereof, after 12 weeks of treating the subject reports a response of "much improved" or "very much improved" using the Clinical Global Impression of Improvement (CGI-I).

In a thirty-fifth aspect of the eleventh embodiment or any one of the first through ninth aspects thereof, after 16 weeks of treating the subject reports a response of "much improved" or "very much improved" using the Clinical Global Impression of Improvement (CGI-I).

In a thirty-sixth aspect of the eleventh embodiment or any one of the first through ninth aspects thereof, after 20 weeks of treating the subject reports a response of "much improved" or "very much improved" using the Clinical Global Impression of Improvement (CGI-I).

In a thirty-seventh aspect of the eleventh embodiment or any one of the first through ninth aspects thereof after 12 weeks of treating a reduction in score of at least 1.0 point from baseline is reported by the subject on the Clinical Global Impression of Severity (CGI-S).

In a thirty-eighth aspect of the eleventh embodiment or any one of the first through ninth aspects thereof, after 16 weeks of treating a reduction in score of at least 1.5 points from baseline is reported by the subject on the Clinical Global Impression of Severity (CGI-S).

In a thirty-ninth aspect of the eleventh embodiment or any one of the first through ninth aspects thereof, after 24 weeks of treating a reduction in score of at least 2.0 from baseline is reported by the subject on the Clinical Global Impression of Severity (CGI-S).

In a fortieth aspect of the eleventh embodiment or any one of the first through ninth aspects thereof, after 24 weeks of treating an increase in score of at least 1.0 point from baseline is achieved by the subject on the Brigham Eyelash Tool for Alopecia (BELA) or the Brigham Eyebrow Tool for Alopecia (BETA).

In a forty-first aspect of the eleventh embodiment or any one of the first through ninth aspects thereof, after 12 weeks of treating an increase in score of at least 0.5 points from baseline is achieved by the subject on the Brigham Eyelash Tool for Alopecia (BELA) or the Brigham Eyebrow Tool for Alopecia (BETA).

In a forty-second aspect of the eleventh embodiment or any one of the first through forty-first aspects thereof the subject is a human. For example, the subject is an adult human. For example, the subject is an adolescent human (12 years to less than 18 years). For example, the subject is a pediatric human (6 years to less than 12 years).

In a forty-third aspect of the eleventh embodiment or any one of the first through forty-second aspects thereof, 16 mg/day of Compound (I) or a pharmaceutically acceptable salt thereof is administered. For example, the 16 mg/day of Compound (I) or a pharmaceutically acceptable salt thereof is administered as 8 mg twice per day.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4 is a chart showing patient/subject demographics.

DETAILED DESCRIPTION OF THE INVENTION

Figure 1:
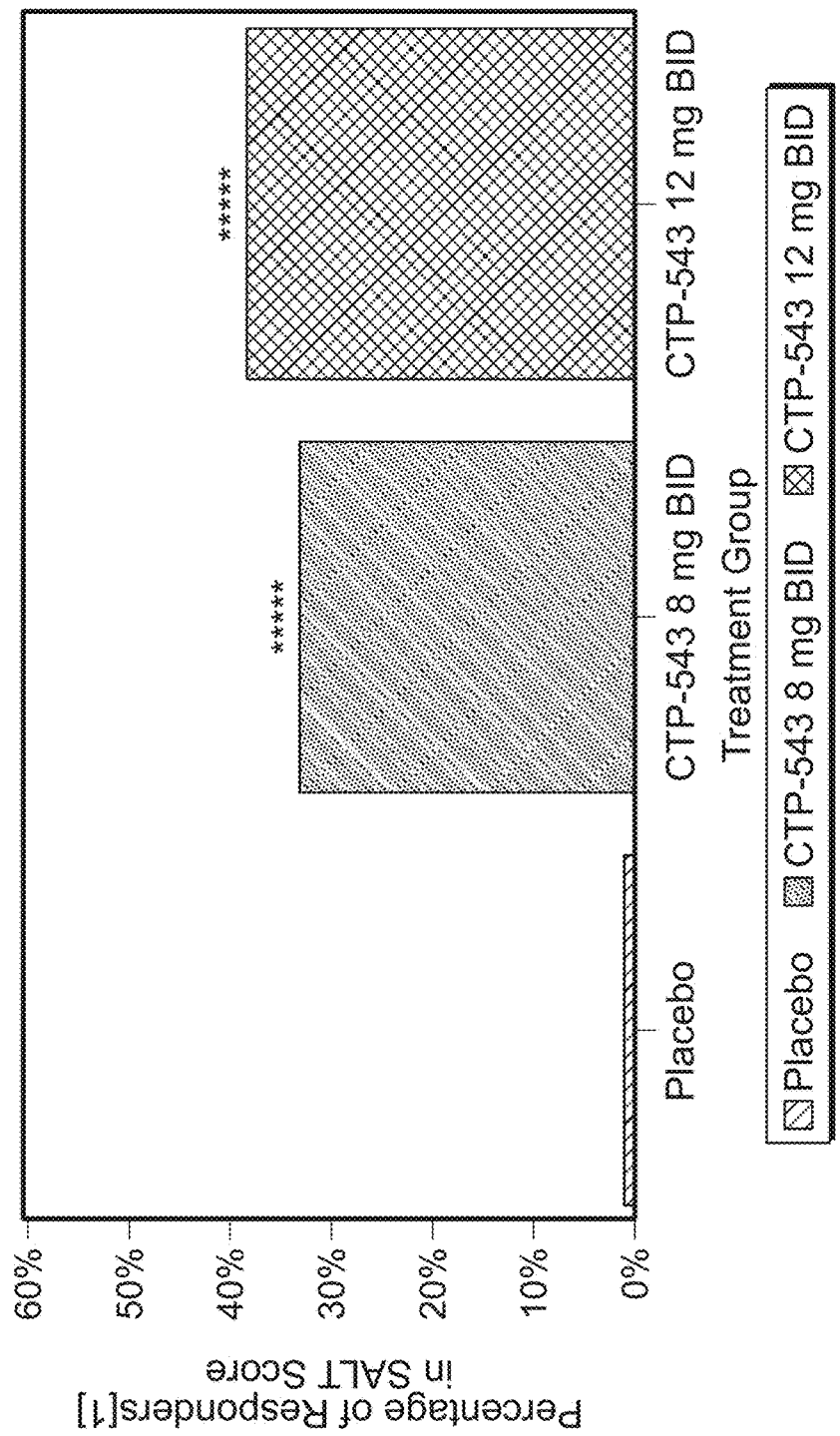
FIG. 1 is a graph showing the percentage of subjects with a SALT score of ≤20 following 24 weeks of treatment with either 8 mg BID or 12 mg BID of CTP-543.

A description of example embodiments of the invention follows.

The teachings of all patents, published applications and references cited herein are incorporated by reference in their entirety.

Hair Loss Disorders

"Hair loss disorder" means any condition or disorder that results in loss of hair on one or more areas of the body. Hair loss disorders include, without limitation, androgenetic alopecia, alopecia areata, telogen effluvium, alopecia totalis, and alopecia universalis. In a specific embodiment the hair loss disorder is alopecia areata.

Alopecia areata is an autoimmune disease that results in partial or complete loss of hair on the scalp and body that may affect up to 650,000 Americans at any given time. The scalp is the most commonly affected area, but any hair-bearing site can be affected alone or together with the scalp. Onset of the disease can occur throughout life and affects both women and men. Alopecia areata can be associated with serious psychological consequences, including anxiety and depression.

In a specific embodiment, the condition is alopecia areata in a subject such as a mammalian (e.g., human) subject (e.g., a patient) in need thereof. In certain embodiments, the alopecia areata is moderate to severe alopecia areata (for example, hair loss over at least 50% of the scalp). Other descriptions of severity of hair loss associate with alopecia areata in those proposed by Wyrwich et al. (Wyrwich K W, et al. The alopecia areata investigator global assessment scale: a measure for evaluating clinically meaningful success in clinical trials. Br J Dermaol. 2020; 183:702-9) wherein the severity of hair loss is described as: no hair loss 0% hair loss; limited hair loss=1-20% hair loss; moderate hair loss=21-49% hair loss; severe hair loss =50-94% hair loss; and very severe hair loss=95-100% hair loss.

JAK Inhibitors

A Janus kinase (JAK) inhibitor, also known as a jakinib, is a type of immune-modulating medication which inhibits the activity of one or more of the Janus kinase family of enzymes (JAK1, JAK2, JAK3, TYK2), thereby interfering with the JAK-STAT signaling pathway in lymphocytes.

In some embodiments, the disclosure provides a method of treating alopecia areata in a subject in need thereof, the method comprising determining an estimated glomerular filtration rate of the subject, and orally administering a Janus kinase (JAK) inhibitor to the subject, if the subject has an estimated glomerular filtration rate (eGFR) of ≥30 mL/min, MDRD.

In some embodiments, the disclosure provides a method of treating alopecia areata in a subject in need thereof, the method comprising orally administering a Janus kinase (JAK) inhibitor to the subject, if the subject has an estimated glomerular filtration rate (eGFR) of ≥30 mL/min, MDRD.

In some embodiments, the disclosure provides method of treating alopecia areata in a subject in need thereof, the method comprising determining the complete blood count of the subject, orally administering a Janus kinase (JAK) inhibitor to the subject if the subject's complete blood count shows that the ALC is ≥500 cells/µl, the ANC is ≥1000 cells/µl and/or the Hemoglobin level is ≥8 g/dl, monitoring the ALC, ANC and Hemoglobin levels, and interrupting treating of the subject if the ALC of the subject is <500 cells/µl, ANC is <1000 cells/µl and/or Hemoglobin level is <8 g/dl. In some embodiments, the method further comprises the step of resuming treating the subject when the ALC of the subject is determined to be ≥500 cells/µl, the ANC of the subject is determined to be ≥1000 cells/µl and/or the Hemoglobin level of the subject is determined to be ≥8 g/dl. In some embodiments, the method further comprises determining an estimated glomerular filtration rate of the subject, and orally administering a JAK inhibitor to the subject, if the subject has an estimated glomerular filtration rate (eGFR) of ≥30 mL/min, MDRD. In some embodiments, the method further comprises orally administering a JAK inhibitor to the subject, if the subject has an estimated glomerular filtration rate (eGFR) of ≥30 mL/min, MDRD.

In some embodiments, the disclosure provides a method of treating alopecia areata, the method comprising determining an estimated glomerular filtration rate (eGFR) of a population of subjects suffering from alopecia areata, and orally administering a JAK inhibitor to a sub-group of the population of subjects having an eGFR of ≥30 mL/min, MDRD. In certain embodiments, the disclosure provides a method of treating alopecia areata, the method comprising orally administering a JAK inhibitor to a sub-group of the population of subjects having an eGFR of ≥30 mL/min, MDRD.

In some embodiments, the disclosure provides a method of treating alopecia areata, the method comprising orally administering a JAK inhibitor to a population of subjects, for a first period of 24 weeks of treatment, wherein after the first period at least 30% of the population of subjects have a SALT score of ≤20, continuing orally administering the JAK inhibitor to the population of subjects after the end of the first period of 24 weeks of treatment for a second period of at least an additional 52 weeks of treatment, wherein after the second period of treatment at least 50% of the population of subjects have a SALT score of ≤20.

In some embodiments, the disclosure provides a method of treating alopecia areata in a subject in need thereof comprising orally administering a JAK inhibitor to the subject for a first period of 24 weeks and then determining if the subject has a reduction in SALT score to ≤20, and, if not, continuing administration of the JAK inhibitor for a second period of 52 weeks, such that after 52 weeks of treatment the subject achieves a SALT score of ≤20.

In some embodiments, the disclosure provides a method of treating alopecia areata in a subject in need thereof, the method comprising orally administering a JAK inhibitor to the subject, wherein the subject has anxiety and/or depression.

In some embodiments, the disclosure provides a method of treating alopecia areata in a population of subjects in need thereof, the method comprising orally administering a JAK inhibitor to the population of subjects, wherein the JAK inhibitor is administered to the population of subjects for at least 52 weeks and wherein the administration of JAK inhibitor results in maintaining a SALT score of ≤20 in at least 50% of the population of subjects.

In some embodiments, the disclosure provides a method of treating alopecia areata in a subject in need thereof, the method comprising orally administering a JAK inhibitor or a pharmaceutically acceptable salt thereof to the subject, wherein the JAK inhibitor is administered to the subject for at least 52 weeks and wherein the administration of JAK inhibitor results in maintaining a relative reduction of at least 50% in SALT score.

In certain embodiments, the JAK inhibitor is a JAK 1 inhibitor. In a certain embodiment, the JAK inhibitor is a JAK 2 inhibitor. In a certain embodiment, the JAK inhibitor inhibits the activity of one or more JAK enzymes. For example, the JAK inhibitor inhibits the activity of JAK1, JAK2 and JAK3. In a certain embodiment, the JAK inhibitor is a JAK1/JAK2 inhibitor.

Compound (I)

Compound I, as referred to herein, is (R)-3-(4-(7H-pyrrolo[2,3-d]pyrimidin-4-yl)-1H-pyrazol-1-yl)-3-(cyclopentyl-2,2,3,3,4,4,5,5-d8) propanenitrile:

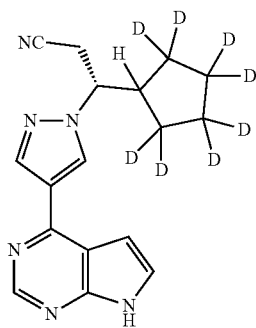 [SMILES: [2H]C1([2H])C([C@@H](CC#N)n2cc(-c3ncnc4[nH]ccc34)cn2)C([2H])([2H])C([2H])([2H])C1([2H])[2H]]

Compound (I) is also referred to herein as CTP-543 and deuruxolitinib, also referred to herein as LEQSELVI™, is a potent selective inhibitor of Janus kinases JAK1 and JAK2. The compound is disclosed in International Patent Applications WO 2013/188783A1, WO 2017/192905A1 and WO2020/163653. CTP-543 is currently being investigated in human clinical trials as described herein and has been shown to stimulate hair growth in subjects suffering from alopecia areata.

The synthesis of Compound (I), or a pharmaceutically acceptable salt thereof (such as the phosphate salt) may be readily achieved by the methods described U.S. Pat. No. 9,249,149, WO 2017/192905A1, WO2020/163653 and U.S. Pat. No. 10,561,659, the teachings of all of which are incorporated herein by reference, with appropriate modifications, if needed.

Additional methods of preparing ruxolitinib (i.e., the non-deuterated analog Compound (I)) are disclosed in U.S. Pat. No. 9,000,161, and can be used, with use of suitable deuterated reagents, to prepare Compound (I).

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

It will be recognized that some variation of natural isotopic abundance occurs in a synthesized compound depending upon the origin of chemical materials used in the synthesis. Thus, a preparation of ruxolitinib will inherently contain small amounts of deuterated isotopologues. The concentration of naturally abundant stable hydrogen and carbon isotopes, notwithstanding this variation, is small and immaterial as compared to the degree of stable isotopic substitution of the deuterated compounds of this invention (e.g., Compound (I)). See, for instance, Wada, E et al., Seikagaku, 1994, 66:15; Gannes, L Z et al., Comp Biochem Physiol Mol Integr Physiol, 1998, 119:725.

In any of the compounds described herein, for example Compound (I), any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. However, in certain embodiments where stated, when a position is designated specifically as "H" or "hydrogen", the position has at least 80%, at least 90%, at least 95%, at least 96%, at least 97%, at least 98%, or at least 99% hydrogen. In some embodiments, where specifically stated, when a position is designated specifically as "H" or "hydrogen", the position incorporates ≤20% deuterium, ≤10% deuterium, ≤5% deuterium, ≤4% deuterium, ≤3% deuterium, ≤2% deuterium, or ≤1% deuterium. Also, unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium). The amount of deuterium incorporation at a designated position may be measured by analytical methods known to one of ordinary skill in the art, for example, by proton NMR.

The term "isotopic enrichment factor" as used herein means the ratio between the isotopic abundance and the natural abundance of a specified isotope.

In other embodiments, a deuterated compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), at least 6533.3 (98% deuterium incorporation) or at least 6633.3 (99.5% deuterium incorporation).

In some embodiments, in a compound of this invention, each designated deuterium position (or atom) has deuterium incorporation of at least 52.5%. In some embodiments, in a compound of this invention, each designated deuterium position has deuterium incorporation of at least 60%. In some embodiments, in a compound of this invention, each designated deuterium position has deuterium incorporation of at least 67.5%. In some embodiments, in a compound of this invention, each designated deuterium position has deuterium incorporation of at least 75%. In some embodiments, in a compound of this invention, each designated deuterium position has deuterium incorporation of at least 80%. In some embodiments, in a compound of this invention, each designated deuterium position has deuterium incorporation of at least 85%. In some embodiments, in a compound of this invention, each designated deuterium position has deuterium incorporation of at least 90%. In some embodiments, in a compound of this invention, each designated deuterium position has deuterium incorporation of at least 95%. In some embodiments, in a compound of this invention, each designated deuterium position has deuterium incorporation of at least 97%. In some embodiments, in a compound of this invention, each designated deuterium position has deuterium incorporation of at least 98%. In some embodiments, in a compound of this invention, each designated deuterium position has deuterium incorporation of at least 99%. In some embodiments, in a compound of this invention, each designated deuterium position has deuterium incorporation of at least 99.5%.

The term "isotopologue" refers to a species in which the chemical structure differs from any of the compounds described herein only in the isotopic composition thereof.

The term "compound," when referring to a deuterated compound of this invention, for example Compound I, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. In certain embodiments, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

As depicted above, Compound (I) is shown as a "free base". In some embodiments, a pharmaceutically acceptable salt of Compound (I) is used.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Pharmaceutically acceptable salts of Compound (I) include acid addition salts formed with inorganic acids or organic acids. Suitable inorganic acids include hydrochloric, hydrobromic, sulfuric and phosphoric acid. Suitable organic acids include paratoluenesulfonic, salicyclic, tartaric, ascorbic, maleic, besylic, fumaric, gluconic, glucuronic, formic, glutamic, methanesulfonic, ethanesulfonic, benzenesulfonic, lactic, oxalic, succinic, citric, benzoic and acetic acid. In certain embodiments, pharmaceutically acceptable salts of Compound (I) are selected from sulfate, phosphate, paratoluenesulfonate and methanesulfonate (mesylate) salts.

In certain embodiments, the pharmaceutically acceptable salt of Compound (I) is a phosphate salt. In a particular embodiment, a phosphate salt of Compound (I) (in a 1:1 molar ratio) is used. The phosphate salt of Compound (I) is depicted below:

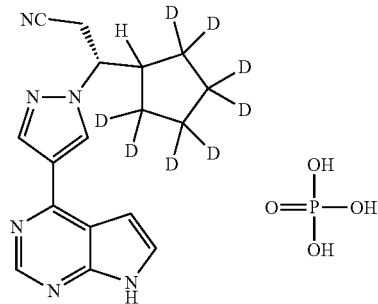 [SMILES: [2H]C1([2H])C([C@@H](CC#N)n2cc(-c3ncnc4[nH]ccc34)cn2)C([2H])([2H])C([2H])([2H])C1([2H])[2H] ; O=P(O)(O)O]

The molecular weight of Compound (I) is 314.2 g/mol. The molecular weight of the 1:1 phosphate salt of Compound (I) is 412.2 g/mol.

In an embodiment, the ratio of Compound I to phosphate in the salt form is about 1:1.

In one embodiment, any atom not designated as deuterium is present at its natural isotopic abundance in Compound (I), or a pharmaceutically acceptable salt thereof.

The pharmaceutically acceptable salt of Compound (I) may be present as a hydrate, solvate or in anhydrous form. In certain embodiments, the pharmaceutically acceptable salt is anhydrous. In a more specific embodiment, the phosphate salt is anhydrous.

Throughout the specification, unless specified otherwise, references to the amount of Compound (I) will be understood to refer to the amount of the parent compound on a free base basis, even if the compound is present as a salt of Compound I.

Purely by way of example, reference to 12 mg of Compound (I) or a salt thereof, will be understood to refer to 12 mg of the free base, or a salt of Compound (I) with 12 mg of free base equivalent. In the context of the anhydrous mono-phosphate salt of Compound (I), about 15.7 mg of the salt delivers 12 mg of Compound (I) (free base equivalent).

In certain embodiments, the amount of Compound (I), or a pharmaceutically acceptable salt thereof administered in the method for inducing hair growth is about 8 mg (such as 8 mg) twice per day or 16 mg/day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for inducing hair growth is about 12 mg (such as 12 mg) twice per day or 24 mg per day. In a specific embodiment, Compound (I) is administered as about 15.7 mg (such as 15.7 mg) of the phosphate salt of Compound (I) twice per day.

Dosing and Administration of JAK Inhibitors and Compound (I)

The term "treat" means decrease, suppress, attenuate, diminish, arrest, or stabilize the development or progression of a disease (e.g., a disease or disorder delineated herein), lessen the severity of the disease or improve the symptoms associated with the disease. For example, treatment of a hair loss disorder includes regrowth of hair, prevention of further hair loss, or diminishing the rate of hair loss.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like). The terms subject and patient are used interchangeably herein. In a particular embodiment, the subject or patient is a human. In an even more particular embodiment, the subject or patient is an adult human. In another even more particular embodiment, the subject is an adolescent human (12 years to less than 18 years). In another even more particular embodiment, the subject is a pediatric human (6 years to less than 12 years).

As used here, "patient population" or "population of subjects" refers to a pre-determined group of subjects. For example, the patient population or population of subjects can be the subjects that are receiving treatment at or around the same time and are being monitored and assessed together. For example, the patient population or population of subjects can be the members of a clinical trial.

As used herein, a "therapeutically effective amount" is an amount sufficient to treat the target condition or disorder. Where a drug has been approved by the U.S. Food and Drug Administration (FDA), a "therapeutically effective amount" can be the dosage approved by the FDA.

In certain embodiments, the amount of Compound (I), or a pharmaceutically acceptable salt thereof administered in the method for treating hair loss disorders, is about 8 mg/day (such as 8 mg/day), about 16 mg/day (such as 16 mg/day), about 24 mg/day (such as 24 mg/day), or about 32 mg/day (such as 32 mg/day). In more particular embodiments, the amount of Compound (I), or a pharmaceutically acceptable salt thereof administered in the method for treating hair loss disorders, is about 8 mg/day (such as 8 mg/day), about 16 mg/day (such as 16 mg/day) or about 24 mg/day (such as 24 mg/day).

In certain embodiments, the amount of Compound (I), or a pharmaceutically acceptable salt thereof administered in the method for treating hair loss disorders is about 4 mg (such as 4 mg) twice per day. In a specific embodiment, Compound (I) is administered as about 5.3 mg (such as 5.3 mg) of the phosphate salt of Compound (I) twice per day.

In other embodiments, the amount of Compound (I), or a pharmaceutically acceptable salt thereof administered in the method for treating hair loss disorders is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for treating hair loss disorders is about 12 mg (such as 12 mg) twice per day. In a specific embodiment, Compound (I) is administered as about 15.8 mg (such as 15.8 mg) of the phosphate salt of Compound (I) twice per day.

In certain embodiments, the amount of Compound (I), or a pharmaceutically acceptable salt thereof administered in the method for treating hair loss disorders is about 16 mg (such as 16 mg) twice per day. In a specific embodiment, Compound (I) is administered as about 21.1 mg (such as 21.1 mg) of the phosphate salt of Compound (I) twice per day.

In a particular embodiment, the hair loss disorder is alopecia areata.

In certain embodiments, the subject is a human. In a specific embodiment, the subject is an adult human (e.g., a human that is 18 years of age or older). In another specific embodiment, the subject is an adolescent human (e.g., a human that is 12 years to less than 18 years of age). In another specific embodiment, the subject is a pediatric human (e.g., a human that is 6 years to less than 12 years of age).

In a specific embodiment, Compound (I), or a pharmaceutically acceptable salt thereof (such as the phosphate salt), is administered orally at any of the dosages described herein. In an even more specific embodiment, the Compound (I), or a pharmaceutically acceptable salt thereof, is administered orally at any of the dosages described herein in a pharmaceutical formulation which is a tablet.

In certain embodiments, a therapeutically effective amount of the JAK inhibitor is administered once or twice per day, wherein the amount of the JAK inhibitor is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of the JAK inhibitor is about 4 mg/day, 8 mg/day, 16 mg/day, 32 mg/day or 48 mg/day. In a particular embodiment, the JAK inhibitor is administered orally at any of the foregoing dosages. In another particular embodiment, the JAK inhibitor is administered orally at any of the foregoing dosages in a pharmaceutical formulation which is a tablet.

In still another particular embodiment, the tablet is a coated tablet comprising the following ingredients as found in Table 1:

TABLE 1

8 mg strength deuruxolitinib tablet (contains equivalent of 8 mg free based euruxolitinib).

| Component | Wt % | Amount (mg) |
| --- | --- | --- |
| Deuruxolitinib phosphate | 8.75 | 10.5 |
| Microcrystalline cellulose (intragranular) | 33.25 | 39.90 |
| Microcrystalline cellulose (extragranular) | 19 | 22.80 |
| Lactose monohydrate | 30 | 36.00 |
| Polyvinylpyrrolidone | 5 | 6.00 |
| Hydroxypropyl cellulose | 3 | 3.60 |
| Colloidal silicon dioxide | 0.5 | 0.60 |
| Magnesium stearate | 0.5 | 0.60 |
| Purified water | As required | As required |
| Total (tablet core) | 100 | 120 |
| Opadry ® amb II | | 3.60 |
| Total (coated tablet) | | 123.6 |

In such embodiments, the total weight of the tablet core is about 120 mg and the dose of deuruxolitinib phosphate is the equivalent of 8 mg free base. In some embodiments, the tablet is coated with, for example, 3.60 mg Opadry® amb II coating. In some embodiments, the tablet film coating contains the following excipients: carmine, FD&C blue #2 aluminum lake, glyceryl mono and dicaprylocaprate, polyvinyl alcohol, sodium lauryl sulfate, talc, and titanium dioxide.

Tablets can be prepared by a variety of techniques, some of which are known in the art. In some embodiments, a tablet oral dosage forms as described can be prepared by (a) combining deuruxolitinib phosphate, microcrystalline cellulose, lactose monohydrate, hydroxypropyl cellulose, and polyvinylpyrrolidone; (b) wet granulating the combination of (a) to form particles; (c) blending the particles formed with microcrystalline cellulose, colloidal silicon dioxide and magnesium stearate to form a blend; and (d) compressing the blend into a tablet. In some embodiments, the tablet is coated to provide a coated tablet comprising a tablet core and an outer coating layer.

Patient Assessments i. ALC, ANC and Hemoglobin Levels from a Complete Blood Count A complete blood count (CBC) is a blood test. It's used to look at overall health and find a wide range of conditions, including anemia, infection and leukemia. A complete blood count test measures the following: Red blood cells, which carry oxygen; White blood cells, which fight infection; Hemoglobin, the oxygen-carrying protein in red blood cells; Hematocrit, the amount of red blood cells in the blood; Platelets, which help blood to clot.

Absolute lymphocyte count (ALC) is representative of the number of lymphocytes in a certain volume of blood and is part of a complete blood count.

The absolute neutrophil count (ANC) is an estimate of the body's ability to fight infections, especially bacterial infections. These test results are often referred to as a patient's "counts." An ANC measures the number of neutrophils in the blood. Neutrophils are a type of white blood cell that kills bacteria.

A hemoglobin test measures the amount of hemoglobin in the blood. Hemoglobin is a protein in the red blood cells that carries oxygen to the body's organs and tissues and transports carbon dioxide from the organs and tissues back to the lungs.

In a specific embodiment, complete blood count of the patient/subject being treated shows that the ALC is ≥500 cells/µl, the ANC is ≥1000 cells/µl and/or the Hemoglobin level is ≥8 g/dl. In a further embodiment, the patient/subject's ALC, ANC and Hemoglobin levels are monitored at 4, 8, 12, 16, 20 and 24 weeks following the onset of treatment. In yet another embodiment, treatment of the patient/subject is interrupted if the ALC is <500 cells/µl, the ANC is <1000 cells/µl and/or the Hemoglobin level is <8 g/dl, ii. SALT Score The efficacy of treatment of hair loss disorders such as alopecia areata can be measured in a variety of ways, some of which are known in the art. For example, the "severity of alopecia tool", otherwise known as SALT, is a validated assessment scale-developed by the National Alopecia Areata Foundation working committee—to evaluate the degree of hair loss. See, e.g., Olsen E A, Hordinsky M K, Price V H, et al. Alopecia areata investigational assessment guidelines-Part II. J Am Acad Dermatol 2004:51:440-447 and King B A, et al. Defining Severity in Alopecia Areata: Current Perspectives and a Multidimensional Framework (the contents of which are incorporated herein by reference).

The SALT score is calculated for a patient/subject by measuring the percentage of hair loss in each of the 4 areas of the scalp and adding the total to achieve a composite score (referred to herein as an absolute SALT score). Hair regrowth is reflected by a decrease in the SALT score. For example, no hair on the scalp would have a SALT score of 100 (i.e., an absolute SALT score) while complete hair regrowth would be a SALT score of 0 (i.e., an absolute SALT score).

In one embodiment, the patient/subject has an absolute SALT score of greater than or equal to 50 (i.e., absolute SALT score of ≥50) at onset of treatment. The absolute SALT score at the onset of treatment is referred to as the baseline SALT Score.

In one specific embodiment, the patient/subject's SALT score at the onset of treatment is an absolute SALT score of ≥50

In another embodiment, the patient/subject has an absolute SALT score of greater than or equal to 60 (i.e., absolute SALT score of ≥60), greater than or equal to 70 (i.e., absolute SALT score of ≥70), greater than or equal to 80 (i.e., absolute SALT score of ≥80), greater than or equal to 90 (i.e., absolute SALT score of ≥90) or greater than or equal to 95 (i.e., absolute SALT score of ≥95) at onset of treatment.

In some embodiments, the absolute SALT score can be used to define categories of hair loss. For example, Wyrwich et al. (Wyrwich K W, et al. The alopecia areata investigator global assessment scale: a measure for evaluating clinically meaningful success in clinical trials. Br J Dermaol. 2020; 183:702-9) describe severity of hair loss as: no hair loss 0% hair loss; limited hair loss=1-20% hair loss; moderate hair loss=21-49% hair loss; severe hair loss=50-94% hair loss; and very severe hair loss=95-100% hair loss.

In certain embodiments, methods of treatment as described herein can provide a reduction in the absolute SALT score of at least 10 points after treatment (for example, from a SALT score of 100 prior to treatment to a SALT score of 90 after treatment). In further embodiments, methods of treatment as described herein can provide a SALT score reduction of at least 20 points, 30 points, 40 points, 50 points, 60 points, 70 points, 80 points, 90 points, or 100 points.

In other embodiments, the method of treatment described herein can provide an absolute SALT score of ≤20 (i.e., less than or equal to 20% scalp hair loss) for the subject/patient following treatment. For example, after 12 weeks of the treatment described herein the subject has an absolute SALT score of ≤20, or after 16 weeks of the treatment described herein the subject has absolute SALT score of ≤20, or after 20 weeks of the treatment described herein the subject has absolute SALT score of ≤20, or after 24 weeks of the treatment described herein the subject has absolute SALT score of ≤20, or after 52 weeks of the treatment described herein the subject has absolute SALT score of ≤20.

In further embodiments, the method of treatment described herein can provide an absolute SALT score of ≤10 (i.e., less than or equal to 10% scalp hair loss) for the subject/patient following treatment. For example, after 12 weeks of the treatment described herein the subject has an absolute SALT score of ≤10, or after 16 weeks of the treatment described herein the subject has absolute SALT score of ≤10, or after 20 weeks of the treatment described herein the subject has absolute SALT score of ≤10, or after 24 weeks of the treatment described herein the subject has absolute SALT score of ≤10, or after 52 weeks of the treatment described herein the subject has absolute SALT score of ≤10.

In certain embodiments, methods of treatment as described herein can provide after treatment at least a 20% reduction from baseline (prior to treatment) in the patient's/subject's SALT score, or at least a 30% reduction from baseline in the patient's/subject's SALT score, or at least a 40% reduction from baseline in the patient's/subject's SALT score, or at least a 50% reduction from baseline in the patient's/subject's SALT score, or at least a 60% reduction from baseline in the patient's/subject's SALT score, or at least a 70% reduction (e.g., a 75% reduction) from baseline in the patient's/subject's SALT score, or at least a 80% reduction from baseline in the patient's/subject's SALT score, or at least a 90% reduction from baseline in the patient's/subject's SALT score. Such % reductions in SALT score are referred to herein as a % relative reductions in SALT score.

In specific embodiments, after 12 weeks of treatment the subject has at least a 75% relative reduction in SALT score.

In certain embodiments, treatment is continued for a period of at least four weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In some embodiments, the disclosure provides a method of treating alopecia areata in a subject in need thereof, wherein the proportion of participants achieving SALT ≤20 continues to increase for at least 54 weeks, at least 68 weeks, or at least 76 weeks when administered Compound (I) as described herein. In some embodiments, the disclosure provides a method of treating alopecia areata in a subject in need thereof, wherein the rate of increase in the proportion of participants achieving SALT ≤20 does not decrease greater than 30%, greater than 40%, greater than 50%, or greater than 60% in a 4 week period for at least 48 weeks, at least 54 weeks, at least 68 weeks, or at least 76 weeks.

iii. Hospital Anxiety and Depression Scale

The Hospital Anxiety and Depression Scale (HADS) is used to measure anxiety and depression in a general medical population of subjects. HADS comprises of 14 items (7 items each for anxiety and depression), with a score ranging between 0 and 21 for the anxiety and depression subscales. Scores between 8 and 10 indicate a moderate presence of symptoms of anxiety and depression, whereas a score greater than 11 indicates a significant number of symptoms of anxiety and depression that likely correspond with a clinical diagnosis. The total HADS score may be regarded as a global measure of psychological distress (Roberts et al, 2001; Johnston et al, 2000). A negative change in a subject's HADS score from a starting timepoint to an end point during treatment, e.g. from baseline to Week 24 of treatment, indicates an improvement in symptoms of anxiety and depression. The HADS questionnaire was completed by subjects at baseline and Week 24. The term "baseline" as used herein refers to the HADS score (or HADS-A or HADS-D score) determined before administration of Compound (I).

In yet another embodiment, the patient/subject reports a point change (reduction) of at least 1.0 point in overall score from baseline on the HADS scale after 12 weeks of treatment with 8 mg twice per day. In a specific embodiment, the point change (reduction) in overall score is 3.0 points after 12 weeks of treatment with 8 mg twice per day. In yet another embodiment, the patient/subject reports a point change (reduction) of at least 2.0 point in overall score from baseline on the HADS scale after 16 weeks of treatment with 8 mg twice per day. In a specific embodiment, the point change (reduction) in overall score is 4.0 points after 16 weeks of treatment with 8 mg twice per day. In yet another embodiment, the patient/subject reports a point change (reduction) of at least 6.0 point in overall score from baseline on the HADS scale after 24 weeks of treatment with 8 mg twice per day. In a specific embodiment, the point change (reduction) in overall score is 10.0 points after 24 weeks of treatment with 8 mg twice per day.

In yet another embodiment, the patient/subject reports a point change (reduction) of at least 1.0 point in Hospital Anxiety and Depression Scale-Anxiety (HADS-A) subscale score from baseline on the HADS scale after 12 weeks of treatment with 8 mg twice per day. In a specific embodiment, the point change (reduction) in the HADS-A subscale is 2.0 points after 12 weeks of treatment with 8 mg twice per day. In yet another embodiment, the patient/subject reports a point change (reduction) of at least 2.0 point in overall score from baseline on the HADS-A subscale after 16 weeks of treatment with 8 mg twice per day. In a specific embodiment, the point change (reduction) in the HADS-A subscale is 3.0 points after 16 weeks of treatment with 8 mg twice per day. In yet another embodiment, the patient/subject reports a point change (reduction) in the HADS-A subscale of at least 4.0 point in overall score from baseline on the HADS scale after 24 weeks of treatment with 8 mg twice per day. In a specific embodiment, the point change (reduction) in the HADS-A subscale is 6.0 points after 24 weeks of treatment with 8 mg twice per day.

In yet another embodiment, the patient/subject reports a point change (reduction) of at least 1.0 point in Hospital Anxiety and Depression Scale-Depression (HADS-D) subscale score from baseline on the HADS scale after 12 weeks of treatment with 8 mg twice per day. In a specific embodiment, the point change (reduction) in the HADS-D subscale is 2.0 points after 12 weeks of treatment with 8 mg twice per day. In yet another embodiment, the patient/subject reports a point change (reduction) of at least 2.0 point in overall score from baseline on the HADS-D subscale after 16 weeks of treatment with 8 mg twice per day. In a specific embodiment, the point change (reduction) in the HADS-D subscale is 3.0 points after 16 weeks of treatment with 8 mg twice per day. In yet another embodiment, the patient/subject reports a point change (reduction) in the HADS-D subscale of at least 3.0 point in overall score from baseline on the HADS scale after 24 weeks of treatment with 8 mg twice per day. In a specific embodiment, the point change (reduction) in the HADS-D subscale is 5.0 points after 24 weeks of treatment with 8 mg twice per day.

iv. Hair Satisfaction and Hair Quality Patient Reported Outcomes

The SPRO is a single-item questionnaire answered by the subject and designed to measure how satisfied Alopecia Areata subjects are with their hair at the time of the assessment. Subjects answer questions on a scale of 1 to 5, representing "Very satisfied" to "Very dissatisfied." Satisfaction categories 1-5 of the scale were defined as follows: 1="Very Satisfied"; 2="Satisfied"; 3="Neither Satisfied nor Dissatisfied"; 4=Dissatisfied"; and 5="Very Dissatisfied".

The results of the SPRO was analyzed in three different ways: 1) the percentage of responders, 2) the change from baseline, and 3) the percentage of subjects achieving a ≥2.0 point change from baseline.

In certain embodiments, the patient/subject reports "Satisfied" or "Very Satisfied" on the SPRO scale following 24 weeks of treatment. In a further embodiment, the patient/subject reports "Satisfied" or "Very Satisfied" on the SPRO scale following 12 weeks of treatment.

In certain embodiments, at least 30% of patient/subjects responded to the SPRO following 24 weeks of treatment with 8 mg of Compound I administered twice per day. In certain embodiments, at least 40% of patient/subjects responded to the SPRO following 24 weeks of treatment with 8 mg of Compound I administered twice per day. In certain embodiments, at least 40% of patient/subjects responded to the SPRO following 24 weeks of treatment with 12 mg of Compound I administered twice per day. In certain embodiments, at least 50% of patient/subjects responded to the SPRO following 24 weeks of treatment with 12 mg of Compound I administered twice per day. In certain embodiments, there is an increase of at least 30% in patient/subjects who responded to the SPRO following 24 weeks of treatment with 8 mg of Compound I administered twice per day as compared to patients/subjects who received treatment with the placebo. In certain embodiments, there is an increase of at least 40% in patient/subjects who responded to the SPRO following 24 weeks of treatment with 8 mg of Compound I administered twice per day as compared to patients/subjects who received treatment with the placebo. In certain embodiments, there is an increase of at least 40% in patient/subjects who responded to the SPRO following 24 weeks of treatment with 12 mg of Compound I administered twice per day as compared to patients/subjects who received treatment with the placebo. In certain embodiments, there is an increase of at least 50% in patient/subjects who responded to the SPRO following 24 weeks of treatment with 12 mg of Compound I administered twice per day as compared to patients/subjects who received treatment with the placebo.

In yet another embodiment, the patient/subject reports a point change (reduction) of at least 1.5 from baseline on the SPRO scale. In a specific embodiment, the point change (reduction) is greater than or equal to 2 (i.e., the point change (reduction) is ≥2.

v. Global Impression Scales

The Global Impression Scales employ a 7-point Likert scale (with 1 being better and 7 being worse) measuring either disease state severity or improvement after treatment.

a. Clinical Global Impression of Improvement (CGI-I)

The CGI-I was assessed by the investigator. Compared to the subject's alopecia areata prior to treatment at baseline, the subject's current state of alopecia areata was assessed according to the investigator's perceived change. The investigator selected 1 of 7 numeric choices representing "Very Much Worse" to "Very Much Improved." To reduce variability, 1 rater was to perform the CGI-I assessment for the subject for the duration of the study. The definition of the numeric choices is as follows: 1=very much improved since the initiation of treatment; 2=much improved; 3=minimally improved; 4=no change from baseline (the initiation of treatment); 5=minimally worse; 6=much worse; 7=very much worse since the initiation of treatment.

In certain embodiments, the patient/subject reports "much improved" or "very much improved" on the CGI-I scale following 24 weeks of treatment. In a further embodiment, the patient/subject reports "much improved" or "very much improved" on the CGI-I scale following 20 weeks of treatment. In yet another embodiment, the patient/subject reports "much improved" or "very much improved" on the CGI-I scale following 16 weeks of treatment. In yet another embodiment, the patient/subject reports "much improved" or "very much improved" on the CGI-I scale following 12 weeks of treatment.

b. Patient Global Impression of Improvement

The PGI-I was assessed by the subject. Compared to the subject's AA prior to treatment at baseline, the subject's current state of AA was assessed according to his/her perceived change. The subject selected 1 of 7 numeric choices representing "Very Much Worse" to "Very Much Improved." If a subject was unable to attend an in-person clinic visit due to COVID-19, the PGI-I was to be performed via a virtual visit with video capability. The definitions of the numeric choices is as follows: 1=very much improved; 2=much improved; 3=minimally improved; 4=no change; 5=minimally worse; 6=much worse; and 7=very much worse.

In certain embodiments, the patient/subject reports "much improved" or "very much improved" on the PGI-I scale following 24 weeks of treatment. In a further embodiment, the patient/subject reports "much improved" or "very much improved" on the PGI-I scale following 20 weeks of treatment. In yet another embodiment, the patient/subject reports "much improved" or "very much improved" on the PGI-I scale following 16 weeks of treatment. In yet another embodiment, the patient/subject reports "much improved" or "very much improved" on the PGI-I scale following 12 weeks of treatment.

In yet another embodiment, the patient/subject reports a point change (reduction) of at least 1.5 from baseline on the PGI-I scale after 12 weeks of treatment. In a specific embodiment, the point change (reduction) is at least 1.7 after 16 weeks of treatment. In another specific embodiment, the point change (reduction) is at least 2.1 after 24 weeks of treatment.

c. Clinical Global Impression of Severity

The CGI-S was assessed by the investigator and considered the severity of the subject's alopecia at the time of assessment. The investigator selected 1 of 7 numeric choices representing "Among the most extreme hair loss" to "Normal, no hair loss." To reduce variability, 1 rater was to perform the CGI-S assessment for the subject. The definitions of the numeric choices is as follows: 1=normal, no hair loss; 2=borderline hair loss; 3=mild hair loss; 4=moderately hair loss; 5=marked hair loss; 6=severe hair loss; 7=among the most extreme hair loss.

In a certain embodiment, the patient/subject reports a point change (reduction) of at least 1.0 from baseline on the CGI-S scale after 12 weeks of treatment. In a specific embodiment, the point change (reduction) is at least 1.5 after 16 weeks of treatment. In another specific embodiment, the point change (reduction) is at least 2.0 after 24 weeks of treatment.

d. Patient Global Impression of Severity

The PGI-S was assessed by the subject and considered the severity of his/her alopecia areata at the time of assessment. The subject selected 1 of 7 numeric choices representing "Among the most extreme hair loss" to "Normal, no hair loss." The definitions of the numeric choices is as follows: 1=normal, no hair loss; 2=borderline hair loss; 3=mild hair loss; 4=moderately hair loss; 5=marked hair loss; 6=severe hair loss; 7=among the most extreme hair loss.

In certain embodiments, the patient/subject reports a point change (reduction) of at least 1.5 from baseline on the PGI-S scale after 12 weeks of treatment. In a specific embodiment, the point change (reduction) is at least 1.7 after 16 weeks of treatment. In another specific embodiment, the point change (reduction) is at least 2.1 after 24 weeks of treatment.

vi. Brigham Eyebrow Tool for Alopecia (BETA)

The BETA is a clinician-rated scale developed by dermatologists at Brigham and Women's Hospital that assesses the total eyebrow hair present (Tkachenko, E, et al., Brigham Eyebrow Tool for Alopecia: A Reliable Assessment of Eyebrow Alopecia Areata, Journal of Investigative Dermatology Symposium Proceedings (2020) 20, S41-S44). The BETA is calculated based on hair density (range 0 to 3) and surface area of each individual eyebrow. The BETA score is the sum of the right and left eyebrow scores (range 0 (absent) to 6). An expert panel of certified raters at Brigham and Women's Hospital performed central readings based on photographs of the eyebrows provided by the study sites and determined a score for each subject with eyebrow involvement following each visit where an assessment of eyebrow hair presence was assessed. The BETA was performed at baseline, Week 12, and Week 24. If a subject was unable to attend an in-person clinic visit due to COVID-19, the BETA may not have been performed due to the inability to take photographs of the eyebrows.

In certain embodiments, a point change (increase) of at least 1.0 from baseline is achieved by the patient/subject on the BETA after 24 weeks of treatment.

In another embodiment, a point change (increase) of at least 0.5 from baseline is achieved by the patient/subject being treated on the BETA after 12 weeks of treatment.

vii. Brigham Eyelash Tool for Alopecia (BELA)

The BELA is a clinician-rated scale developed by dermatologists at Brigham and Women's Hospital that assesses the total eyelash hair present Manjaly, P. et al., Development and validation of the Brigham Eyelash Tool for Alopecia (BELA): A measure of eyelash alopecia areata, J Am Acad Dermatol (2021) 1-2. The BELA is calculated based on grade values (range 0 to 3) and distribution. The BELA score is the sum of the individual scores for the left and right eyes (range 0 (absent) to 6). The same expert panel of certified raters at Brigham and Women's Hospital who performed the BETA assessment also performed central readings based on photographs of the eyelashes and determined a score for each subject with eyelash involvement following each visit where an assessment of eyelash hair presence was assessed. The BELA was performed at baseline, Week 12, and Week 24. If a subject was unable to attend an in-person clinic visit due to COVID-19, the BELA may not have been performed due to the inability to take photographs of the eyelashes.

In certain embodiments, a point change (increase) of at least 1.0 from baseline is achieved by the patient/subject on the BELA after 24 weeks of treatment.

In another embodiment, a point change (increase) of at least 0.5 from baseline is achieved by the patient/subject being treated on the BELA after 12 weeks of treatment.

viii. eGFR Levels

Glomeruli are tiny filters in your kidneys that help remove toxins from your blood. Estimated glomerular filtration rate (eGFR) measures how much blood these filters clean every minute based on your body size. eGFR is used to monitor subjects for the onset of kidney disease.

Tests to precisely measure GFR are highly complex. For this reason, such tests typically only take place for research or transplant purposes. Instead, a formula to come up with an estimated GFR (eGFR) is used in practice. The formula combines results from a serum creatinine blood test with other information.

A serum creatinine blood test measures levels of creatinine. Your body makes and uses creatine to provide energy to muscles. When muscles use this energy, muscle tissue breaks down, releasing creatinine (a toxin) into the blood. Healthy kidneys filter this toxin out of the blood and your body gets rid of it when you urinate. But when you have kidney disease, creatinine stays in the blood and gradually builds up.

eGFR levels can be determined using the following equation:

MDRD Equation: GFR (ml/min/1.73 m$^2$)=186×(SCR)$^{-1.154}$×(Age)$^{-1.154}$×Factor Factor is 0.742 (female) and 1.210 (African American)
$S_{cr}$ (standardized serum creatinine)=mg/dL
age=years Classification of renal function based on FDA and EMA guidances[8,9]

| Stage | Description | Renal function (eGFR) (mL/min)[a,b] | GFR (mL/min)[d] |
|---|---|---|---|
| 1 | Control (normal renal function) | ≥90 | ≥90 |
| 2 | Mild impairment | 60-89 | 60 to <90 |
| 3 | Moderate impairment | 30-59 | 30 to <60 |
| 4 | Severe impairment | 15-29 | <30 (dialysis not required) |
| 5 | Kidney failure [a, c]; ESRD[d] | <15 or dialysis subjects on non-dialysis days | <15 requiring dialysis |

Abbreviations:
EMA, European Medicines Agency;
ESRD, end-stage renal disease;
FDA, US Food and Drug Administration;
GFR, glomerular filtration rate.
[a] As stated in the FDA guidance.
[b] Estimate of GFR based on an estimation equation and expressed in ml/min. To convert ml/min/1.73 m$^2$ to ml/min multiply by the individual's body surface area calculated using an appropriate formula and divide by 1.73.
[c] This classification is strictly for the purposes of conducting a dedicated renal impairment study and should not be used for the purposes of classifying kidney disease.
[d] As stated in the EMA guidance.
References
[8] Food and Drug Administration, Center for Drug Evaluation and Research. Pharmacokinetics in patients with impaired renal function-study design, data analysis, and impact on dosing. https://www.fda.gov/media/78573/download Cited (2020). Accessed Nov. 4, 2020.
[9] European Medicines Agency. Guideline on the evaluation of the pharmacokinetics of medicinal products in patients with decreased renal function. https://www.ema.europa.eu/en/documents/scien tific-guideline/guideline-evaluation-pharmacokinetics-medicinal-products-patients-decreased-renal-function_en.pdf Cited (2015). Accessed Aug. 27, 2020.

Based on the above table, subjects with moderate renal impairment are those having an eGFR of 30-59 mL/min. Similarly subjects with normal kidney function are those with an eGFR of ≥90 mL/min. All other categories of kidney disease (impairment) can be determined with reference to the table above.

For all embodiments described herein where eGFR is expressed as mL/min MDRD, there are corresponding embodiments, wherein eGFR is expressed as mL/min/1.73 m$^2$ or mL/min.

EXEMPLIFICATION

Example 1—Renal Impairment Study

A study was conducted to determine the effect of moderate renal impairment on the PK of CTP-543 and its 2 most abundant metabolites in humans (C-21714 and C-21717) following administration of a single 12 mg oral dose of CTP-543. The secondary objectives of this study was to evaluate the safety and tolerability of a single 12 mg oral dose of CTP-543 in subjects with moderate renal impairment and subjects with normal renal function. The study enrolled 8 subjects in the normal renal function cohort, and 8 subjects in the moderate impaired renal function cohort.

The primary endpoint of this study was single dose PK exposure parameters: Cmax, $AUC_{(0-Tlast)}$, and $AUC_{(0-\infty)}$.

The secondary endpoints of this study were:
Adverse Events, clinical laboratory findings, physical examinations, ECGs, and vital signs.
Other PK parameters, such as, but not limited to: $T_{max}$, $\lambda_z$, $t_{1/2}$, CL/F, and $V_z$/F.

All subjects had samples collected for PK. Blood samples were collected pre-dose and at 0.25, 0.5, 0.75, 1, 1.5, 2, 2.5, 3, 4, 6, 8, 12, 18, 24, 36, and 48 hours after CTP-543 dosing. All subjects had samples collected to assess plasma protein binding of CTP-543 at 2 hours post-dose.

All plasma CTP-543, C-21714, and C-21717 PK parameter calculations were performed using actual times in hours. PK parameters were determined using non-compartmental analysis (NCA) methods based on individual plasma concentration-time data for all PK analytes.

A summary of CTP-543 PK parameters of the PK population with outlier excluded following a single oral administration of 12 mg CTP-543 is presented in Table 2. Geometric mean $C_{max}$, $AUC_{0-Tlast}$, and $AUC_{0-inf}$ were 199 ng/mL, 836 h·ng/mL, and 843 h·ng/mL, respectively, in subjects with normal renal function. Geometric mean $C_{max}$, $AUC_{0-Tlast}$, and $AUC_{0-inf}$ were 207 ng/ml, 1040 h·ng/mL, and 1050 h·ng/mL, respectively, in subjects with moderate renal impairment (Table 2)

TABLE 2

Geometric Mean Summary CTP-543 Pharmacokinetic Parameters-PK Population with Outlier Excluded

| Parameter | Units | Normal Renal Function N = 8 Geometric Mean (Geometric CV %) | Moderate Renal Impairment N = 7 |
|---|---|---|---|
| $AUC_{0-Tlast}$ | h · ng/mL | 836 (20.9) | 1040 (41.6) |
| $AUC_{0-inf}$ | h · ng/mL | 843 (20.6) | 1050 (41.6) |
| $C_{max}$ | ng/mL | 199 (21.4) | 207 (38.4) |
| $T_{max}^a$ | h | 0.71 [0.25-1.00] | 0.50 10.25-3.00] |
| $C_{last}$ | ng/mL | 0.898 (116.3) | 0.977 (45.2) |
| $\lambda_z$ | l/h | 0.166 (31.7) | 0.159 (31.7) |
| $t_{1/2}$ | h | 4.17 (31.7) | 4.36 (31.7) |
| CL/F | L/h | 14.2 (20.0) | 11.3 (41.6) |
| $V_s/F$ | L | 85.6 (27.9) | 72.1 (30.2) |

Abbreviations:
$\lambda_z$ = apparent terminal rate constant;
AUC = area under the concentration-time curve;
$AUC_{0-last}$ = AUC from time 0 extrapolated to infinity;
$AUC_{0-Time}$ = AUC from time 0 to the last quantifiable concentration;
$C_{last}$ = last observed (quantifiable) concentration;
$C_{max}$ = maximum observed concentration;
CL/F = clearance for parent only;
CV % = coefficient of variation;
max = maximum;
min-minimum;
N = total number of subjects;
PK = pharmacokinetics;
$t_{1/2}$ = terminal elimination half-life;
$T_{max}$ = time corresponding to occurrence of maximum observed concentration;
$V_s/F$ = volume of distribution for parent only PK exposure parameters of CTP-543 in subjects with normal renal function were compared to those in the moderate renal function impairment cohort, and the GMRs along with the 90% Confidence Intervals (CI) are presented in Table 3.

TABLE 3

Assessment of Moderate Renally Impaired Function Compared to Normal Renal Function for CTP-543-PK Population with Outlier Excluded

| Comparison | Parameter | Geometric Mean Ratio (%) | 90% CI (%) |
|---|---|---|---|
| Moderate versus normal | $AUC_{0-Tlast}$ (h · ng/mL) | 124.57 | 93.68, 165.64 |
| | $AUC_{0-inf}$ (h · ng/mL) | 124.31 | 93.58, 165.13 |
| | $C_{max}$ (ng/mL) | 103.96 | 79.28, 136.34 |

A summary of C-21714 and C-21717 PK parameters of the PK population with outlier excluded following a single oral administration of 12 mg CTP-543 is presented in Table 4 and Table 5, respectively.

Following a single oral administration of 12 mg CTP-543, the geometric mean metabolite-to-parent ratio values for C-21714's $C_{max}$ were 0.0362 and 0.0212, and C-21714's $AUC_{0-Tlast}$ were 0.157 and 0.0842 respectively for the normal renal function cohort and the moderate renal impairment cohort. (Table 4). The geometric mean metabolite-to-parent ratio values for C-21717's $C_{max}$ were 0.0433 and 0.0265, and C-21717's $AUC_{0-Tlast}$ were 0.133 and 0.0859 for the normal renal function cohort and the moderate renal impairment cohort, respectively. (Table 5).

TABLE 4

Geometric Mean Summary CTP-21714 Pharmacokinetic Parameters-PK Population with Outlier Excluded

| Parameter | Units | Normal Renal Function N = 8 Geometric Mean (Geometric CV %) | Moderate Renal Impairment N = 7 |
|---|---|---|---|
| $AUC_{0-Tlast}$ | h · ng/mL | 105 (41.2) | 69.9 (48.3) |
| $AUC_{0-inf}$ | h · ng/mL | 111 (43.7) | 75.4 (47.1) |
| $C_{max}$ | ng/mL | 5.75 (43.2) | 3.50 (67.9) |
| $T_{max}^a$ | h | 2.75 [0.75-12.00] | 8.00 [3.00-12.00] |
| $C_{last}$ | ng/mL | 0.344 (85.7) | 0.293 (60.7) |
| $\lambda_z$ | l/h | 0.0669 (32.7) | 0.0647 (24.5) |
| $T_{1/2}$ | h | 10.4 (32.7) | 10.7 (24.5) |
| M:P $AUC_{0-Tlast}$ | NA | 0.157 (37.3) | 0.0842 (32.3) |
| M:P $C_{max}$ | NA | 0.0362 (38.4) | 0.0212 (54.7) |

TABLE 5

Geometric Mean Summary CTP-21717 Pharmacokinetic Parameters-PK Population with Outlier Excluded

| Parameter | Units | Normal Renal Function N = 8 Geometric Mean (Geometric CV %) | Moderate Renal Impairment N = 7 |
|---|---|---|---|
| $AUC_{0-Tlast}$ | h · ng/mL | 88.2 (36.2) | 71.1 (44.0) |
| $AUC_{0-inf}$ | h · ng/mL | 90.3 (35.5) | 73.9 (42.9) |
| $C_{max}$ | ng/mL | 6.87 (38.2) | 4.36 (45.9) |
| $T_{max}^a$ | h | 2.00 [0.25-6.00] | 3.00 [0.50-6.00] |
| $C_{last}$ | ng/mL | 0.180 (30.6) | 0.191 (51.7) |
| $\lambda_z$ | l/h | 0.0955 (18.5) | 0.0871 (22.6) |
| $T_{1/2}$ | h | 7.26 (18.5) | 7.96 (22.6) |
| M:P $AUC_{0-Tlast}$ | NA | 0.133 (30.2) | 0.0859 (32.6) |
| M:P $C_{max}$ | NA | 0.0433 (32.9) | 0.0265 (39.4) |

PK exposure parameters of C-21714 and C-21717 in subjects with normal renal function were compared to those in the moderate renal function impairment cohort, and GMR along with the 90% CI are presented in Table 6.

TABLE 6

Assessment of Renally Impaired Function Compared to Normal Renal Function-PK Population with Outlier Excluded

| Comparison | Parameter | Geometric Mean Ratio (%) | 90% CI (%) |
|---|---|---|---|
| C-21714 | | | |
| Moderate versus normal | $AUC_{0-Tlast}$ (h · ng/mL) | 66.77 | 45.19, 98.66 |
| | $AUC_{0-inf}$ (h · ng/mL) | 67.67 | 45.55, 100.54 |
| | $C_{max}$ (ng · mL) | 60.89 | 37.92, 97.78 |
| C-21717 | | | |
| Moderate versus normal | $AUC_{0-Tlast}$ (h · ng/mL) | 80.69 | 56.70, 114.83 |
| | $AUC_{0-inf}$ (h · ng/mL) | 81.89 | 57.96, 115.68 |
| | $C_{max}$ (ng · mL) | 63.55 | 43.97, 91.83 |

Moderate renal impairment increased plasma CTP-543 AUC by approximately 24% compared to healthy control subjects, without altering $C_{max}$. Generally, the metabolite-to-parent ratios for C-21714 and for C-21717 were ≤0.2 for $C_{max}$ and AUC, for both cohorts. The healthy control subjects had higher metabolite-to-parent ratios as compared to the subjects with moderate renal impairment. There were no meaningful differences in the plasma protein binding of CTP-543 that were detected between cohorts of subjects with moderate renal impairment and matched control subjects with normal renal function.

Based on these results no dose adjustment is required in subjects with moderate renal impairment.

Subjects with moderate renal impairment are those subjects whose eGFR is in the range of 30-59 mL/min. Subjects with normal renal function are those subjects having an eGFR in the range of 90 mL/min.

Example 2

Phase III Trial

A Phase III trial was conducted to assess the efficacy and safety of CTP-543 in adult subjects with moderate to severe AA. Approximately 440 adult male and female subjects 18 to 65 years of age, inclusive, with moderate to severe AA participated in the study. Subjects with definitive diagnosis of AA, and at least 50% hair loss, as defined by a SALT score ≥50, who met all of the inclusion criteria and none of the exclusion criteria participated in the study.

The Screening Period lasted up to 28 days prior to initiation of study drug. The Treatment Period was a 24-week, double-blind, placebo-controlled period to define efficacy and safety for CTP-543. Subjects were randomized in a 1:2:1 ratio (CTP-543 12 mg BID: CTP-543 8 mg BID:placebo). Randomization was stratified by scalp hair loss into 1 of the following 2 categories: 1) partial scalp hair loss (SALT ≥50 and <95), 2) complete or near complete scalp hair loss (SALT ≥95).

Assessment of treatment response using SALT for efficacy occurred at 4, 8, 12, 16, 20 and 24 weeks.

The efficacy was determined based on the following primary and secondary end points.

Primary Efficacy Endpoint

The primary efficacy endpoint was the percentage of subjects achieving an absolute SALT score of ≤20.

Key Secondary Endpoints

The key secondary efficacy endpoints were the percentage of responders (defined as "satisfied" or "very satisfied") on the Hair Satisfaction Patient Reported Outcome (SPRO) scale at Week 24, 20, 16, 12, and 8.

Secondary Efficacy Endpoints

Additional secondary efficacy endpoints included the following:

Relative change in SALT scores from baseline at Weeks 4, 8, 12, 16, 20, and 24.

Percentage of responders (defined as "much improved" or "very much improved") using the Clinical Global Impression of Improvement (CGI-I) at Weeks 12, 16, 20, and 24.

Percentage of responders (defined as "much improved" or "very much improved") using the Patient Global Impression of Improvement (PGI-I) at Weeks 12, 16, 20, and 24.

Change from baseline in the Clinical Global Impression of Severity (CGI-S) at Weeks 12, 16, 20, and 24.

Change from baseline in the Patient Global Impression of Severity (PGI-S) at Weeks 12, 16, 20, and 24.

Change from baseline on the Brigham Eyebrow Tool for Alopecia (BETA) score at Weeks 12 and 24.

Change from baseline on the Brigham Eyelash Tool for Alopecia (BELA) score at Weeks 12 and 24.

Percentage of subjects achieving at least a 75% relative reduction in SALT score from baseline at Weeks 12 and 24.

Percentage of subjects achieving at least a 90% relative reduction in SALT score from baseline at Weeks 12 and 24.

Percentage of responders (defined as "satisfied" or "very satisfied") on the SPRO scale at Weeks 12, 16, and 20.

Change from baseline in the SPRO scale at Weeks 12, 16, 20, and 24.

Percentage of subjects achieving a ≥2-point change from baseline in the SPRO scale at Weeks 12, 16, 20, and 24.

Change from baseline on the individual items of the Hair Quality Patient Reported Outcome (QPRO) scale at Weeks 12, 16, 20, and 24.

Change from baseline in the depression scale of the Hospital Anxiety and Depression Scale (HADS) at Week 24.

Change from baseline in the anxiety scale of the HADS at Week 24.

Percentage of subjects achieving an absolute SALT score of ≤20 at Week 4.

Percentage of subjects achieving an absolute SALT score of ≤10 at Week 24

Inclusion Criteria:

Clinical presentation compatible with alopecia areata with a current episode lasting at least 6 months and not exceeding 10 years at the time of Screening. Total disease duration greater than 10 years is permitted.

At least 50% scalp hair loss, as defined by a Severity of Alopecia Tool (SALT) score ≥50, at Screening and Baseline.

Willing to comply with the study visits and requirements of the study protocol.

Exclusion Criteria:

Treatment with other medications or agents within 1 month of Baseline or during the study that may affect hair regrowth or immune response.

Active scalp inflammation, psoriasis, or seborrheic dermatitis requiring topical treatment to the scalp, significant trauma to the scalp, or other scalp condition that may interfere with the SALT assessment, or untreated actinic keratosis anywhere on the body at Screening and/or Baseline.

Treatment with systemic immunosuppressive medications within 3 months of Screening or during the study, or biologics within 6 months of Screening or during the study.

Screening labs outside the normal range for parameters associated with potential risk for treatment under investigation. This will include but is not limited to:
a. Platelets ≤100×109/L or ≥600×109/L
b. Absolute neutrophil count ≤1.5×109/L
c. Hemoglobin levels ≤10.5 g/dL for females, or hemoglobin levels ≤12.0 g/dL for males Screening blood level of hemoglobin A1c≥7.5% (58 mmol/mol, 9.3 mmol/L).

Abnormal renal function (estimated glomerular filtration rate <60 mL/min/1.73 m2 using the CKD-EPI 2009 equation at screening An example of a CKD-EPI 2009 equation can be: GFR=141× min $(Scr/\kappa, 1)^{\alpha}$×max $(Scr/\kappa, 1)^{-1.209}$×$0.993^{Age}$× 1.018 [if female]_1.159 [if black], where Scr is serum creatinine, κ is 0.7 for females and 0.9 for males, α is −0.329 for females and −0.411 for males, min indicates the minimum of Scr/κ or 1, and max indicates the maximum of Scr/κ or 1.

Females who are nursing, pregnant, or planning to become pregnant while in the study, and for 30 days after last dose of study drug.

Clinically significant medical condition, psychiatric disease, or social condition, as determined by the Investigator, that may unfavorably alter the risk-benefit of study participation, adversely affect study compliance, or confound interpretation of study results.

RESULTS:

Deuruxolitinib (a compound represented by Compound (I) described herein) has demonstrated significant improvements in hair regrowth vs placebo in two Phase 3 trials, THRIVE-AA1 and THRIVE-AA2.

The primary efficacy endpoint was the percentage of subjects achieving an absolute SALT score of ≤20 at week 24. At week 24, 33% of the subjects in the CTP-543 8 mg BID group, 38.3% of the subjects in the CTP-543 12 mg BID group and 0.8% of the subjects in the placebo group achieved a SALT score of ≤20. The percentage of subjects with an absolute SALT score of ≤20 at week 24 is presented graphically in FIG. 1.

Stratified by baseline scalp hair loss, 57/134 (42.5%), 50/88 (56.8%), and 1/55 (1.8%) of subjects with partial scalp hair loss in the 8 mg BID, 12 mg BID, and placebo groups, respectively, achieved SALT score ≤20 at Week 24, compared with 37/184 (20.1%), 33/112 (29.5), and 0/73 (0%) in subjects with complete or near-complete scalp hair loss.

Stratified by baseline scalp hair loss, 46/93 (54.1%), 27/48 (57.4%), and 1/48 (2.2%) of subjects with partial scalp hair loss in the 8 mg BID, 12 mg BID, and placebo groups, respectively, achieved SALT score ≤20 at Week 24, compared with 31/156 (20.9%), 19/79 (26.0), and 0/79 (0%) in subjects with complete or near-complete scalp hair loss.

Stratified by duration of current AA episode at screening, the percentages of participants with ≤4 years duration at week 24 were 38.3% (57/157), 44.0% (33/77), and 0% (0/80) for the 8 mg BID, 12 mg BID, and placebo groups, respectively, with values for those with >4 years duration being 23.8% (20/92), 28.9% (13/50), and 2.4% (1/47), respectively.

Hair Satisfaction Patient Reported Outcome Responders at Week 24

Figure 14A:
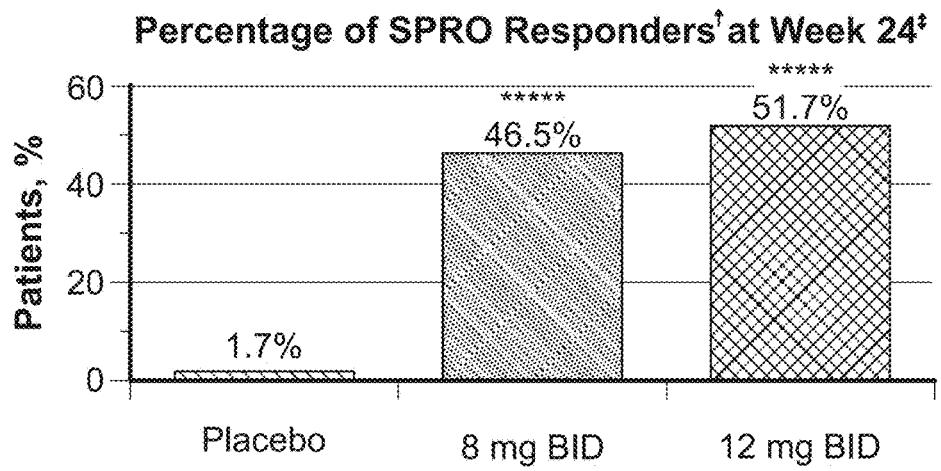
FIG. 14A is a graph showing the percentage of responders with responses of "very satisfied" or "satisfied" at week 24 of treatment with placebo, 8 mg BID, or 12 mg BID.

Responders were subjects with responses of "very satisfied" or "satisfied." At Week 24, the proportion of SPRO responders, based on subjects with non-missing data, was 46.5% of CTP-543 8 mg BID subjects, 51.7& of CTP-543 12 mg BID subjects, and 1.7% of placebo subjects (Table 7 and FIG. 14A).

TABLE 7

Key Secondary Endpoint: Mantel-Haenszel Common Risk Difference Analysis of Satisfaction of Hair Patient Reported Outcome (SPRO) Responders at Week 24 (MI with MAR Assumption) (Population: Efficacy Population)

| Visit<br>Endpoint<br>Statistic | Placebo<br>(N = 127) | CTP-543<br>8 mg BID<br>(N = 249) | CTF-543<br>12 mg BID<br>(N = 127) |
|---|---|---|---|
| Week 24 | | | |
| SPRO Responses[1], n (%) | | | |
| 1 = Vay Satisfied | 0 | 40 (17.5) | 24 (20.0) |
| 2 = Sansted | 2 (1.7) | 66 (28.9) | 38 (31.7) |
| 3 = Neither Satisfied Nor Dissatisfied | 16 (13.6) | 34 (14.9) | 23 (19.2) |
| 4 = Dissatisfied | 20 (16.9) | 34 (14.9) | 18 (15.0) |
| 5 = Very Dissatisfied | 80 (67.8) | 54 (23.7) | 17 (14.2) |
| Missing | 9 | 21 | 3 |
| SPRO Responders[1][2], n (%) | | | |
| Yes | 2 (1.7) | 106 (46.5) | 62 (51.7) |
| No | 116 (98.3) | 122 (53.5) | 58 (48.3) |
| Missing | 9 | 21 | 7 |
| Treatment difference[3] | | | |
| Common Risk Difference | | 0.45 | 0.49 |
| SE | | 0.035 | 0.047 |
| 95% CI | | (0.38, 0.52) | (0.40, 0.58) |
| P value | | <0.0001 | <0.0001 |

BID = twice daily;
CI = confidence interval;
MAR = missing at random;
MI = multiple imputation;
SE = standard error;
SPRO = Satisfaction of Hair Patient Reported Outcome
[1]Counts and percentages based on non-missing data.
[2]SPRO responders are subjects with responses of 'Very satisfied' or 'Satisfied'.
[3]The common risk difference, SE, 95% CIs, and P value were based on the Mantel-Haenszel estimate stratified by baseline scalp hair loss (partial vs complete near-complete) for each treatment group compared to Placebo. Missing values were imputed using MI under MAR assumptions. Estimates displayed are the combined statistics from PROC MIANALYZE after imputations.

The Hair Satisfaction Patient Reported Outcome (SPRO) was also determined based on the 5-point SPRO scale from baseline through Week 24 among primary endpoint responders. The subjects that received a SALT score ≤20 at Week 24 in the THRIVE-AA1 and THRIVE-AA2 trials were included in the analysis. Shift analyses excluded subjects reporting a score of 3 (neither satisfied nor dissatisfied) at baseline and post baseline to determine the percentage of subjects who shifted from "dissatisfied" (including very dissatisfied/dissatisfied) at baseline to "satisfied" (including satisfied/very satisfied) during treatment. Among Week 24, SALT ≤20 responders to deuruxolitinib 8 mg who were dissatisfied with their hair at baseline, 79.6% were satisfied at Week 12, 86.8% were satisfied at Week 16, 93.8% were satisfied at Week 20, and 95.7% were satisfied at Week 24. These results show that subjects who achieved clinically meaningful hair regrowth (SALT score ≤20) during 24 weeks of deuruxolitinib 8 mg BID treatment were satisfied at Week 24.

Absolute SALT Score of ≤20 at Weeks 20, 16, 12 and 8

Figure 2:
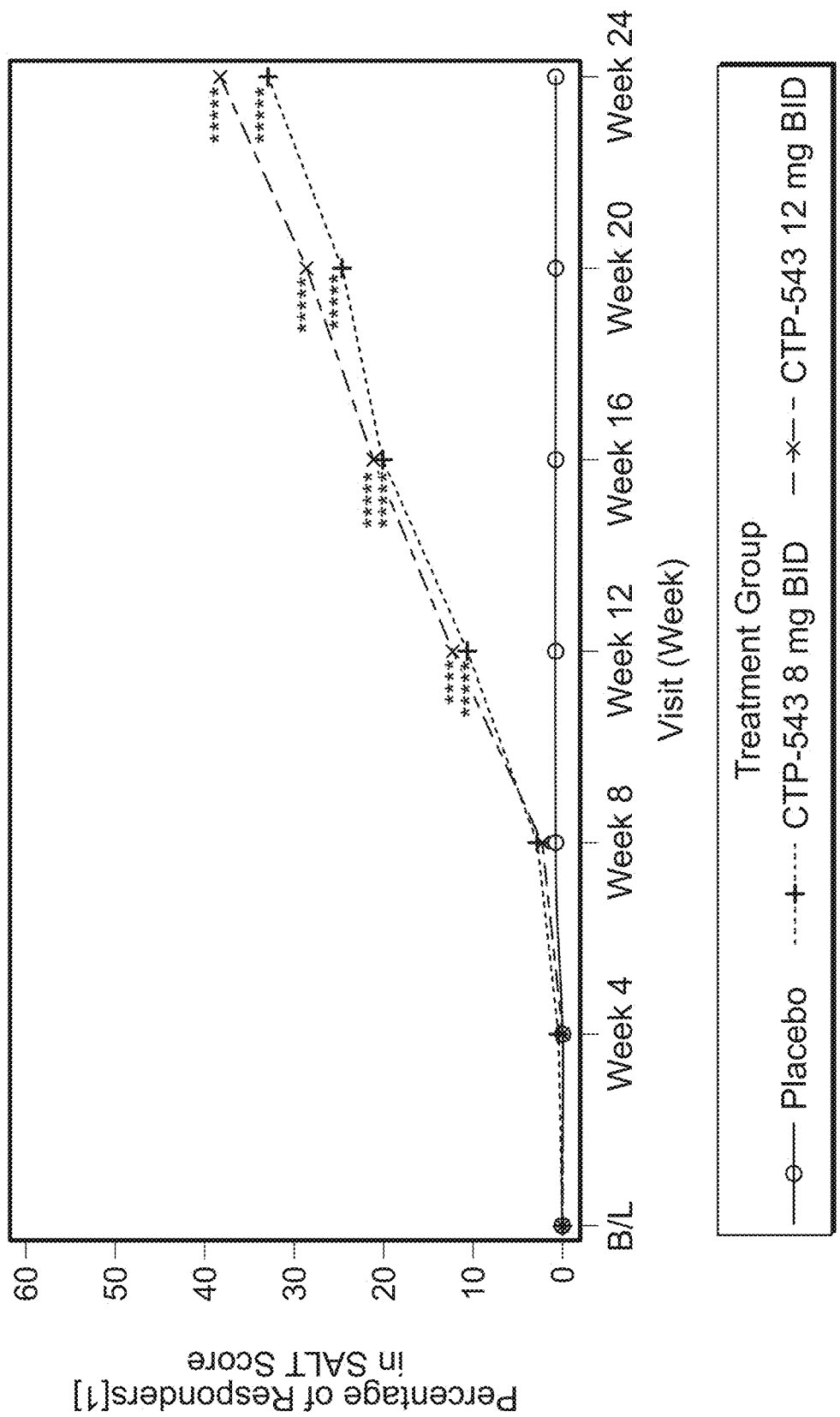
FIG. 2 is a graph of the percentage of subjects administered either 8 mg BID or 12 mg BID of CTP-543 having a SALT score of ≤20 versus weeks of treatment.

Statistically significant differences in outcomes favoring active over placebo were observed at each of these time points except week 8. (FIG. 2). An absolute SALT score of ≤20 was achieved at week 20 by 24.8% of CTP-543 8 mg BID subjects, 28.8% of CTP-543 12 mg BID subjects, and 0.8% of placebo subjects. An absolute SALT score of ≤20 was achieved at week 16 by 20.2% of CTP-543 8 mg BID subjects, 21.1% of CTP-543 12 mg BID subjects, and 0.8% of placebo subjects. An absolute SALT score of ≤20 was achieved at week 12 by 10.5% of CTP-543 8 mg BID subjects, 12.3% of CTP-543 12 mg BID subjects, and 0.8% of placebo subjects. An absolute SALT score of ≤20 was achieved at beginning week 8 by 2.9% of CTP-543 8 mg BID subjects, 2.4% of CTP-543 12 mg BID subjects, and 0.8% of placebo subjects.

Relative Change in Severity of Alopecia Tool Scores from Baseline at Weeks 4, 8, 12, 16, 20, and 24

A decrease in SALT score indicates increased hair growth. Decreases in the LS mean SALT scores were initially observed at Week 4. At each subsequent assessment, the size of the decreases observed increased through Week 24 and, at each time point, the LS mean difference versus placebo was larger for the CTP-543 8 mg BID group and CTP-543 12 mg BID group. At week 8, the LS mean change from baseline SALT score was higher in subjects treated with deuruxolitinib 8 mg BID (8.6%) than in subjects treated with 16 mg once daily (QD) (2.7%).

At Week 4, the LS mean change from baseline was −2.5 (95% CI, −3.7, −1.4) for the CTP-543 8 mg BID group, −3.1 (95% CI −4.6, −1.5) for the CTP-543 12 mg BID group, and −0.3 (95% CI −1.3, 1.8) for the placebo group.

At Week 8, the LS mean change from baseline was −11.5 (95% CI −13.9, −9.0) for the CTP-543 8 mg BID group, −16.3 (95% CI −19.7, −12.8) for the CTP-543 12 mg BID group, and −2.1 (95% CI −5.5, 1.3) for the placebo group.

At Week 12, the LS mean change from baseline was −23.8 (95% CI −27.1, −20.4) for the CTP-543 8 mg BID group, −30.1 (95% CI −34.7, −25.4) for the CTP-543 12 mg BID group, and −0.8 (95% CI −5.4, 3.9) for the placebo group.

At Week 16, the LS mean change from baseline was −34.1 (95% CI −38.0, −30.2) for the CTP-543 8 mg BID group, −39.5 (95% CI −44.9, −34.2) for the CTP-543 12 mg BID group, and −0.7 (95% CI −4.7, 6.1) for the placebo group.

At Week 20, the LS mean change from baseline was −38.4 (95% CI −42.6, −34.3) for the CTP-543 8 mg BID group, −46.3 (95% CI −52.1, −40.5) for the CTP-543 12 mg BID group, and 0.3 (95% CI −5.5, 6.1) for the placebo group.

At Week 24, the LS mean change from baseline was −44.4 (95% CI −48.8, −40.0) for the CTP-543 8 mg BID group, −51.3 (95% CI −57.4, −45.2) for the CTP-543 12 mg BID group, and 1.5 (95% CI −4.5, 7.6) for the placebo group.

Percentage of Responders Using the Clinical Global Impression of Improvement at Weeks 12, 16, 20, and 24

Subjects with responses of "very much improved" or "much improved" were considered CGI-I responders. The percentage of responders was higher in each CTP-543 group than the placebo group at all time points evaluated; the CTP-543 12 mg BID group was numerically superior to that of the CTP-543 8 mg BID group at all time points evaluated. Detailed data are described below. At each visit, the percentage of CGI-I responders (non-missing data) was as follows:

At Week 12, CGI-I responders were 38.0% of CTP-543 8 mg BID group (CMH P<0.0001) 44.3% of CTP-543 12 mg BID group (CMH P<0.0001) and 3.3% of the placebo group.

At Week 16, CGI-I responders were 45.0% of CTP-543 8 mg BID group (CMH P<0.0001) 52.0% of CTP-543 12 mg BID group (CMH P<0.0001) and 3.2% of the placebo group.

At Week 20, CGI-I responders were 50.0% of CTP-543 8 mg BID group (CMH P<0.0001) 9.0% of CTP-543 12 mg BID group (CMH P<0.0001) and 1.7% of the placebo group.

At Week 24, CGI-I responders were 54.1% of CTP-543 8 mg BID group (CMH P<0.0001) 61.7% of CTP-543 12 mg BID group (CMH P<0.0001) and 2.5% of the placebo group.

Percentage of Responders Using the Patient Global Impression of Improvement at Weeks 12, 16, 20, and 24

PGI-I responders were subjects with responses of "very much improved" or "much improved." The CTP-543 groups had a higher percentage of PGI-I responders compared with the placebo group at all time points evaluated. The percentage of PGI-I responders in the CTP-543 12 mg BID group was numerically superior to that of the CTP-543 8 mg BID group at all time points evaluated. Detailed data are described below.

At each visit, the percentage of PGI-I responders (non-missing data) was as follows:

At Week 12, PGI-I responders were 43.3% of the CTP-543 8 mg BID group (CMH P<0.0001) 49.2% of CTP-543 12 mg BID group (CMH P<0.0001) and 3.3% of the placebo group.

At Week 16, PGI-I responders were 46.2% of the CTP-543 8 mg BID group (CMH P<0.0001) 59.8% of CTP-543 12 mg BID group (CMH P<0.0001) 4.0% of the placebo group.

At Week 20, PGI-I responders were 48.7% of the CTP-543 8 mg BID group (CMH P<0.0001) 64.4% of CTP-543 12 mg BID group (CMH P<0.0001) 5.8% of the placebo group.

At Week 24, PGI-I responders were 50.9% of the CTP CTP-543 8 mg BID group (CMH P 68.3% of CTP-543 12 mg BID group (CMH P<0.0001) 1.7% of the placebo group.

Change from Baseline in the Clinical Global Impression of Severity at Weeks 12, 16, 20, and 24

A decrease in CGI-I score indicates improvement (impression is decreased severity). Similar to other endpoints, decreases favoring the active group over placebo were observed beginning at Week 12 and continuing through Week 24, and the magnitude of the differences increased at each subsequent time point. Additionally, and also consistent with other endpoints, the CTP-543 12 mg BID group experienced larger LS mean decreases in CGI-S than the CTP-543 8 mg BID group at each time point assessed. Detailed data for each time point are described below.

The LS mean change from baseline at Week 12 was −1.3 (95% CI −1.4, −1.1) for the CTP-543 8 mg BID group, −1.4 (95% CI −1.7, −1.2) for the CTP-543 12 mg BID group, and −0.0 (95% CI −0.3, 0.2) for the placebo group. At Week 16, the LS mean change from baseline was-1.6 (95% CI −1.8, −1.4) for the CTP-543 8 mg BID group, −1.8 (95% CI −2.1, −1.6) for the CTP-543 12 mg BID group, and −0.0 (95% CI −0.2, 0.2) for the placebo group. At Week 20, the LS mean change from baseline was −1.8 (95% CI −2.0, −1.6) for the CTP-543 8 mg BID group, −2.1 (95% CI −2.4, −1.9) for the CTP-543 12 mg BID group, and −0.1 (95% CI −0.4, 0.2) for the placebo group. At Week 24, the LS mean change from baseline was −2.1 (95% CI −2.3, −1.9) for the CTP-543 8 mg BID group, −2.4 (95% CI −2.6, −2.1) for the CTP-543 12 mg BID group, and 0.0 (95% CI −0.3, 0.3) for the placebo group.

Change from Baseline in the Patient Global Impression of Severity at Weeks 12, 16, 20, and 24

A decrease from baseline indicates improvement (impression is decreased severity). The LS mean treatment group difference was in favor of the CTP-543 groups over the placebo group at all timepoints evaluated. At each visit, the LS mean treatment group difference was more favorable (more negative number) for the CTP-543 12 mg BID group than the CTP-543 8 mg BID group. Detailed data for each time point are described below.

The LS mean change from baseline at Week 12 was −1.6 (95% CI −1.8, −1.4) for the CTP-543 8 mg BID group, −1.8 (95% CI −2.1, −1.4) for the CTP-543 12 mg BID group, and −0.2 (95% CI −0.5, 0.1) for the placebo group. At Week 16, the LS mean change from baseline was −1.8 (95% CI −2.0, −1.6) for the CTP-543 8 mg BID group, −2.0 (95% CI −2.3, −1.7) for the CTP-543 12 mg BID group, and −0.2 (95% CI −0.5, 0.1) for the placebo group. At Week 20, the LS mean change from baseline was −2.0 (95% CI −2.2, −1.8) for the CTP-543 8 mg BID group, −2.2 (95% CI −2.5, −1.9) for the CTP-543 12 mg BID group, and −0.3 (95% CI −0.6, 0.1) for the placebo group. At Week 24, the LS mean change from baseline was −2.2 (95% CI −2.5, −2.0) for the CTP-543 8 mg BID group, −2.5 (95% CI −2.8, −2.1) for the CTP-543 12 mg BID group, and −0.1 (95% CI −0.5, 0.2) for the placebo group.

Percentage of Subjects Achieving at Least a 75% Relative Reduction in SALT Score from Baseline at Weeks 8, 12 and 24

At Week 8, 3.4% of CTP-543 8 mg BID subjects, 3.5% of CTP 16 mg BID subjects, and 0 placebo subjects had a relative reduction in SALT score from baseline that was ≥75%. At Week 12, 8.9% of CTP-543 8 mg BID subjects, 11.5% of CTP 12 mg BID subjects, and 0 placebo subjects had a relative reduction in SALT score from baseline that was ≥75%. At Week 24, 33.5% of CTP-543 8 mg BID subjects, 38.3% of CTP 12 mg BID subjects, and 0 placebo subjects achieved a ≥75% relative reduction in SALT score from baseline.

Percentage of Subjects Achieving at Least a 90% Relative Reduction in Severity of Alopecia Tool Score from Baseline at Weeks 12 and 24

The percentage of subjects with 90% relative reduction I SALT score from baseline at week 12 was 1.7% of the CTP-543 8 mg BID subjects, 4.9% of CTP 12 mg BID subjects, and 0 placebo subjects. At week 24, 21.9% of CTP-543 8 mg BID subjects, 25.0% of CTP 12 mg BID subjects, and 0 placebo subjects achieved a ≥90% relative reduction in SALT score from baseline.

Percentage of Responders, Change from Baseline, and Percentage of Subjects Achieving a ≥2.0 Point Change from Baseline on the Hair Satisfaction Patient Reported Outcome Scale.

The SPRO was evaluated in 3 different ways: the percentage of responders, the change from baseline, and the percentage of subjects achieving a ≥2.0 point change from baseline.

The percentage of responders (based on non-missing data) at week 12 was 43.2% of the CTP-543 8 mg BID group, 41.0% of the CTP-543 12 mg BID group, and 4.9% of the placebo group.

The percentage of responders (based on non-missing data) at week 16 was 41.0% of the CTP-543 8 mg BID group, 45.1% of the CTP-543 12 mg BID group, and 4.9% of the placebo group.

The percentage of responders (based on non-missing data) at week 20 was 40.1% of the CTP-543 8 mg BID group, 52.5% of the CTP-543 12 mg BID group, and 1.7% of the placebo group.

A decrease in the SPRO score indicates a higher degree of satisfaction. The LS mean change from baseline at Week 12 was −1.6 (95% CI −1.8, −1.5) for the CTP-543 8 mg BID group, −1.7 (95% CI −1.9, −1.5) for the CTP-543 12 mg BID group, and −0.4 (95% CI −0.7, −0.2) for the placebo group.

At Week 16, the LS mean change from baseline was −1.6 (95% CI −1.7, −1.4) for the CTP-543 8 mg BID group, −1.7 (95% CI −1.9, −1.5) for the CTP-543 12 mg BID group, and −0.2 (95% CI −0.4, 0.0) for the placebo group.

The LS mean change from baseline at Week 20 was −1.5 (95% CI −1.7, −1.4) for the CTP-543 8 mg BID group, −1.8 (95% CI −2.1, −1.6) for the CTP-543 12 mg BID group, and −0.1 (95% CI −0.3, 0.1) for the placebo group.

At Week 24, the LS mean change from baseline was −1.6 (95% CI −1.8, −1.5) for the CTP-543 8 mg BID group, −1.8 (95% CI −2.1, −1.6) for the CTP-543 12 mg BID group, and −0.1 (95% CI −0.3, 0.1) for the placebo group.

The percentage of subjects with non-missing data with a ≥2 point change at week 12 was 50.4% of CTP-543 8 mg BID subjects, 59.0% of CTP-543 12 mg BID subjects, and 15.6% of placebo subjects.

The percentage of subjects with non-missing data with a ≥2 point change at week 16 was 52.6% of CTP-543 8 mg BID subjects, 57.4% of CTP-543 12 mg BID subjects, and 9.8% of placebo subjects.

The percentage of subjects with non-missing data with a ≥2 point change at week 20 was 50.4% of CTP-543 8 mg BID subjects, 63.6% of CTP-543 12 mg BID subjects, and 9.2% of placebo subjects.

The percentage of subjects with non-missing data with a ≥2 point change at week 24 was 52.6% of CTP-543 8 mg BID subjects, 61.7% of CTP-543 12 mg BID subjects, and 8.5% of placebo subjects.

Percentage of Subjects Achieving an Absolute Severity of Alopecia Tool Score ≤10 Week 24

Figure 14B:
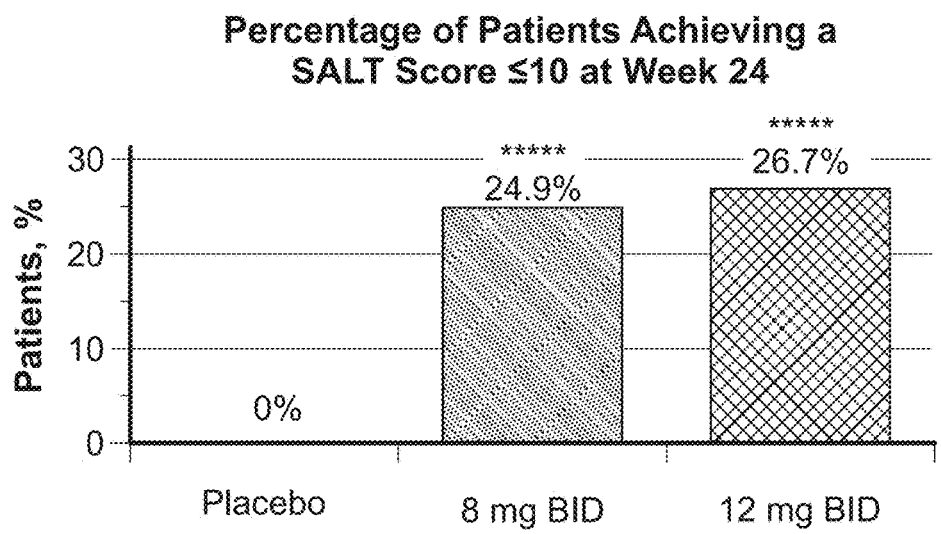
FIG. 14B is a graph showing the percentage of subjects achieving a SALT score of ≤ 10 at week 12. Subjects were treated with placebo, 8 mg BID, or 12 mg BID.

There were 24.9% of CTP-543 8 mg BID subjects, 26.7% of CTP-543 12 mg BID subjects and 0 placebo subjects who had an absolute SALT score ≤10 at week 24 (FIG. 14B)

Change from Baseline in the Brigham Eyebrow Tool for Alopecia Score at Weeks 12 and 24

An increase in BETA score indicates an increase in hair growth. At Week 12, the LS mean change from baseline was 0.8 (95% CI 0.5, 1.0) for the CTP-543 8 mg BID group, 0.8 (95% CI 0.5, 1.0) for CTP-543 12 mg BID group, and −0.3 (95% CI 0.5, 0.0) for the placebo group.

At Week 24, the LS mean change from baseline was 1.1 (95% CI 0.9, 1.3) for the CTP-543 8 mg BID group, 1.4 (95% CI 1.1, 1.7) for the CTP-543 12 mg BID group, and −0.4 (95% CI −0.7, −0.0) for the placebo group.

Change from Baseline in the Brigham Eyelash Tool for Alopecia Score at Weeks 12 and 24

An increase in BELA score indicates an increase in hair growth. The LS mean change from baseline at Week 12 was 0.9 (95% CI 0.7, 1.2) for the CTP-543 8 mg BID group, 1.0 (95% CI 0.7, 1.4) for CTP-543 12 mg BID group, and −0.1 (95% CI −0.5, 0.2) for the placebo group.

The LS mean change from baseline at Week 24 was 1.4 (95% CI 1.1, 1.7) for the CTP-543 8 mg BID group, 1.5

(95% CI 1.1, 1.9) for CTP-543 12 mg BID group, and −0.1 (95% CI −0.5, 0.3) for the placebo group.

Change from Baseline on the Individual Items of the Hair Quality Patient Reported Outcome Scale at Weeks 12, 16, 20, and 24

The individual items of satisfaction with thickness of hair coverage, satisfaction with evenness of hair coverage, satisfaction with eyebrows, and satisfaction with eyelashes are rated on a scale of 1 to 5. A decrease from baseline in the QPRO score represents improvement. For each item and time point, treatment group differences favored CTP-543 over placebo.

For satisfaction with thickness of hair coverage, both CTP-543 groups showed improvement over placebo at Weeks 12, 16, 20, and 24, trending more negative while placebo was generally consistent. For the CTP-543 8 mg BID group, the treatment group difference from placebo ranged from −1.3 to −1.0. For the CTP-543 12 mg BID group, the treatment group difference from placebo ranged from −1.6 to −1.1.

For satisfaction with evenness of hair coverage, the CTP-543 groups trended towards more negative while placebo was generally consistent. For the CTP-543 8 mg BID group, the treatment group difference from placebo ranged from −1.3 to −0.9. For the CTP-543 12 mg BID group, the treatment group difference from placebo ranged from −1.5 to −1.0.

For satisfaction with eyebrows, the CTP-543 groups trended towards more negative while placebo was generally consistent. For the CTP-543 8 mg BID group, the treatment group difference from placebo ranged from −1.2 to −1.0. For the CTP-543 12 mg BID group, the treatment group difference from placebo ranged from −1.5 to −1.1.

For satisfaction with eyelashes, the CTP-543 groups trended towards more negative while placebo was generally consistent. For the CTP-543 8 mg BID group, the treatment group difference from placebo ranged from −1.2 to −0.9. For the CTP-543 12 mg BID group, the treatment group difference from placebo ranged from −1.4 to −0.9.

Subjects completing 24 weeks of treatment with LEQ-SELVI 8 mg twice daily in the Phase III trial were eligible to continue treatment in an open label extension trial. Following 52 additional weeks of treatment with LEQ-SELVI™ 8 mg twice daily clinical response rates continued to increase with approximately 74% of the 80 subjects on 8 mg twice daily for 76 weeks achieving SALT ≤20.

Change from Baseline in Patient Responses on the Hospital Anxiety and Depression Scale (HADS) at Week 24

Changes from baseline to Week 24 in the depression scale of subjects who were randomized to treatment with deuruxolitinib 8 mg twice daily (BID), deuruxolitinib 12 mg BID, or placebo for 24 weeks were measured. Subjects completed the HADS 14-item questionnaire with 7 items for anxiety (HADS-A) and 7 items for depression (HADS-D). Each item on the HADS is scored on a 4-point scale (0-3), with an overall score of 0 to 42 (0-21 for HADS-A and 0-21 for HADS-D). Among subjects treated with deuruxolitinib 8 mg BID, 22.5% achieved a ≥6-point improvement in the overall HADS score from baseline to Week 24 compared with 11.8. % of placebo-treated subjects.

Change from Baseline in the Anxiety Scale 18.9% of subjects receiving deuruxolitinib 8 mg BID vs 10.2% of placebo-treated subjects achieved a ≥4-point improvement in the HADS-A score. The LS mean change from baseline at Week 24 was −1.1 (95% CI −1.5, −0.8) for CTP-543 8 mg BID, −0.9 (95% CI −1.3, −0.4) for CTP-543 12 mg BID, and −0.7 (−1.1, −0.2) for placebo. The LS mean treatment group difference from placebo was 0.5 (95% CI −0.1, 1.0; P=0.1206) and 0.2 (95% CI −0.5, 0.9; P=0.5367) for CTP-543 8 mg BID and CTP-543 12 mg BID, respectively.

Change from Baseline in the Depression Scale 26.2% of subjects treated with deuruxolitinib 8 mg BID vs 14.2% of subjects treated with placebo achieved a ≥3-point improvement in the HADS-D score from baseline to Week 24. The LS mean change from baseline at Week 24 was −1.2 (95% CI −1.6, −0.9) for CTP-543 8 mg BID, −1.5 (95% CI −2.0, −1.1) for CTP-543 12 mg BID, and −0.4 (95% CI −0.9, 0.0) for placebo. The LS mean treatment group difference from placebo was 0.8 (95% CI 0.2, 1.3; P=0.0064) and 1.1 (95% CI 0.4, 1.7; P=0.0011) for CTP-543 8 mg BID and CTP-543 12 mg BID, respectively.

These results show that significantly greater proportion of subjects treated with deuruxolitinib 8 mg BID vs placebo reported clinically meaningful improvement in overall HADS score, as well as the HADS-A and HADS-D subscales, from baseline to Week 24.

Example 3: Open-Label Extension (Ole) Study

Background

Deuruxolitinib (a compound represented by Compound (I) described herein) has demonstrated significant improvements in hair regrowth vs placebo in the two Phase 3 trials THRIVE-AA1 and THRIVE-AA2: treatment of adult subjects with alopecia areata receiving 8 mg twice daily (BID) and 12 mg BID dose for 24 weeks. The long-term effectiveness of deuruxolitinib is being evaluated in 2 ongoing OLE studies in North America and the European Union. Following an analysis of long-term data through 52-weeks of dosing, continued improvement in hair regrowth beyond assessment in the initial 24-week controlled studies was observed. Details of the OLE study and results are described below.

Following an analysis of long-term data through 68-weeks of dosing, improvement in hair regrowth beyond assessment in the initial 24-week controlled studies continued to be observed.

Details of Study

DESCRIPTION

Two separate OLE trials were conducted in North America (CP543.5001) and the European Union (CP543.5002). Subjects with AA completing the 24-week treatment period from qualifying Phase 2 and Phase 3 trials, whether they were on active treatment or placebo, were eligible to enroll. The qualifying clinical trials including the following: 1. NCT03137381; 2. NCT03811912; 3. NCT03941548; 4. NCT04784533; 5. NCT04518995; and 6. NCT04797650 (all available a at https://clinicaltrials.gov). Both OLE trials were similarly designed, except: Trial CP543.5001 (North America) participants have the opportunity to continue in the trial for a maximum of 276 weeks; and Trial CP543.5002 (European Union) participants have the opportunity to continue in the trial for a maximum of 108 weeks.

Treatment Assignment and Data Analyses

Figure 3:
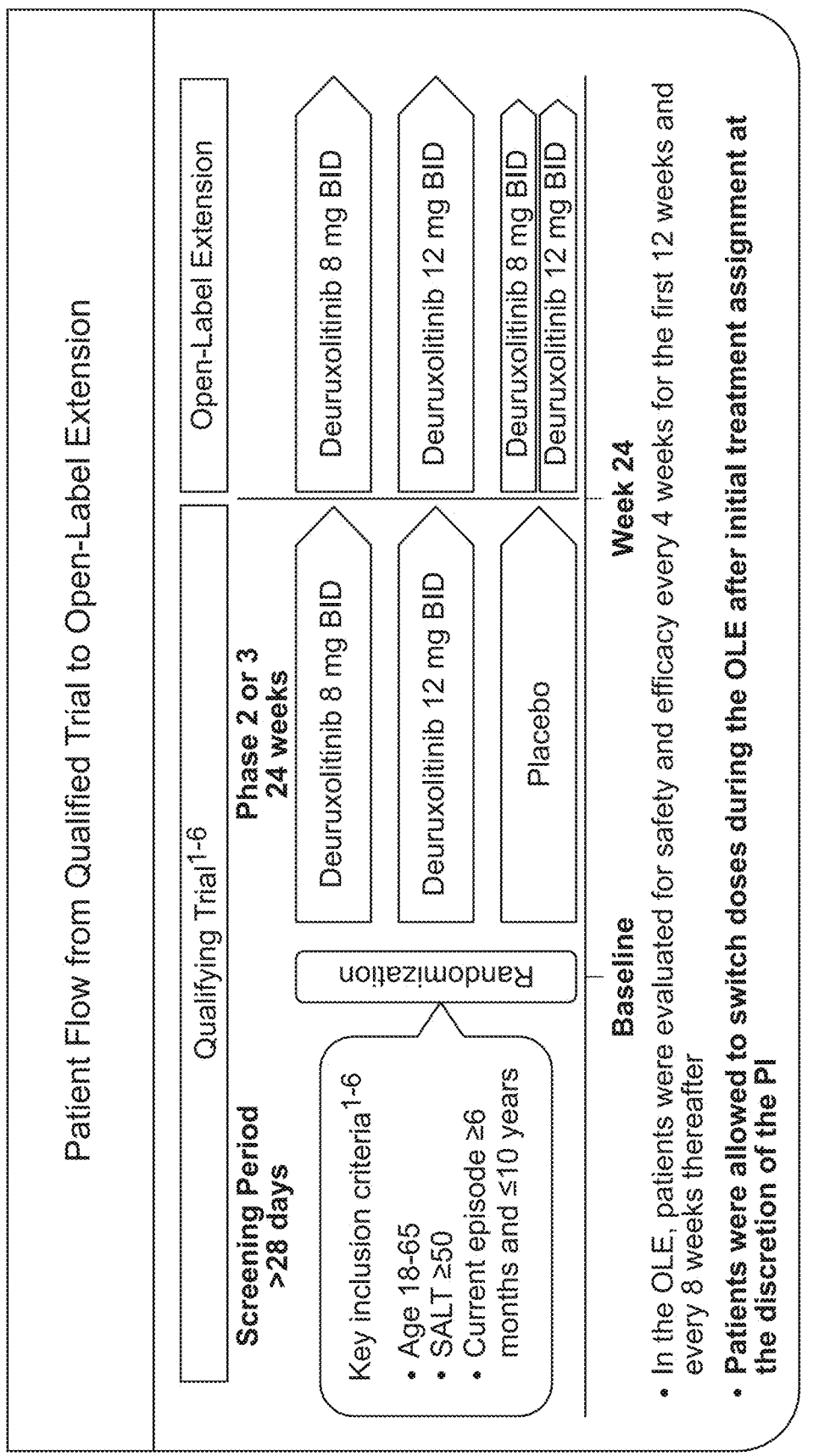
FIG. 3 is a diagram of the patient/subject flow from the qualified trial to the open-label extension.

Subjects receiving any active dose of deuruxolitinib in the qualifying trials were initially assigned to receive either 8 mg BID or 12 mg BID in the OLE trial. Subjects receiving placebo in the qualifying trial were assigned to either deuruxolitinib 8 mg BID or 12 mg BID. Subjects were allowed to switch doses during the OLE after initial treatment assignment at the discretion of the Principal Investigator. FIG. 3 is a diagram of the patient flow from the qualified trials to the open-label extension.

The OLE Efficacy Population is defined as all subjects who received at least one dose of deuruxolitinib and had at least one post-baseline SALT assessment in OLE. The data analyses include subjects' data from the qualifying trial. Missing SALT scores were not imputed. The number of subjects decreases over time due to missing data, patient discontinuations, or subjects not yet at the later timepoints. Any SALT data after a qualifying dose change in the OLE was censored for all figures included here, except those showing the overall treatment sequence. A "qualifying dose change" referred to herein can be placebo in any qualifying trial to any dose of deuruxolitinib in the OLE (includes subjects who switched doses), or any dose of deuruxolitinib in a qualifying trial to any dose of deuruxolitinib in the OLE. Various analyses using SALT scores were conducted to best estimate the overall long-term effect of deuruxolitinib considering the issues with dose changes and decreasing patient numbers over time. "Any Dose" analysis tracks all active subjects over time pooled across the two doses. "As Observed" analysis censors subjects at the time of dose adjustment or study discontinuation. "LOCF" (last observation carried forward) analysis utilizes the last SALT score before dose change and carries it forward for all other timepoints up to 52 weeks. Patient Demographics are shown in FIG. 4.

In some embodiments, LOCF analysis utilizes the last SALT score before dose change and carries it forward for all other timepoints up to 68 weeks. For example, the timepoint is at least 74 weeks. For example, the timepoint is at least 90 weeks. For example, the timepoint is at least 108 weeks. For example, the timepoint is at least 140 weeks. For example, the timepoint is at least 172 weeks. For example, the timepoint is at least 204 weeks. For example, the timepoint is at least 236 weeks. For example, the timepoint is at least 276 weeks.

Results
Percentage of Responders Over Time

Figure 5:
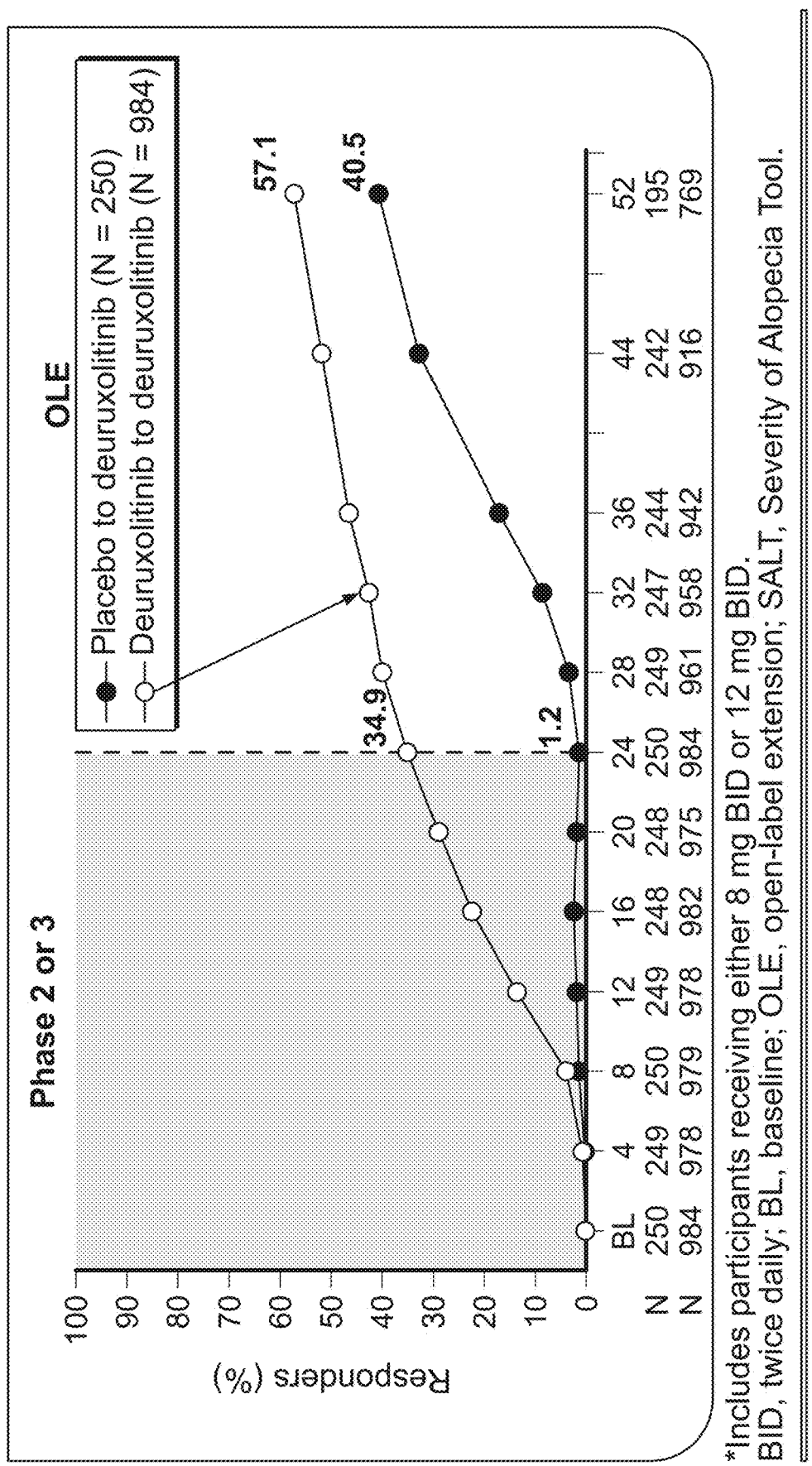
FIG. 5 is a graph showing the percentage of responders (subjects with a SALT score of ≤20) over time treated with any dose of deuruxolitinib.
Figure 6:
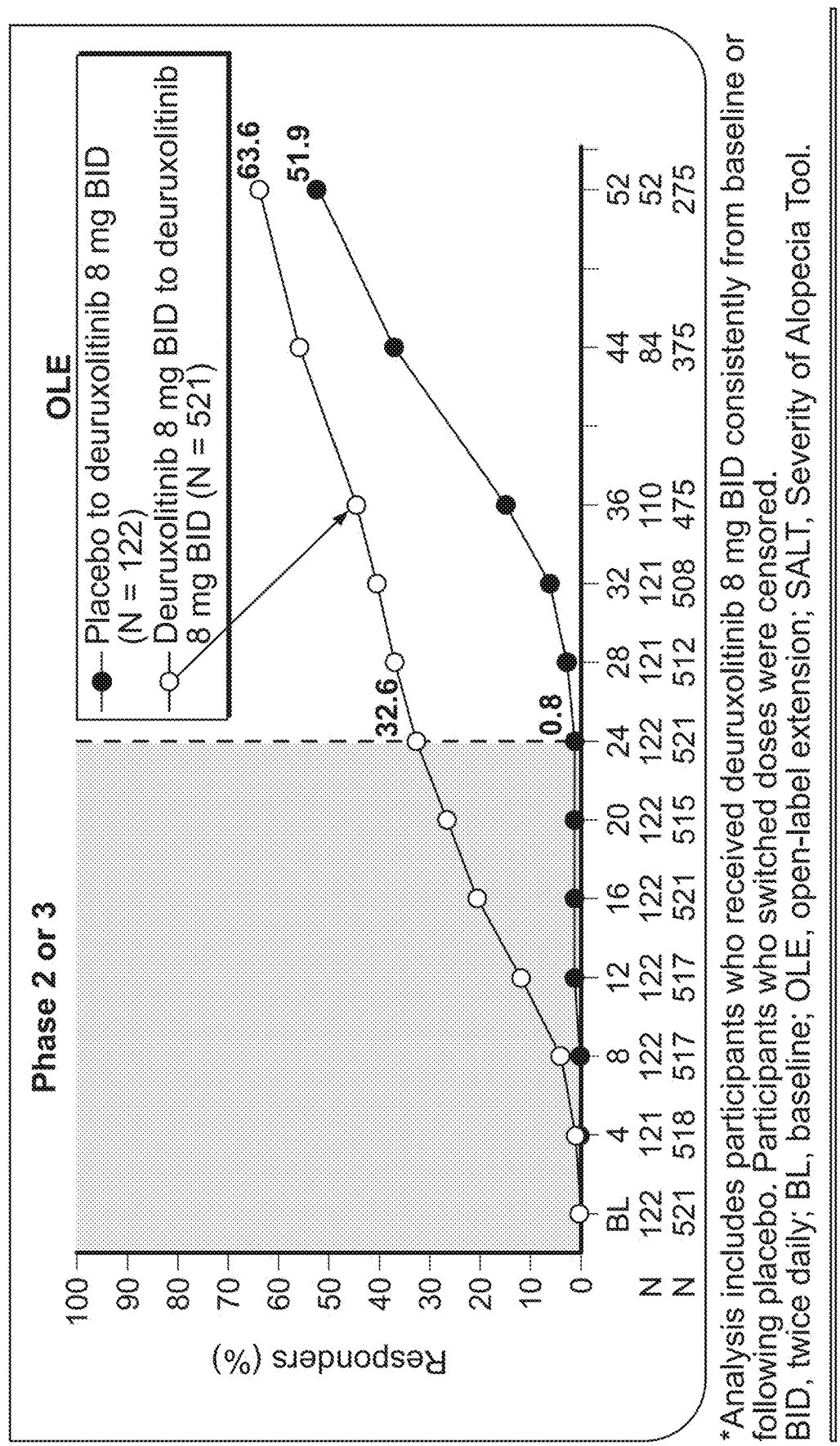
FIG. 6 is a graph showing the percentage of responders (subjects with a SALT score of ≤20) over time treated with 8 mg twice per day of deuruxolitinib.
Figure 7:
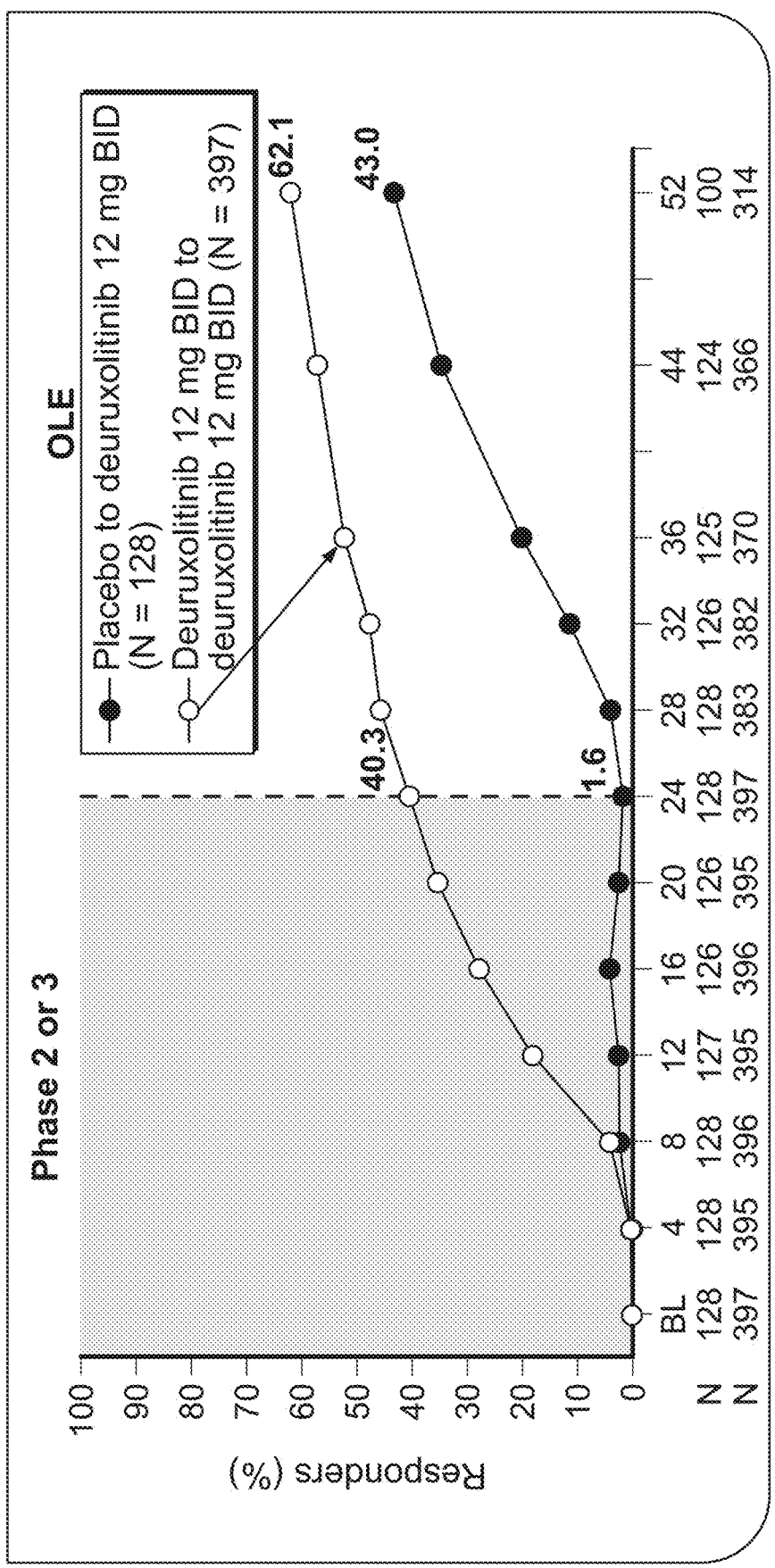
FIG. 7 is a graph showing the percentage of responders (subjects with a SALT score of ≤20) over time treated with 12 mg twice per day of deuruxolitinib.
Figure 11:
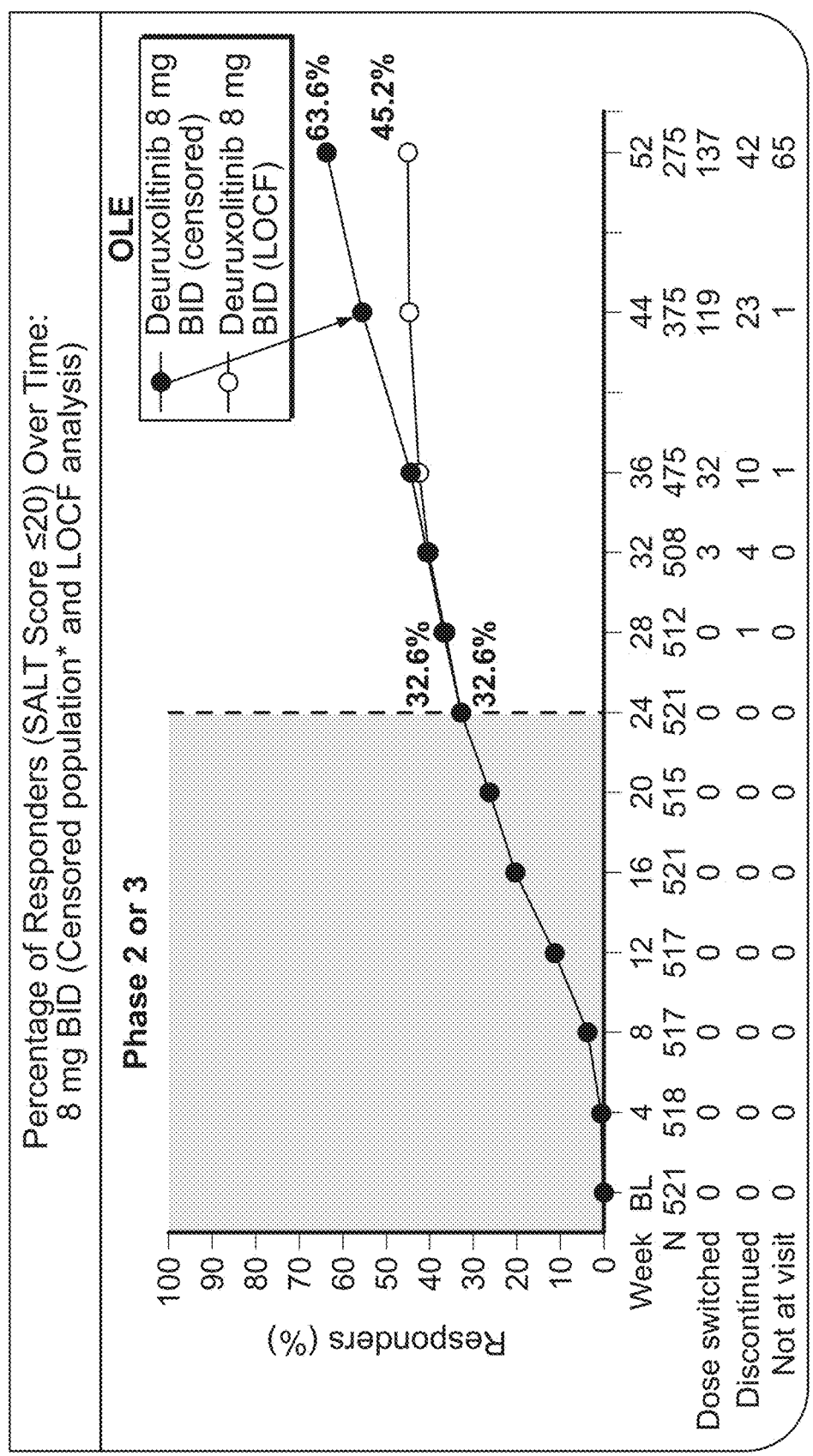
FIG. 11 is a graph showing the percentage of responders (subjects with a SALT score of ≤20) over time treated with 8 mg twice per day of deuruxolitinib (censored population and LOCF (last observation carried forward) analysis).

FIGS. 5-7 show that based on the interim analysis of pooled results from the two OLE studies, the percentage of subjects with a SALT score of ≤20 increased over time out to week 52. Specifically, FIG. 5 is a graph showing the percentage of responders (subjects with a SALT score of ≤20) over time treated with any dose of deuruxolitinib. The graph shows that 57.1% of subjects who received any dose of deuruxolitinib in the OLE (including switched doses) achieved a SALT score of ≤20. FIG. 6 is a graph showing the percentage of responders (subjects with a SALT score of ≤20) over time treated with 8 mg twice per day. The graph in FIG. 6 shows that 63.6 percent of subjects who received 8 mg twice per day of deuruxolitinib in the OLE achieved a SALT score of ≤20. FIG. 7 is a graph showing the percentage of responders (subjects with a SALT score of ≤20) over time treated with 12 mg twice per day. The graph in FIG. 7 shows that 62.1 percent of subjects who received 12 mg twice per day of deuruxolitinib in the OLE achieved a SALT score of ≤20. FIG. 11 is a graph showing the percentage of responders (subjects with a SALT score of ≤20) over time treated with 8 mg twice per day of deuruxolitinib (censored population and LOCF analysis).

Figure 12:
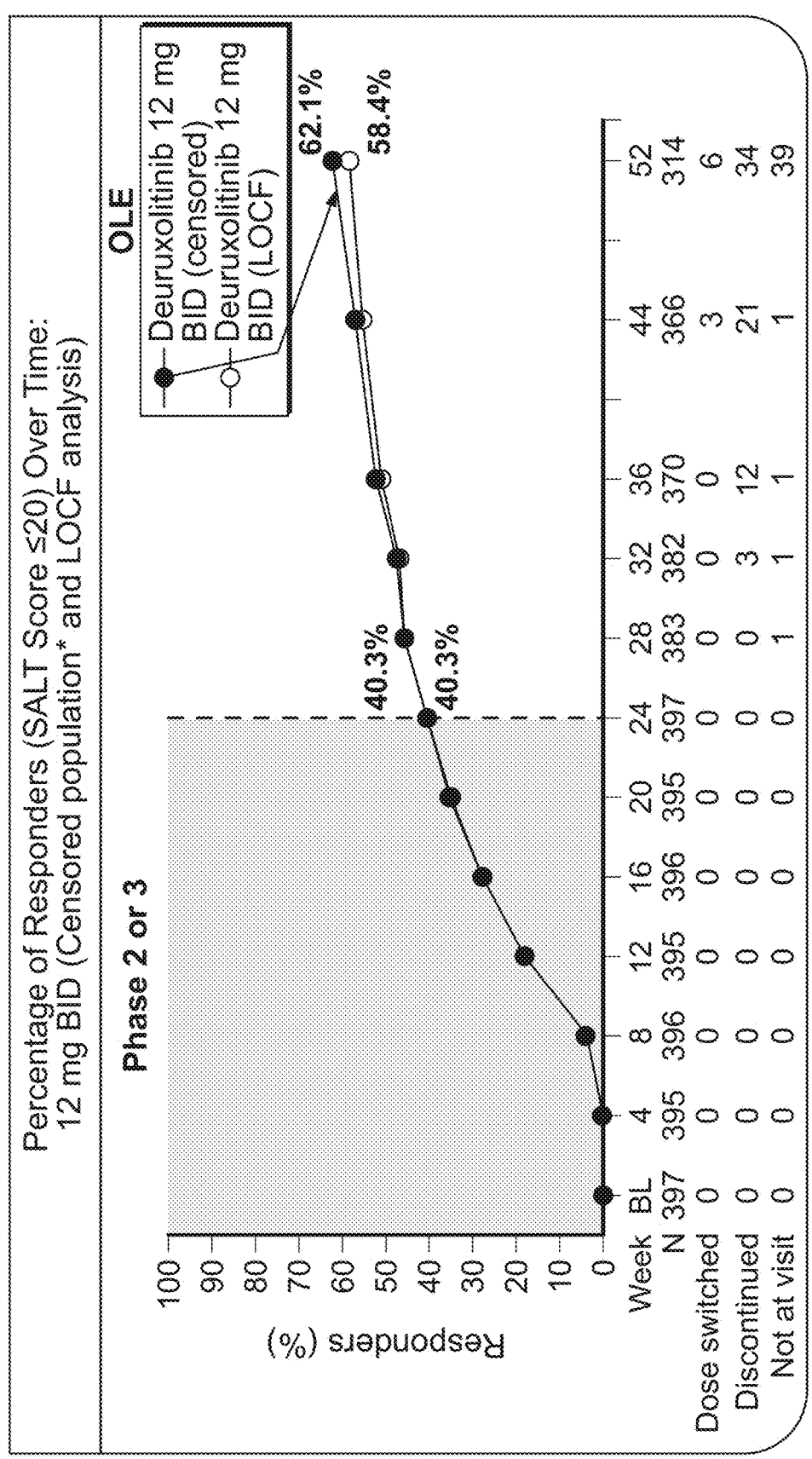
FIG. 12 is a graph showing the percentage of responders (subjects with a SALT score of ≤20) over time treated with 12 mg twice per day of deuruxolitinib (censored population and LOCF analysis).
Figure 13A:
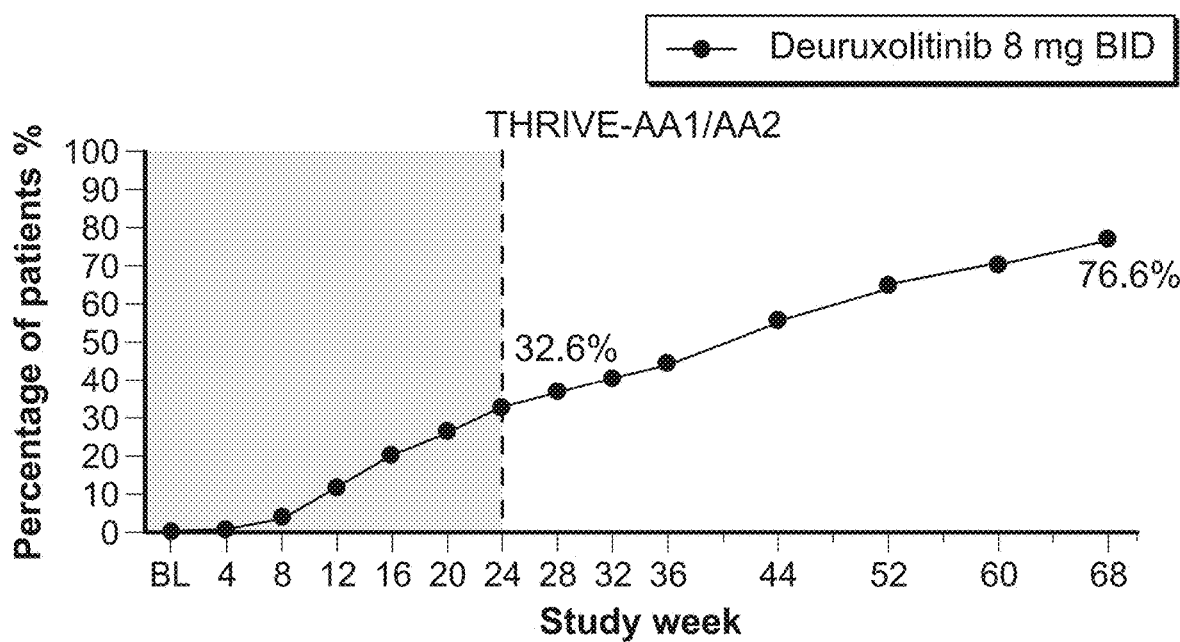
FIG. 13A, FIG. 13B, and FIG. 13C show the percentage of responders (subjects with a SALT score of ≤20) for up to 68 weeks for deuruxolitinib (8 mg twice daily), up to 52 weeks for baricitinib (4 mg), and up to 48 weeks for ritlecitinib (50 mg), respectively.
Figure 13B:
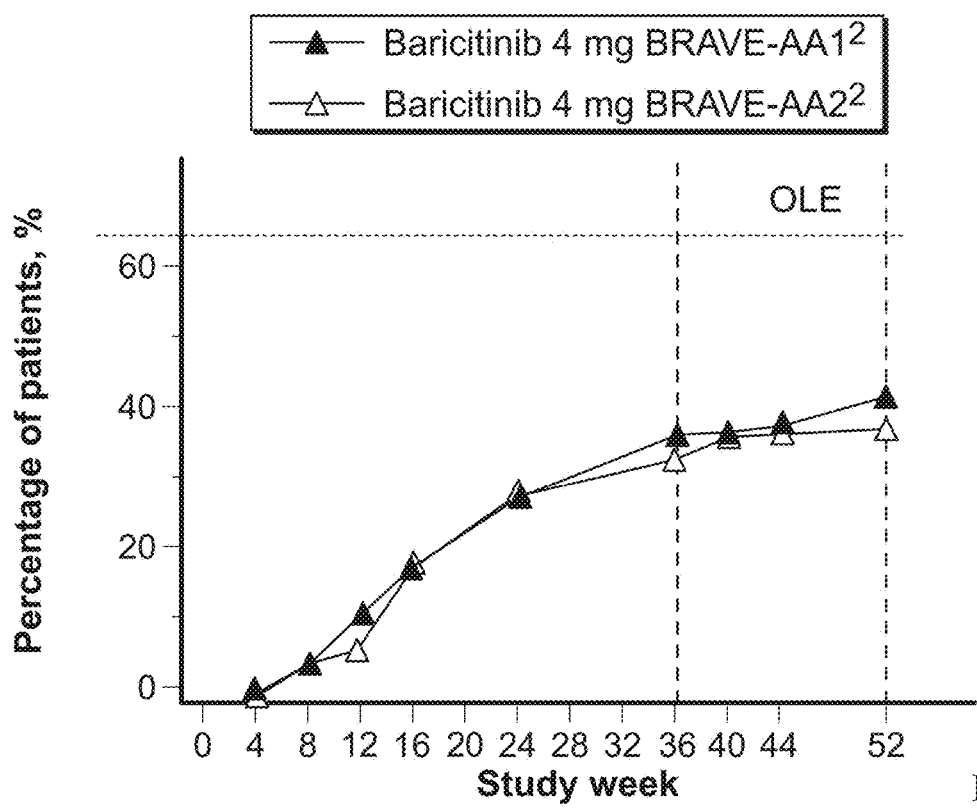
Figure 13C:
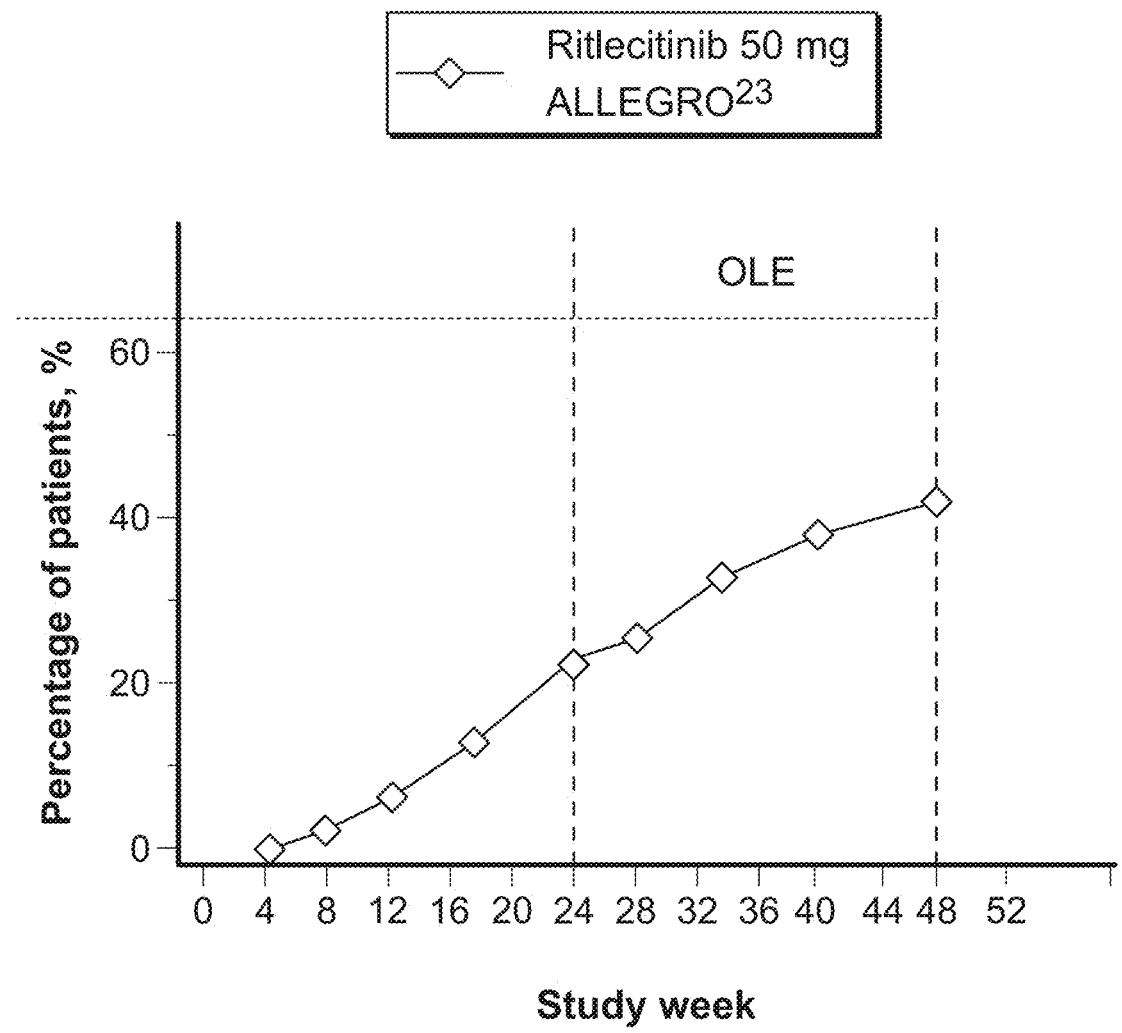

FIG. 12 is a graph showing the percentage of responders (subjects with a SALT score of ≤20) over time treated with 12 mg twice per day of deuruxolitinib (censored population and LOCF analysis). FIG. 13A, FIG. 13B, and FIG. 13C show the percentage of responders (subjects with a SALT score of ≤20) for up to 68 weeks for deuruxolitinib (8 mg twice daily), 52 weeks for baricitinib (4 mg), and 48 weeks for ritlecitinib (50 mg). The baricitinib data was taken from BRAVE-AA1 and BRAVE-AA2 studies summarized in King et al, N. Engl. J. Med. (2022) 386:1687-1699. The ritlecitinib data was taken from ALLEGOR studies summarized in Piliang et al, J. Cutaneous Med, (2024) 8: s394.

Pooled Mean Salt Scores Over Time

Figure 8:
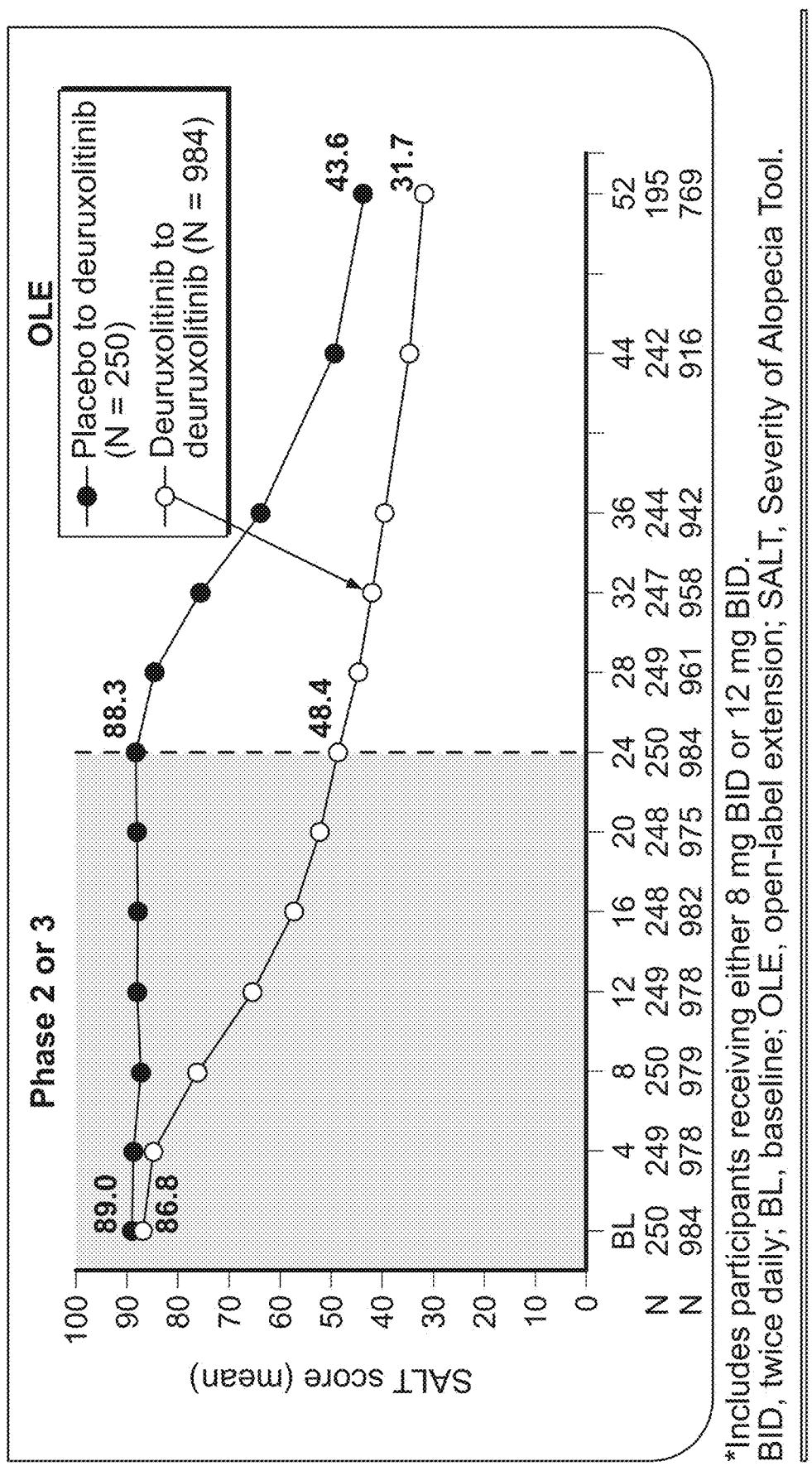
FIG. 8 shows the mean SALT scores over time for all treatment groups in the OLE study.
Figure 9:
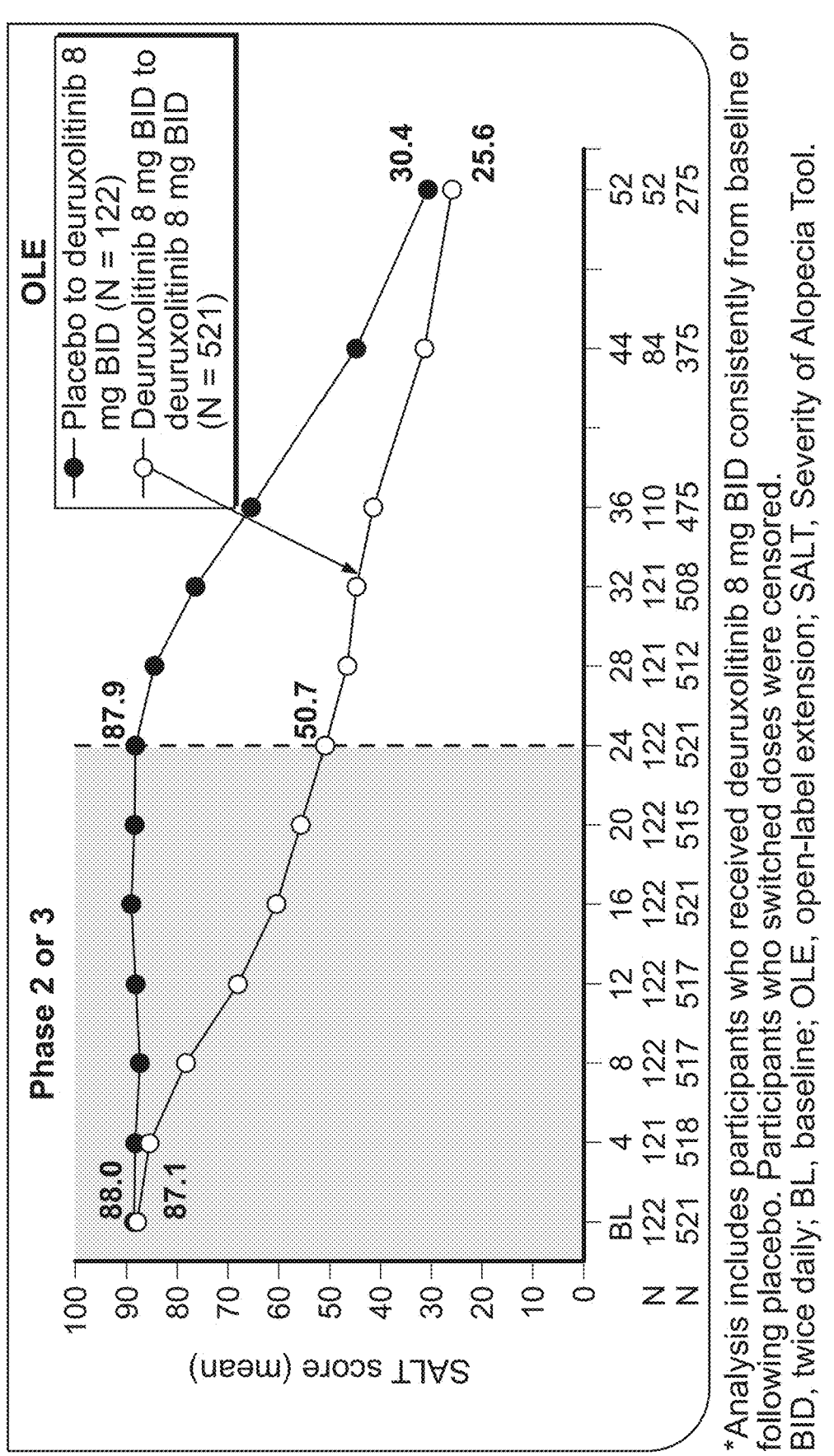
FIG. 9 shows the mean SALT scores over time for the group of subjects treated with 8 mg BID of deuruxolitinib in the OLE study.
Figure 10:
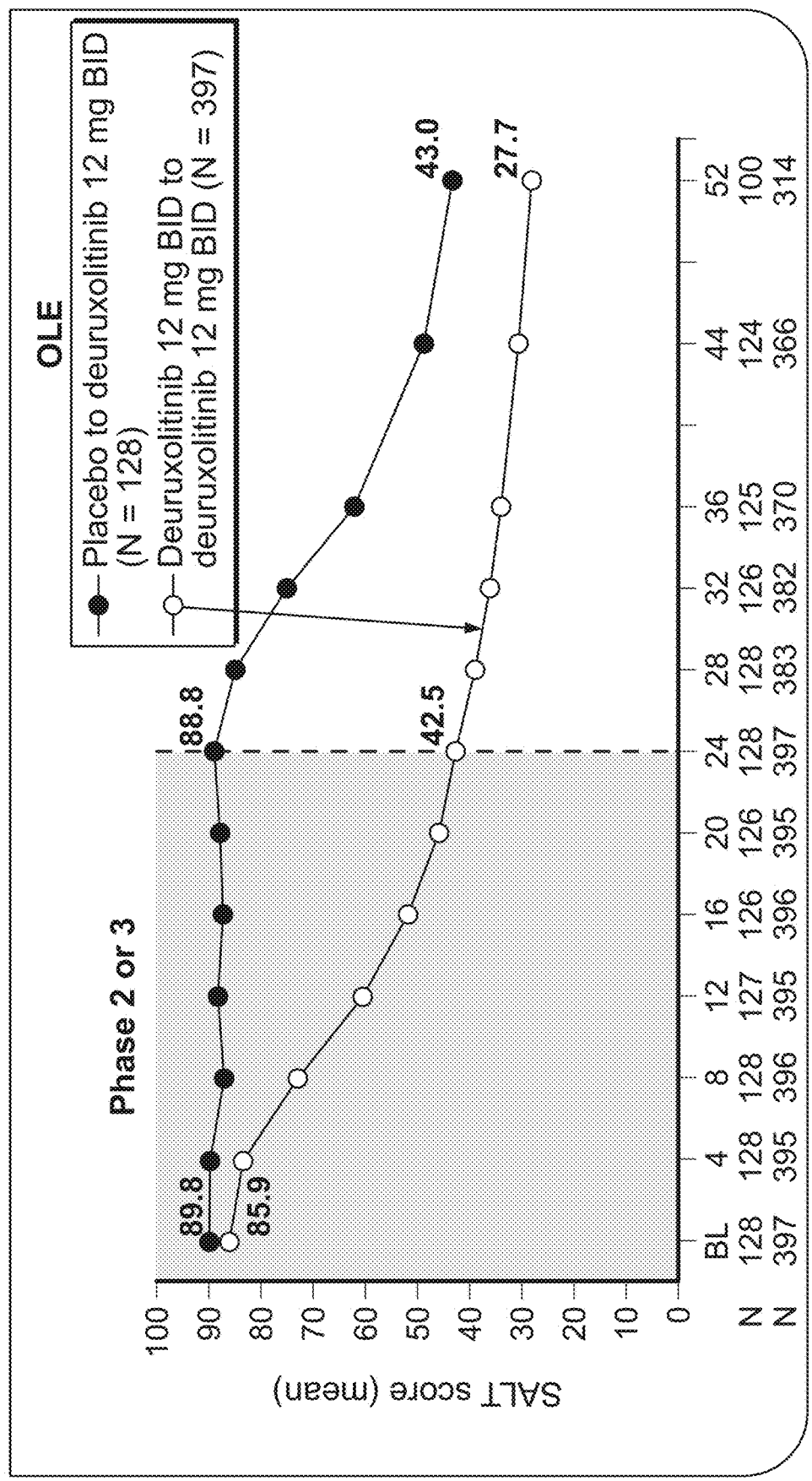
FIG. 10 shows the mean SALT scores over time for the group of subjects treated with 12 mg BID of deuruxolitinib in the OLE study.

FIGS. 8-10 show the mean SALT scores over time by treatment group. Specifically, FIG. 8 shows the pooled mean SALT score over time for subjects that received either 8 mg BID or 12 mg BID in the OLE. The graph in FIG. 8 shows that the subjects in the OLE study that were dosed with either 8 mg BID or 12 mg BID and that had been dosed with deuruxolitinib in the earlier studies had a mean SALT score of 31.7; and that subjects in the OLE study that received placebo in the earlier studies had a mean SALT score of 43.6 at 52 weeks. FIG. 9 shows the pooled mean SALT score over time for subjects that received 8 mg BID in the OLE. The graph in FIG. 9 shows that the subjects in the OLE study that were dosed with 8 mg of deuruxolitinib in the earlier studies had a mean SALT score of 25.6 at 52 weeks; and that the subjects in the OLE study that received placebo in the earlier studies had a mean SALT score of 30.4. FIG. 10 shows the pooled mean SALT score over time for subjects that received 12 mg BID in the OLE. The graph in FIG. 10 shows that the subjects in the OLE study that were dosed with 12 mg of deuruxolitinib in the earlier studies had a mean SALT score of 27.7 at 52 weeks; and that the subjects in the OLE study that received placebo in the earlier studies had a mean SALT score of 43.0.

Results Over Time Out to 68 Weeks and Beyond

Mean SALT scores decreased in participants who received deuruxolitinib (any dose) in a Qualifying Study (QS) and OLE from baseline 86.8 (SD 17.9; n=984) to 26.8 (SD 34.7; n=836) out to 68 weeks. The proportion of participants achieving SALT ≤20 established in the QSs increased from 34.9% to 62.6% in the OLE at Week 68. Both the 8 mg BID and 12 mg BID doses showed continued efficacy with a LOCF imputation analysis and an As Observed (AO) analysis. For LOCF, the proportion of participants achieving SALT ≤20 at Week 68 was 48.8% for 8 mg BID and 60.9% for 12 mg BID. For AO, the proportion of participants achieving SALT ≤20 at Week 68 was 76.6% for 8 mg BID and 66.7% for 12 mg BID. Treatment-emergent adverse event findings from integrated analyses are consistent with the safety profiles observed for other JAK inhibitors indicated for chronic inflammatory conditions. FIG. 13A demonstrates that the proportion of participants achieving SALT ≤20 continued to increase, achieving >80% for 8 mg BID at Week 68. The data is unexpected, as other JAK inhibitors used to treat AA, ritlecitinib and baricitinib, were not previously shown to provide a proportion of participants achieving SALT ≤20 of greater than even 50%, and the rate of increase in the proportion of participants achieving SALT ≤20 tapers off and may even plateau. See FIGS. 13B and 13C.

A total of 521 patients treated with deuruxolitinib 8 mg BID in a qualifying trial received the same dose in the OLE (8 mg BID/8 mg BID); 122 patients receiving placebo in a qualifying trial received deuruxolitinib 8 mg BID in the OLE (placebo/8 mg BID). "As observed," 179/256 (69.9%) of patients in the 8 mg BID/8 mg BID group and 39/59 (66.1%) of patients in the placebo/8 mg BID group achieved SALT 10 at Week 68. With LOCF, 213/521 (40.9%) and 41/122 (33.6%) of patients in the 8 mg BID/8 mg BID and placebo/8 mg BID groups, respectively, achieved SALT 10 at Week 68. The proportion of patients achieving SALT 10 in either group increased from Week 24 through Week 68 of the OLE. Of 373 patients receiving deuruxolitinib 8 mg BID in the OLE without a qualifying dose change, 283 were considered OLE responders, of whom 282 (99.6%) maintained treatment response in the OLE.

CONCLUSIONS

Deuruxolitinib 8 mg BID and deuruxolitinib 12 mg BID showed significant hair regrowth in Phase 2 and Phase 3 clinical trials. The long-term effectiveness of deuruxolitinib is being evaluated in 2 ongoing OLE studies in North America and the European Union. Following an analysis of long-term data through 52-weeks of dosing, continued improvement in hair regrowth beyond assessment in the initial 24-week controlled studies was observed.

Following an analysis of long-term data through 68-weeks of dosing, continued improvement in hair regrowth beyond assessment in the initial 24-week controlled studies was observed.

The interim analysis of pooled results from the 2 OLE studies showed that the percentage of subjects with a SALT score ≤20 increased over time out to Week 52. 57% of subjects who received any dose of deuruxolitinib in the OLE study (including switched doses) achieved a SALT score ≤20. 64% of subjects who received deuruxolitinib 8 mg BID in the OLE study achieved a SALT score ≤20. 62% of subjects who received deuruxolitinib 12 mg BID in the OLE study achieved a SALT score ≤20.

The interim analysis of pooled results from the 2 OLE studies showed that the percentage of subjects with a SALT score ≤20 increased over time out to Week 68. 63% of subjects who received any dose of deuruxolitinib in the OLE study (including switched doses) achieved a SALT score ≤20. 77% of subjects who received deuruxolitinib 8 mg BID in the OLE study achieved a SALT score ≤20. 67% of subjects who received deuruxolitinib 12 mg BID in the OLE study achieved a SALT score ≤20.

Deuruxolitinib was generally well tolerated in the OLE studies. The most common adverse events were COVID-19, acne, nasopharyngitis, headache, asymptomatic COVID-19, creatinine phosphokinase increase, and upper respiratory tract infection. The number of serious treatment-related TEAEs remains low. To date, four subjects have reported related thrombotic events (all at the 12 mg BID dose) following ≥52 weeks of dosing.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating alopecia areata in a subject in need thereof, the method comprising, orally administering to the subject 16 mg/day or 24 mg/day of Compound (I) or a pharmaceutically acceptable salt thereof, wherein Compound (I) is represented by the following structural formula:

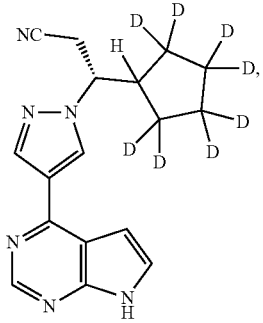

Compound (I)

wherein each position designated specifically as deuterium has at least 95% incorporation of deuterium, and wherein the subject has an estimated glomerular filtration rate (eGFR) of ≥30 mL/min, MDRD.

2. The method of claim 1, wherein the subject has mild to moderate renal impairment as evidenced by an eGFR of 30-89 mL/min.

3. The method of claim 1, wherein the subject has moderate renal impairment as evidenced by an eGFR of 30-59 mL/min, MDRD.

4. The method of claim 1, wherein the eGFR of the subject is between ≥60 mL/min and <90 mL/min, MDRD.

5. The method of claim 1, wherein the subject has an absolute SALT score of ≥50 at the onset of treatment.

6. The method of claim 1, wherein the subject has severe alopecia areata at the onset of treatment.

7. The method of claim 1, wherein after 8 weeks of treating the subject has an absolute SALT score of ≤20.

8. The method of claim 1, wherein after 12 weeks of treating the subject has an absolute SALT score of ≤20.

9. The method of claim 1, wherein after 24 weeks of treating the subject has an absolute SALT score of ≤20.

10. The method of claim 1, wherein after 24 weeks of treating the subject has an absolute SALT score of ≤10.

11. The method of claim 1, wherein after 52 weeks of treating the subject has an absolute SALT score of ≤20.

12. The method of claim 1, wherein after 24 weeks of treating the subject
   i) reports a response of "satisfied" or "very satisfied" on the Hair Satisfaction Patient Reported Outcome (SPRO) scale,
   ii) reports a response of "much improved" or "very much improved" using the Patient Global Impression of Improvement (PGI-I), or
   iii) reports a response of "much improved" or "very much improved" using the Clinical Global Impression of Improvement (CGI-I).

13. The method of claim 1, wherein after 12 weeks of treating
   i) a reduction in score at least 1.5 points from baseline is reported by the subject on the Hair Satisfaction Patient Reported Outcome (SPRO) scale,
   ii) a reduction in score of at least 1.5 points from baseline is reported by the subject on the Patient Global Impression of Improvement (PGI-I),
   iii) a reduction in score of at least 1.0 point from baseline is reported by the subject on the Clinical Global Impression of Severity (CGI-S), or
   iv) an increase in score of at least 0.5 points from baseline is achieved by the subject on the Brigham Eyelash Tool for Alopecia (BELA) or the Brigham Eyebrow Tool for Alopecia (BETA).

14. The method of claim 1, wherein the subject is a human.

15. The method of claim 1, wherein 16 mg/day of Compound (I) or a pharmaceutically acceptable salt thereof is administered.

16. The method of claim 15, wherein the 16 mg/day of Compound (I) or a pharmaceutically acceptable salt thereof is administered as 8 mg twice per day.

17. A method of treating alopecia areata in a subject in need thereof, the method comprising:
    determining an estimated glomerular filtration rate (eGFR) of the subject; and orally administering 16 mg/day or 24 mg/day of Compound (I) or a pharmaceutically acceptable salt thereof to the subject, if the subject has an eGFR of ≥30 mL/min, MDRD, wherein Compound (I) is represented by the following structural formula:

Compound (I)

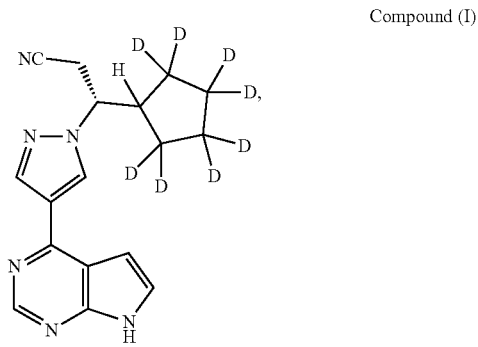

wherein each position designated specifically as deuterium has at least 95% incorporation of deuterium.

18. The method of claim 17, wherein the subject has mild to moderate renal impairment as evidenced by an eGFR of 30-89 mL/min.

19. The method of claim 17, wherein the subject has moderate renal impairment as evidenced by an eGFR of 30-59 mL/min, MDRD.

20. A method of treating alopecia areata, the method comprising:
    a) determining an estimated glomerular filtration rate (eGFR) of a population of subjects suffering from alopecia areata; and
    b) orally administering 16 mg/day or 24 mg/day of Compound (I) or a pharmaceutically acceptable salt thereof to a sub-group of the population of subjects having an eGFR of ≥30 mL/min, MDRD, wherein Compound (I) is represented by the following structural formula:

Compound (I)

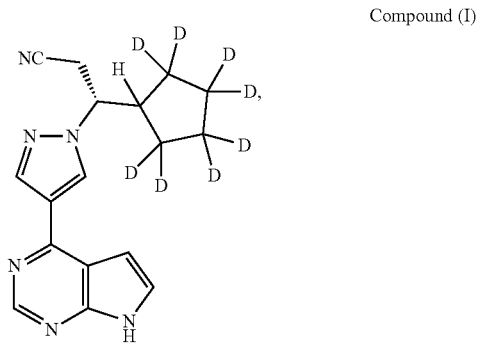

wherein each position designated specifically as deuterium has at least 95% incorporation of deuterium.

21. The method of claim 20, wherein the subject has mild to moderate renal impairment as evidenced by an eGFR of 30-89 mL/min.

22. The method of claim 20, wherein the subject has moderate renal impairment as evidenced by an eGFR of 30-59 mL/min, MDRD.

23. The method of claim 20, wherein the eGFR of the sub-group of the population of subjects is between ≥30 mL/min, MDRD and <60 mL/min, MDRD.

24. The method of claim 20, wherein the eGFR of the sub-group of the population of subjects is between ≥60 mL/min, MDRD and <90 mL/min, MDRD.

25. The method of claim 20, wherein the sub-group of the population of subjects has an absolute SALT score of ≥50 at the onset of treatment.

26. The method of claim 20, wherein the sub-group of the population of subjects has moderate to severe alopecia areata at the onset of treatment.

27. The method of claim 20, wherein after 12 weeks of treating at least 5% of the sub-group of the population of subjects has an absolute SALT score of ≤20.

28. The method of claim 20, wherein after 24 weeks of treating at least 25% of the sub-group of the population of subjects has an absolute SALT score of ≤20.

29. The method of claim 20, wherein after 24 weeks of treating at least 15% of the sub-group of the population of subjects has an absolute SALT score of ≤10.

30. A method of treating alopecia areata in a population of subjects in need thereof, the method comprising orally administering 16 mg/day or 24 mg/day of Compound (I) or a pharmaceutically acceptable salt thereof to a sub-group of the population of subjects having an eGFR of ≥30 mL/min, MDRD, wherein Compound (I) is represented by the following structural formula:

Compound (I)

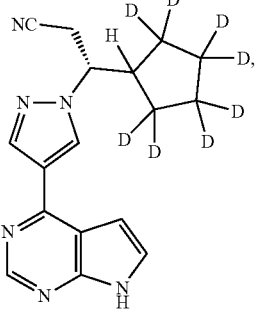

wherein each position designated specifically as deuterium has at least 95% incorporation of deuterium.

* * * * *

UNITED STATES PATENT AND TRADEMARK OFFICE
CERTIFICATE OF CORRECTION

Page 1 of 1

PATENT NO. : 12,364,699 B2
APPLICATION NO. : 18/905898
DATED : July 22, 2025
INVENTOR(S) : Christopher L. Brummel et al.

It is certified that error appears in the above-identified patent and that said Letters Patent is hereby corrected as shown below:

On the Title Page

The Assignee "Sun Pharmaceuticals Industries, Inc." appearing in Item (73) should read --Sun Pharmaceutical Industries, Inc.--.

Signed and Sealed this
Sixteenth Day of September, 2025

Coke Morgan Stewart
*Acting Director of the United States Patent and Trademark Office*